US011911440B2

(12) United States Patent
Passini et al.

(10) Patent No.: US 11,911,440 B2
(45) Date of Patent: *Feb. 27, 2024

(54) GENE THERAPY FOR NEURODEGENERATIVE DISORDERS

(71) Applicant: Genzyme Corporation, Cambridge, MA (US)

(72) Inventors: Marco A. Passini, Northborough, MA (US); Lamya Shihabuddin, West Newton, MA (US); Seng H. Cheng, Natick, MA (US)

(73) Assignee: Genzyme Corporation, Cambridge, MA (US)

( * ) Notice: Subject to any disclaimer, the term of this patent is extended or adjusted under 35 U.S.C. 154(b) by 9 days.

This patent is subject to a terminal disclaimer.

(21) Appl. No.: 18/054,500

(22) Filed: Nov. 10, 2022

(65) Prior Publication Data
US 2023/0135379 A1 May 4, 2023

Related U.S. Application Data

(63) Continuation of application No. 16/794,031, filed on Feb. 18, 2020, now abandoned, which is a continuation of application No. 16/449,221, filed on Jun. 21, 2019, now abandoned, which is a continuation of application No. 15/160,949, filed on May 20, 2016, now Pat. No. 10,369,193, which is a continuation of application No. 13/287,583, filed on Nov. 2, 2011, now abandoned, which is a continuation of application No. PCT/US2010/001239, filed on Apr. 27, 2010.

(60) Provisional application No. 61/268,059, filed on Jun. 8, 2009, provisional application No. 61/174,982, filed on May 2, 2009.

(51) Int. Cl.
*A61K 48/00* (2006.01)
*C12N 15/86* (2006.01)
*A61K 38/17* (2006.01)
*A61K 31/7088* (2006.01)
*C12N 7/00* (2006.01)
*C07K 14/47* (2006.01)

(52) U.S. Cl.
CPC ...... *A61K 38/1709* (2013.01); *A61K 31/7088* (2013.01); *A61K 48/00* (2013.01); *A61K 48/005* (2013.01); *A61K 48/0008* (2013.01); *A61K 48/0075* (2013.01); *C07K 14/4702* (2013.01); *C12N 7/00* (2013.01); *C12N 15/86* (2013.01); *C12N 2750/14121* (2013.01); *C12N 2750/14133* (2013.01); *C12N 2750/14143* (2013.01); *C12N 2750/14171* (2013.01)

(58) Field of Classification Search
CPC ..... A61K 48/00; A61K 48/0075; C12N 15/86
See application file for complete search history.

(56) References Cited

U.S. PATENT DOCUMENTS

| 5,173,414 A | 12/1992 | Lebkowski et al. |
| 5,328,470 A | 7/1994 | Nabel |
| 5,399,346 A | 3/1995 | Anderson et al. |
| 5,478,745 A | 12/1995 | Samulski et al. |
| 5,587,308 A | 12/1996 | Carter et al. |
| 5,605,690 A | 2/1997 | Jacobs et al. |
| 5,658,776 A | 8/1997 | Flotte et al. |
| 5,658,785 A | 8/1997 | Johnson |
| 5,677,158 A | 10/1997 | Zhou et al. |
| 5,753,500 A | 5/1998 | Shenk et al. |
| 5,756,283 A | 5/1998 | Wilson et al. |
| 5,786,211 A | 7/1998 | Johnson |
| 5,837,484 A | 11/1998 | Trempe et al. |
| 5,858,775 A | 1/1999 | Johnson |
| 5,866,696 A | 2/1999 | Carter et al. |
| 5,869,305 A | 2/1999 | Samulski et al. |
| 5,989,540 A | 11/1999 | Carter et al. |
| 5,990,279 A | 11/1999 | Carter et al. |
| 6,080,577 A | 6/2000 | Melki et al. |
| 6,146,874 A | 11/2000 | Zolotukhin et al. |
| 6,156,303 A | 12/2000 | Russell et al. |
| 6,165,781 A | 12/2000 | Carter et al. |
| 6,261,823 B1 | 7/2001 | Tang et al. |
| 6,503,888 B1 | 1/2003 | Kaplitt et al. |
| 6,566,118 B1 | 5/2003 | Atkinson |
| 6,573,099 B2 | 6/2003 | Graham |
| 6,596,535 B1 | 7/2003 | Carter |
| 6,686,200 B1 | 2/2004 | Dong et al. |
| 6,989,264 B2 | 1/2006 | Atkinson |
| 6,995,006 B2 | 2/2006 | Atkinson |

(Continued)

FOREIGN PATENT DOCUMENTS

BR 112015002168 A2 11/2017
JP H08-228785 A 9/1996

(Continued)

OTHER PUBLICATIONS

Foust et al. (2008) "Neonatal intraperitoneal or intravenous injections of recombinant adeno-associated virus type 8 transduce dorsal root ganglia and lower motor neurons" Human gene therapy, 19(1), 61-70. (Year: 2008).*

McCarty, Douglas M. (2008) "Self-complementary AAV vectors; advances and applications" Molecular therapy, 16(10), 1648-1656. (Year: 2008).*

Xu et al. (2001) "CMV-β-actin promoter directs higher expression from an adeno-associated viral vector in the liver than the cytomegalovirus or elongation factor 1α promoter and results in therapeutic levels of human factor X in mice" Human gene therapy, 12(5), 563-573. (Year: 2001).*

(Continued)

*Primary Examiner* — James D Schultz
*Assistant Examiner* — James Joseph Graber
(74) *Attorney, Agent, or Firm* — McNeill Baur PLLC

(57) ABSTRACT

Compositions and methods for treating disorders affecting motor function, such as motor function affected by disease or injury to the brain and/or spinal cord, are disclosed.

20 Claims, 14 Drawing Sheets

Specification includes a Sequence Listing.

(56) References Cited

U.S. PATENT DOCUMENTS

| | | |
|---|---|---|
| 7,125,717 B2 | 10/2006 | Carter |
| 7,465,583 B2 | 12/2008 | Samulski et al. |
| 7,765,583 B2 | 7/2010 | Kalonji et al. |
| 7,785,888 B2 | 8/2010 | Carter |
| 7,790,154 B2 | 9/2010 | Samulski |
| 7,846,729 B2 | 12/2010 | Carter |
| 8,093,054 B2 | 1/2012 | Carter |
| 8,361,457 B2 | 1/2013 | Samulski |
| 8,926,967 B2 | 1/2015 | Dodge et al. |
| 9,034,836 B2 | 5/2015 | Dodge et al. |
| 9,415,119 B2 | 8/2016 | Passini et al. |
| 9,415,121 B2 | 8/2016 | Kaspar et al. |
| 9,890,394 B2 | 2/2018 | O'riordan et al. |
| 10,080,783 B2 | 9/2018 | Dodge et al. |
| 10,208,318 B2* | 2/2019 | Barkats ................ C12N 15/86 |
| 10,369,193 B2 | 8/2019 | Passini et al. |
| 10,744,210 B2* | 8/2020 | Dodge et al. ...... A61K 48/0075 514/44 R |
| 10,821,154 B2 | 11/2020 | Passini et al. |
| 10,920,245 B2 | 2/2021 | O'riordan et al. |
| 11,040,116 B2 | 6/2021 | Kaspar et al. |
| 11,219,696 B2 | 1/2022 | Kaspar et al. |
| 2002/0041884 A1 | 4/2002 | Evans et al. |
| 2003/0219735 A1 | 11/2003 | Carter |
| 2004/0166122 A1 | 8/2004 | Evans et al. |
| 2005/0032219 A1 | 2/2005 | Aubourg et al. |
| 2005/0100923 A1 | 5/2005 | Dreyfuss et al. |
| 2007/0087433 A1 | 4/2007 | Carter |
| 2007/0253936 A1 | 11/2007 | Kay et al. |
| 2008/0187512 A1 | 8/2008 | Li |
| 2008/0206197 A1 | 8/2008 | Carter |
| 2009/0017542 A1 | 1/2009 | Colosi |
| 2009/0069261 A1 | 3/2009 | Dodge et al. |
| 2009/0130079 A1 | 5/2009 | Dodge et al. |
| 2009/0286857 A1 | 11/2009 | Oriordan et al. |
| 2010/0130594 A1 | 5/2010 | Barkats |
| 2010/0240739 A1 | 9/2010 | Barkats |
| 2010/0267812 A1 | 10/2010 | Dodge et al. |
| 2011/0086833 A1 | 4/2011 | Paushkin et al. |
| 2011/0104117 A1 | 5/2011 | Carter |
| 2012/0177605 A1 | 7/2012 | Kaspar et al. |
| 2012/0184602 A1 | 7/2012 | Carter |
| 2013/0287736 A1 | 10/2013 | Passini et al. |
| 2015/0313970 A1 | 11/2015 | Dodge et al. |
| 2016/0038613 A1 | 2/2016 | Kaspar et al. |
| 2016/0067312 A1 | 3/2016 | Dodge et al. |
| 2016/0074474 A1 | 3/2016 | Passini et al. |
| 2016/0168589 A1 | 6/2016 | Carter |
| 2017/0087212 A1 | 3/2017 | Passini et al. |
| 2017/0096683 A1 | 4/2017 | Scaria et al. |
| 2019/0083582 A1 | 3/2019 | Dodge et al. |
| 2020/0101138 A1 | 4/2020 | Dodge et al. |
| 2020/0384076 A1 | 12/2020 | Passini et al. |

FOREIGN PATENT DOCUMENTS

| | | |
|---|---|---|
| JP | 2008-540435 A | 11/2008 |
| WO | WO 95/13365 A1 | 5/1995 |
| WO | WO 95/13392 A1 | 5/1995 |
| WO | 1995028493 A1 | 10/1995 |
| WO | 9528948 A1 | 11/1995 |
| WO | WO 96/17947 A1 | 6/1996 |
| WO | WO 96/17947 C1 | 6/1996 |
| WO | WO 96/39530 A2 | 12/1996 |
| WO | WO 96/39530 A3 | 12/1996 |
| WO | WO 96/39530 C1 | 12/1996 |
| WO | WO 97/17458 A1 | 5/1997 |
| WO | 9732018 A2 | 9/1997 |
| WO | WO 97/32990 A1 | 9/1997 |
| WO | WO 98/27204 A2 | 6/1998 |
| WO | WO 98/27204 A3 | 6/1998 |
| WO | WO 98/27204 C1 | 6/1998 |
| WO | WO 98/27207 A1 | 6/1998 |
| WO | WO 98/32880 A1 | 7/1998 |
| WO | WO 99/11764 A2 | 3/1999 |
| WO | WO 99/11764 A3 | 3/1999 |
| WO | WO 99/20773 A2 | 4/1999 |
| WO | WO 99/20773 A3 | 4/1999 |
| WO | WO 99/20779 A1 | 4/1999 |
| WO | 9941416 A2 | 8/1999 |
| WO | 9947691 A1 | 9/1999 |
| WO | WO 00/14205 A2 | 3/2000 |
| WO | WO 00/14205 A3 | 3/2000 |
| WO | WO 00/14205 C1 | 3/2000 |
| WO | WO 00/65038 A2 | 11/2000 |
| WO | WO 00/65038 A3 | 11/2000 |
| WO | WO 00/73481 A1 | 12/2000 |
| WO | WO 01/11034 A2 | 2/2001 |
| WO | WO 01/11034 A3 | 2/2001 |
| WO | 2001066137 A1 | 9/2001 |
| WO | 2003004660 A1 | 1/2003 |
| WO | 2003052052 A2 | 6/2003 |
| WO | 2003046142 A3 | 10/2003 |
| WO | 2003039459 A3 | 11/2003 |
| WO | 2003052052 A3 | 2/2004 |
| WO | WO 2004/098648 A1 | 11/2004 |
| WO | WO-2006-119341 A2 | 11/2006 |
| WO | WO-2006-119341 A3 | 11/2006 |
| WO | WO 2006/119458 A1 | 11/2006 |
| WO | WO 2006/119458 A9 | 11/2006 |
| WO | 2007084737 A2 | 7/2007 |
| WO | WO 2007/146046 A2 | 12/2007 |
| WO | WO 2007/146046 A3 | 12/2007 |
| WO | 2008042420 A2 | 4/2008 |
| WO | WO 2008/042420 A2 | 4/2008 |
| WO | WO 2008/042420 A3 | 4/2008 |
| WO | 2008092481 A1 | 8/2008 |
| WO | 2009012176 A2 | 1/2009 |
| WO | 2009013290 A1 | 1/2009 |
| WO | WO-2009/013290 A1 | 1/2009 |
| WO | 2009043936 A1 | 4/2009 |
| WO | WO-2009/043936 A1 | 4/2009 |
| WO | 2009012176 A3 | 5/2009 |
| WO | 2010071832 A1 | 6/2010 |
| WO | WO 2010/129021 A1 | 11/2010 |
| WO | 2014022582 A1 | 2/2014 |
| WO | 2014125101 A1 | 8/2014 |
| WO | 2015168666 A2 | 11/2015 |

OTHER PUBLICATIONS

Lefebvre et al. (1995) "Identification and characterization of a spinal muscular atrophy-determining gene" Cell, 80(1), 155-165. (Year: 1995).*

Duque et al. (Apr. 2009) "Intravenous administration of self-complementary AAV9 enables transgene delivery to adult motor neurons" Molecular Therapy, 17(7), 1187-1196. (Year: 2009).*

Foust et al. (Dec. 2008) "Intravascular AAV9 preferentially targets neonatal neurons and adult astrocytes" Nature biotechnology, 27(1), 59-65. (Year: 2008).*

Wong et al. (2006) "Lentivirus-mediated gene transfer to the central nervous system: therapeutic and research applications" Human gene therapy, 17(1), 1-9. (Year: 2006).*

Hollis et al. (2008) "Efficient retrograde neuronal transduction utilizing self-complementary AAV1" Molecular Therapy, 16(2), 296-301. (Year: 2008).*

Amado, D. et al. (Mar. 3, 2010). "Safety And Efficacy Of Subretinal Readministration Of A Viral Vector In Large Animals To Treat Congenital Blindness," Sci. Transl. Med. 2(21):2lral6, 19 pages.

Avexis, Inc. (May 18, 2020). "Annex I: Summary of Product Characteristics," European Medicines Agency as retrieved on http://www.ema.europa.eu, 39 pages.

Avexis, Inc. (May 2017). "AVXS-101 (Onasemnogene Abeparvovec) GMO Environmental Risk Assessment," European Medicines Agency, 32 pages.

Avila, A.M. et al. (Mar. 2007). "Trichostatin A Increases SMN Expression and Survival in a Mouse Model of Spinal Muscular Atrophy," J. Clin. Invest. 117(3):659-671.

Bankiewicz, K.S. et al. (Oct. 2006, e-pub. Jul. 7, 2006). "Long-Term Clinical Improvement In MPTP-Lesioned Primates After Gene Therapy With Aavhaadc," Mol. Ther. 14, 564-570.

(56) References Cited

OTHER PUBLICATIONS

Bebee, T.W. et al. (2012, e-pub. Apr. 29, 2012). "Mouse Models Of SMA: Tools For Disease Characterization And Therapeutic Development," Hum. Genet. 131:1277-1293.

Benkhelifa-Ziyyat, S. et al. (Feb. 2013, e-pub. Jan. 8, 2013). "Intramuscular scAAV9-SMN Injection Mediates Widespread Gene Delivery to the Spinal Cord and Decreases Disease Severity in SMA Mice," Molecular Therapy 21(2):282-290.

Bevan, A. et al. (Nov. 2011, Aug. 2, 2011). "Systemic Gene Delivery in Large Species for Targeting Spinal Cord, Brain, and Peripheral Tissues for Pediatric Disorders," Mol. Ther. 19(11):1971-1980.

Bossis, I. et al. (Jun. 2003). "Cloning of an Avian Adeno-Associated Virus (AAAV) and Generation of Recombinant AAAV Particles," J. Virol. 77(12):6799-6810.

Boutin, S. et al. (Jun. 2010, e-pub. Apr. 28, 2010). "Prevalence of Serum IgG and Neutralizing Factors Against Adeno-Associated Virus (AAV) Types 1, 2, 5, 6, 8, and 9 in the Healthy Population: Implications for Gene Therapy Using AAV Vectors," Hum. Gene Ther. 21:704-712.

Bowerman, M. et al. (2012). "A Critical smn Threshold in Mice Dictates Onset of an Intermediate Spinal Muscular Atrophy Phenotype Associated with a Distinct Neuromuscular Junction Pathology," Neuromuscul. Disord. 22:263-276.

Bu, J. et al. (May 2012). "Identifying Motor Neuron Transduction Efficiencies that are Efficacious in SMA Mice and Achievable by Intrathecal Delivery in a Large Animal Model," Molecular Therapy 20(1):S31, No. 76, 1 page.

Butchbach, M.E. R. et al. (2010). "Effects of 2,4-diaminoquinazoline Derivatives on SMN Expression and Phenotype in a Mouse Model for Spinal Muscular Atrophy," Hum. Mol. Genet. 19(3):454-467.

Chen, S-H. et al. (Apr. 1994). "Gene Therapy for Brain Tumors: Regression of Experimental Gliomas by Adenovirus-Mediated Gene Transfer in Vivo," Proc. Natl. Acad. Sci. USA 91:3054-3057.

Chen, T.-H. et al. (Dec. 14, 2010). Randomized, Double-Blind, Placebo-Controlled Trial of Hydroxyurea in Spinal Muscular Atrophy, Neurology 75:2190-2197.

Clark, K.R. et al. (Apr. 10, 1999). "Highly Purified Recombinant Adeno-Associated Virus Vectors are Biologically Active and Free of Detectable Helper and Wild-Type Viruses," Hum. Gene Ther. 10(6):1031-1039.

Coovert, D.D. et al. (1997). "The Survival Motor Neuron Protein in Spinal Muscular Atrophy" Hum Mol Genet 6(8):1205-1214.

Davidson, B.L. et al. (Mar. 28, 2000). "Recombinant Adeno-Associated Virus Type 2, 4, and 5 Vectors: Transduction of Variant Cell Types and Regions in the Mammalian Central Nervous System," PNAS 97(7):3428-3432.

Dominguez, E. et al. (2011, e-pub. Nov. 30, 2010). "Intravenous scAAV9 Delivery of a Codon-Optimized SMN1 Sequence Rescues SMA Mice," Hum. Mol. Genet. 20(4):681-693.

Duque, S. (Jul. 2009). "Intravenous Administration of Self-Complementary AAV9 Enables Transgene Delivery to Adult Motor Neurons," Mol. Ther. 17(7):1187-1196.

European Medicines Agency Science Medicines Health (Mar. 26, 2020). "Assessment Report: Zolgensma," European Medicines Agency, EMA/200482/2020, 150 pages.

Fallini, C. et al. (Jun. 26, 2012, e-pub Jan. 28, 2012). "Spinal Muscular Atrophy: The Role of SMN in Axonal mRNA Regulation," Brain Res. 1462:81-92, 19 pages.

Farooq, F. et al. (Aug. 2011). "Prolactin Increases SMN Expression and Survival in a Mouse Model of Severe Spinal Muscular Atrophy Via The STAT5 Pathway," J. Clin, Invest. 121(8):3042-3050.

Federici, T. et al. (2012, e-pub Sep. 15, 2011). "Robust Spinal Motor Neuron Transduction Following Intrathecal Delivery of AA V9 pigs," Gene Ther. 19:852-859.

Foust, K.D. et al. (Mar. 2010). "Rescue of the Spinal Muscular Atrophy Phenotype in a Mouse Model by Early Postnatal Delivery of SMN," Nat. Biotech. 28(3):271-274, 11 pages.

Gao, G. et al. (Jun. 2004). "Clades of Adeno-Associated Viruses are Widely Disseminated in Human Tissues," J. Virol. 78(12):6381-6388.

Gao, G. et al. (May 13, 2003). "Adeno-Associated Viruses Undergo Substantial Evolution in Primates During Natural Infections," PNAS 100(10):6081-6086.

Gao, G. et al. (Sep. 3, 2002). "Novel Adeno-Associated Viruses from Rhesus Monkeys as Vectors for Human Gene Therapy," PNAS 99(18):11854-11856.

Garbes, L. et al. (Jul. 7, 2009). "LBH589 Induces up to 10-Fold SMN Protein Levels by Several Independent Mechanisms and is Effective Even in Cells From SMA Patients Non-Responsive to Valproate," Hum Mol Genet. 18(19):3645-3658.

Glascock, J.J. et al. (Jan. 6, 2012). "Direct Central Nervous System Delivery Provides Enhanced Protection Following Vector Mediated Gene Replacement In A Severe Model Of Spinal Muscular Atrophy," Biochemical and Biophysical Research Communications 417(1):376-381, 11pages.

Glascock, J.J. et al. (Mar. 2012). "Decreasing Disease Severity in Symptomatic, Smn-/-;SMN2+/ +, Spinal Muscular Atrophy Mice Following scAAV9-SMN Delivery," Human Gene Therapy 23(3):330-335.

Gray S.J. (Apr. 2013). "Global CNS Gene Delivery and Evasion of Anti-AAV Neutralizing Antibodies by Intrathecal AAV Administration in Non-Human Primates," Gene Therapy 20(4)450-459.

Gray, S.J. et al. (Jun. 2011, e-pub Apr. 12, 2011). "Preclinical Differences of Intravascular AAV9 Delivery to Neurons and Glia: a Comparative Study of Adult Mice and Nonhuman Primates," Mol. Ther. 19(6):1058-1069.

Guo, Z.S. et al. (Sep. 1996). "Evaluation of Promoter Strength for Hepatic Gene Expression in Vivo Following Adenovirus-Mediated Gene Transfer," Gene Ther. 3(9):802-810.

Hamilton, G. et al. (Jan. 2013). "Spinal Muscular Atrophy: Going Beyond the Motor Neuron," Trends Mol. Med. 19(1):40-50.

Heier, C.R. et al. (2009, Jan. 15, 2009). "Translational Readthrough by the Aminoglycoside Geneticin (G418) Modulated SMN Stability in vitro and Improves Motor Function in SMA Mice in vivo," Hum. Mol. Genet. 18(7):1310-1322.

Hinderer, C. et al. (Jan. 1, 2018). "Evaluation Of Intrathecal Routes Of Administration For Adeno-Associated Viral Vectors In Large Animals," Human Gene Therapy 29(1):15-24.

Hua, Y. et al. (2010, e-pub. Jul. 12, 2010). "Antisense Correction of SMN2 Splicing in the CNS Rescues Necrosis in a Type III SMA Mouse Model," Genes Dev. 24:1634-1644.

Hua, Y. et al. (Apr. 2008). "Antisense Masking Of An Hnrnp A1/A2 Intronic Splicing Silencer Corrects SMN2 Splicing In Transgenic Mice," Am. J. Hum. Genet. 82:834-848.

Hua, Y. et al. (Oct. 5, 2011). "Peripheral SMN Restoration is Essential for Long-Term Rescue of a Severe Spinal Muscular Atrophy Mouse Model," Nature 478:123-126, 11 pages.

International Search Report dated Aug. 13, 2013, for PCT Application No. PCT/US2013/039163, filed on May 1, 2013, 7 pages.

Kim, D.W. et al. (1990). "Use of the Human Elongation Factor 1α Promoter as a Versatile and Efficient Expression System," Gene 91(2):217-223.

Kolb, S.J. et al. (Aug. 2011, e-pub. Apr. 11, 2011). "Spinal Muscular Atrophy: A Timely Review," Arch. Neurol. 68(8):979-984.

Kole, R. et al. (Feb. 2012, e-pub. Jan. 20, 2012). "RNA Therapeutics: Beyond RNA Interference and Antisense Oligonucleotides," Nature Rev. Drug Dis. 11:125-140.

Kotin, R. (Jul. 1994). "Prospects for the Use of Adeno-Associated Virus as a Vector for Human Gene Therapy," Hum. Gene Ther. 5(7):793-801.

Le, T.T. et al. (2005) "SMNΔ7, The Major Product of the Centromeric Survival Motor Neuron (SMN2) Gene, Extends Survival In Mice with Spinal Muscular Atrophy and Associates with Full-length SMN," Hum Mol. Genet. 14(6):845-857.

Lewelt, A. et al. (Feb. 2012), "New Therapeutic Approaches To Spinal Muscular Atrophy," Curr. Neurol. Neurosci. Rep. 12(1):42-53, 17 pages.

Li, C. et al. (Apr. 2020). "Engineering Adeno-Associated Virus Vectors For Gene Therapy," Nature Reviews 21:255-272.

Lorson, M.A. et al. (Dec. 2011, e-pub. Feb. 25, 2011). "Disruption Of The Survival Motor Neuron (SMN) Gene In Pigs Using Ssdna," Transgenic Res. 20(6):1293-1304.

(56) References Cited

OTHER PUBLICATIONS

Markowitz, J.A. et al. (2012). "Spinal Muscular Atrophy: A Clinical And Research Update," Ped. Neurol. 46:1-12.
Mattis, V.B. et al. (2009). "Delivery of a Read-Through Inducing Compound, TC007, Lessens the Severity of a Spinal Muscular Atrophy Animal Model," Hum. Mol. Genet. 18(20):3906-3913.
McCarty, D.M., (2003). "Adeno-Associated Virus Terminal Repeat (TR) Mutant Generates Self-Complementary Vectors To Overcome The Rate-Limiting Step To Transduction In Vivo," Gene Therapy 10:2112-2118.
Mercuri, E. et al (Jan. 2, 2007, e-pub. Nov. 2, 2006). "Randomized, Double Blind, Placebo-Controlled Trial Of Phenylbutyrate In Spinal Muscular Atrophy," Neurology 68(1):51-55.
Monani, U.R. et al. (1999). "A Single Nucleotide Difference that Alters Splicing Patterns Distinguishes the SMA gene SMNI from the Copy Gene SMN2," Hum. Mol. Genet. 8(7):1177-1183.
Nathwani, A.C. et al. (Dec. 22, 2011, e-pub. Dec. 10, 2011). "Adenovirus-Associated Virus Vector-Mediated Gene Transfer in Hemophilia B," N Engl J Med 365(25):2357-2365.
Niwa, H. et al. (Dec. 1991). "Efficient Selection for High-Expression Transfectants with a Novel Eukaryotic Vector," Gene. 108(2):193-199.
Ohno, K. et al. (Jun. 14, 2019, e-pub. Dec. 8, 2018). "Kinetics And MR-Based Monitoring Of AAV9 Vector Delivery Into Cerebrospinal Fluid Of Nonhuman Primates," Mol Ther Methods Clin Dev. 13:47-54.
Passini, M.A. et al. (Jul. 2014). "Translational Fidelity Of Intrathecal Delivery Of Self-Complementary AAV9-Survival Motor Neuron 1 For Spinal Muscular Atrophy," Human Gene Therapy 25(7):619-630.
Passini, M.A. et al. (Jun. 2003). "Intraventricular Brain Injection of Adeno-Associated Virus Type 1 (AAV1) in Neonatal Mice Results in Complementary Patterns of Neuronal Transduction to AAV2 and Total Long-Term Correction of Storage Lesions in the Brains of β-Glucuronidase-Deficient Mice," J. Virol. 77(12):7034-7040.
Passini, M.A. et al. (Mar. 2, 2011). "Antisense Oligonucleotides Delivered To The Mouse CNS Ameliorate Symptoms Of Severe Spinal Muscular Atrophy," Sci. Transl. Med. 3(72):72ra18, 12 pages.
Passini, M.A. et al. (May 17, 2011, e-pub. Feb. 19, 2011). "Prospects for the Gene Therapy of Spinal Muscular Atrophy" Trends Mol. Med. 17(5):259-265.
Pechan, P. et al. (Jan. 2009, e-pub. Jul. 17, 2008). "Novel Anti-VEGF Chimeric Molecules Delivered by AAV Vectors for Inhibition of Retinal Neovascularization," Gene Ther. 16(1):10-16.
Rochette, C.F. et al. (2001, e-pub. Mar. 2, 2001). "SMN Gene Duplication And The Emergence Of The SMN2 Gene Occurred In Distinct Hominids: SMN2 Is Unique To *Homo sapiens*" Human Genetics 108(3):255-266.
Samaranch, L. et al. (Apr. 2012, Dec. 27, 2011). "Adeno-Associated Virus Serotype 9 Transduction in the Central Nervous System of Nonhuman Primates," Hum. Gene Ther. 23:382-389.
Shababi, M. et al. (May 2012, e-pub Jan. 17, 2012). "Partial Restoration of Cardio-Vascular Defects in Rescued Severe Model of Spinal Muscular Atrophy," Journal of Molecular and Cellular Cardiology 52(5):1074-1082, 18 pages.
Singh, N.K. et al. (Feb. 2006). Splicing of a Critical Exon of Human Survival Motor Neuron is Regulated By A Unique Silencer Element Located in the Last Intron, Mol. Cell. Biol. 26(4):1333-1346.
Sumner, C.J. et al. (Nov. 2003). "Valproic Acid Increases SMN Levels in Spinal Muscular Atrophy Patient Cells," Ann. Neurol. 54(5):647-654.
Treleaven, C.M. et al. (Sep. 4, 2012, e-pub Jun. 26, 2012). "Gene Transfer to the CNS Is Efficacious in Immune-primed Mice Harboring Physiologically Relevant Titers of Anti-AAV Antibodies", Mol. Ther. 20(9):1713-1723.
U.S. Appl. No. 16/449,221, filed Jun. 21, 2019 by Passini et al. (The U.S. Patent Application is not submitted herewith pursuant to the waiver of 37 C.F.R. § 1.98(a)(2)(III) issued by the Office on Sep. 21, 2004).
Valori, C.F. (Jun. 9, 2010). "Systemic Delivery of scAAV9 Expressing SMN Prolongs Survival in A Model Of Spinal Muscular Atrophy," Sci Transl Med. 2(35ra42):9 pages.
Veldwijk, M.R. et al. (Aug. 2002). "Development and Optimization of a Real-Time Quantitative PCR-Based Method for the Titration of AAV-2 Vector Stocks," Mol. Ther. 6(2):272-278.
Wang, Z. et al. (Dec. 2003), "Rapid and Highly Efficient Transduction by Double-Stranded Adeno-Associated Virus Vectors In Vitro and In Vivo," Gene Ther 10(26):2105-2111.
Written Opinion dated Aug. 13, 2013, for PCT Application No. PCT/US2013/039163, filed on May 1, 2013, 5 pages.
Xiao, X. et al. (Mar. 1997). "Gene Transfer by Adeno-Associated Virus Vectors into the Central Nervous System", Exp. Neurobiol. 144(1):113-124.
Arakawa, Tsutomu et al., "Mechanism of Protein Salting In and Salting Out by Divalent Cation Salts: Balance between Hydration and Salt Binding", Biochemistry 1984, 23, 5912-5923.
Bartlett, Jeffrey S. et al., "Genetics and Biology of Adeno-Associated Virus", Chapter 4 of Viral Vectors, Gene Therapy and Neuroscience Applications, 1995, pp. 55-73.
Berns, K.I et al., "Biology of Adeno-associated Virus", in Adeno-Associated Virus (AAB) Vectors in Gene Therapy, Current Topics in Microbiology and Immunology, 1996, Springer-Verlag Berlin Heidelberg, 96 pages.
Bohinski, Robert J. et al., "Cis-active Elements Controlling Lung Cell-specific Expression of Human Pulmonary Surfactant Protein B Gene", The Journal of Biological Chemistry, vol. 26, No. 15, 1993, pp. 11160-11166.
Carter, B.J. et al., "Development of Adeno-associated Virus Vectors for Gene Therapy of Cystic Fibrosis", Development of Adeno-associated Virus Vectors, 1996, pp. 120-144.
Carter, Barrie J. et al., AAV DNA Replication, Integration and Genetics, Chapter 11 in Handbook of Parvoviruses, vol. I, CRC Press, Boca Raton, Florida, 1990.
Carter, Barrie J., "Variant and Defective Interfering Parvovirsues", Chapter 6 in The Parvoviruses, Plenum Press, New York, 1984.
Carter, Barrie J., U.S. Appl. No. 09/634,126, filed Aug. 8, 2002, now granted as U.S. Pat. No. 6,596,535 on Jul. 2, 2003.
Clark, K. Reed, "Recent advances in recombinant adeno-associated virus vector production", Kidney International, vol. 61, Symposium 1 (2002), pp. S9-S15.
Croyle, Ma et al., "Development of formulations that enhance physical stability of viral vectors for gene therapy", Gene Therapy (2001) 8, pp. 1281-1290.
Gatlin, Larry A. et al., "Formulation and Administration Techniques to Minimize Injection Pain and Tissue Damage Associated with Parenteral Products", Chapter 17 in Injectable Drug Development, Techniques to Reduce Pain and Irritation, Interpharm Press, Denver, Colorado, 1999, pp. 401-421.
Hermens, W.T.J.M.C. et al., "Comparison of the performance of an adeno- and adeno-associated viral vector encoding the growth cone protein B-50/GAP-43: A preliminary study", Chapter 7 in Viral Vectors, Towards application In neuroregeneration research, 1997, Netherlands, pp. 149-164.
Hölscher, Christina et al., "Cell Lines Inducibly Expressing the Adeno-Associated Virus (AAV) rep Gene: Requirements for Productive Replication of rep-Negative AAV Mutants", Journal of Virology, Nov. 1994, vol. 68, No. 11, p. 7169-7177.
Hörster, A. et al., "Recombinant AAV-2 harboring gfp-antisense/ribozyme fusion sequences monitor transduction, gene expression, and show anti-HIV-1 efficacy", Gene Therapy (1996) 6, 1231-1238.
Johnson, Brent F. et al., Effect of Environmental pH on Adenovirus-Associated Virus (39085), Proceedings of the Society for Experimental Biology and Medicine, 159 (1975), pp. 585-590.
Kaplitt, Michael G. et al., "Long-term gene expression and phenotypic correction using adeno-associated virus vectors in the mammalian brain", Nature Genetics, vol. 8, Oct. 1994, pp. 148-154.
Kaplitt, Michael G. et al., "Transfer and Expression of Potentially Therapeutic Genes into the Mammalian Central Nervous System in Vivo Using Adeno-Associated Viral Vectors", Chapter 12 of Viral Vectors, Gene Therapy and Neuroscience Applications, 1995, pp. 193-210.

(56) References Cited

OTHER PUBLICATIONS

Kaspar, Brian K. et al., U.S. Appl. No. 13/035,777, filed Feb. 25, 2011.
Labow, Mark A. et al., "The Adeno-Associated Virus rep Gene Inhibits Replication of an Adeno-Associated Virus/Simian Virus 40 Hybrid Genome in cos-7 Cells", Journal of Virology, May 1988, vol. 62, No. 5, p. 1705-1712.
Laughlin, Catherine A. et al., "Cloning of infectious adeno-associated virus genomes in bacterial plasmids", Gene. 23 (1983) 65-73.
Mamounas, M et al., "Increased titer of recombinant AAV vectors by gene transfer with adenovirus coupled to DNA-polylysine complexes", Gene Therapy (1995) 2, 429-432.
McCarty, DM et al., "Self-complementary recombinant adeno-associated virus (scAAV) vectors promote efficient transduction independently of DNA synthesis", Gene Therapy (2001) 8, 1248-1254.
Mingozzi, Federico et al., "Improved Hepatic Gene Transfer by Using an Adeno-Associated Virus Serotype 5 Vector", Journal of Virology, Oct. 2002, vol. 76, No. 20, p. 10497-10502.
Mount, Jane D. et al., "Sustained phenotypic correction of hemophilia B dogs with a factor IX null mutation by liver-directed gene therapy", Blood, Apr. 15, 2002, vol. 99, No. 8, p. 2670-2676.
O'Malley, Karen L. et al., "Isolation and Characterization of the Human Tyrosine Hydroxylase Gene: Identification of 5' Alternative Splice Sites Responsible for Multiple mRNAs", Biochemistry, 1987, 26, 6910-6914.
Passini, Marco A. et al., "CNS-targeted gene therapy improves survival and motor function in a mouse model of spinal muscular atrophy", The Journal of Clinical Investigation, vol. 120, No. 4, Apr. 2010, 1252-1264.
Phillips, M. Ian et al., "Prolonged Reduction of High Blood Pressure With an In Vivo, Nonpathogenic, Adeno-Associated Viral Vector Delivery of AT1-R mRNA Antisense", Viral Vector and Hypertension, Jan. 1997, vol. 29, No. 1, Part 2, pp. 374-380.
Potter, Mark et al., "Streamlined Large-Scale Production of Recombinant Adeno-Associated Virus (rAAV) Vectors", Methods in Enzymology, vol. 346, Gene Therapy Methods, Academic Press, 2002, Chapter 24, pp. 413-430.
Samulski, Richard Jude et al., "A Recombinant Plasmid from Which an Infectious Adeno-Associated Virus Genome Can Be Excised In Vitro and Its Use To Study Viral Replication", Journal of Virology, Oct. 1987, vol. 61, No. 10, p. 3096-3101.
Sommer, Jurg M. et al., "Quantifications of Adeno-Associated Virus Particles and Empty Capsids by Optical Density Measurement", Molecular Therapy, vol. 7, No. 1, Jan. 2003, pp. 122-128.
Vandenberghe, Luk H., "AAV Clades: Their Ability to Recombine and Cross Species-Barriers", No. 88, Molecular Therapy, vol. 9, Supplement 1, May 2004, S35.
Verhaagen, J. "Use of viral vectors to promote neuroregeneration", Abstract, Clinical Neuroscience, Jan. 1995, 3(5): 275-283.
Verhaagen, J. et al., "Expression of the growth-associated protein B-50/GAP43 via a defective herpes-simplex virus vector results in profound morphological changes in non-neuronal cells", Molecular Brain Research, 26 (1994), p. 26-36.
Welch, Peter J. et al., "Ribozyme gene therapy for hepatitis C virus infection", Clinical and Diagnostic Virology, 10 (1998), 163-171.
Wong, K.K. Jr., et al., "Adeno-associated Virus Based Vectors As Antivirals", 1996, pp. 145-172.
Wright, J. Fraser et al., "Recombinant adeno-associated virus: Formulation challenges and strategies for a gene therapy vector", Current Opinion in Drug Discovery & Development, 2003, vol. 6, No. 2, p. 174-178.
Wright, John Fraser, U.S. Appl. No. 60/575,997, filed Jun. 1, 2004.
Wu, Pei et al., "Mutational Analysis of the Adeno-Associated Virus Type 2 (AAV2) Capsid Gene and Construction of AAV2 Vectors with Altered Tropism", Journal of Virology, Sep. 2000, vol. 74, No. 18, p. 8635-8647.

Ye, Xuehai et al., "Regulated Delivery of Therapeutic Proteins After in Vivo Somatic Cell Gene Transfer", Science, Jan. 1, 1999, vol. 283, p. 88-91.
Zhang, Huang-Ge et al., "Recombinant Adenovirus Expressing AAV CAP and REP Supports Production of High-titer rAAV but is Unstable", No. 769., Molecular Therapy, vol. 1, No. 5, May 2000, p. 2 of 2, p. S278.
Zhang, Huang-Ge, "AdAAV support High-titer Production of rAAV but not Stable", No. 797., Molecular Therapy, vol. 1, No. 5, May 2000, p. 2 of 2, p. S286.
Zolotukhin, Sergei et al., "A "Humanized" Green Fluorescent Protein cDNA Adapted for High-Level Expression in Mammalian Cells", Journal of Virology, Jul. 1996, vol. 70, No. 7, p. 4646-4654.
Foust, Kevin D. et al., "Rescue of the spinal muscular atrophy phenotype in a mouse model by early postnatal deliver of SMN", Nature Biotechnology, vol. 28, No. 3., Mar. 2010, 271-274.
Alisky, J.M. et al. (Nov. 20, 2000). "Gene Therapy for Amyotrophic Lateral Sclerosis and Other Motor Neuron Diseases," Human Gene Therapy 11:2315-2329.
Anderson, W.F. (Apr. 30, 1998). "Human Gene Therapy," Nature 392(Suppl.):25-30.
Arnett, A. L.H. et al., (Jun. 1, 2009, e-pub. May 4, 2009). "Therapy For Neuromuscular Disorders," Current Opinion in Genetics & Development 19(3):290-297.
Atkinson, E.M. et al. (1998). "A High-Throughput Hybridization Method For Titer Determination Of Viruses and Gene Therapy Vectors," Nucleic Acids Res. 26(11):2821-2823.
Avila, A. M. et al. (Mar. 2007). "Trichostatin A Increases SMN Expression and Survival in a Mouse Model of Spinal Muscular Atrophy," The Journal of Clinical Investigation 117(3):659-671.
Azzouz, M. (Dec. 2004). "Lentivector-Mediated SMN Replacement in a Mouse Model of Spinal Muscular Atrophy," The Journal of Clinical Investigation 114(12):1726-1731.
Baba, Y. et al. (2012, e-pub. Aug. 21, 2012). "In Vitro Cell Subtype-Specific Transduction of Adeno-Associated Virus in Mouse And Marmoset Retinal Explant Culture," Biochimie 94:2716-2722.
Balagué, C. et al. (Apr. 1997). "Adeno-Associated Virus Rep78 Protein and Terminal Repeats Enhance Integration of DNA Sequences Into the Cellular Genome," J. Virol. 71(4):3299-3306.
Bantel-Schaal, U. et al. (1988). "Adeno-Associated Viruses Inhibit Sv40 DNA Amplification and Replication Of Herpes Simplex Virus In Sv40-Transformed Hamster Cells," Virology 164:64-74.
Bantel-Schaal, U. et al. (1988). "Dissociation Of Carcinogen-Induced Sv40 DNA-Amplification and Amplification Of AAV DNA In A Chinese Hamster Cell Line," Virology 166:113-122.
Berns (1990). "Parvoviridae and Their Replication," Chapter 62 In Virology, vol. 2, Raven Press, New York, pp. 1743-1763.
Berns, K.I. (1990). "Hepatitis B Virus," Chapter 77 In Virology, vol. 2, Raven Press, New York, pp. 2171-2236.
Broekman, M.L.D. (2006). AAV Vectors as Gene Delivery Vehicles in the Central Nervous System. PhD Thesis, Utrecht University, pp. 1-208.
Carter, B.J. (1983). "Variant and Defective Interfering Parvoviruses," Chapter 6 In The Parvoviruses. Berns, K.I., ed., Plenum Press, New York, pp. 209-258.
Carter, B.J. (1989). "Adeno-Associated Virus Helper Functions," in Chapter 13 In Handbook of Parvoviruses vol. I, pp. 255-282.
Carter, B.J. (1992). "Adeno-Associated Virus Vectors," Curr. Op. Biotechnol. 3:533-539.
Cheng, S.H. et al., (Oct. 1, 2010). "AAV-Mediated Augmentation Of SMN Levels For Spinal Muscular Atrophy," Abstract No. P3.29 Neuromuscular Disorders, Pergamon Press 20(9-10):650.
Clark, K.R. et al. (1995). "Cell Lines For The Production Of Recombinant Adeno-Associated Virus," Hum. Gene Therapy 6:1329-1341.
Coady, T.H. et al. (Aug. 2007, e-pub. Apr. 25, 2007). "Restoration of SMN Function: Delivery of a Trans-splicing RNA Re-Directs SMN2 Pre-mRNA Splicing," Mol. Ther. 15(8):1471-1478.
Corti, S. (Oct. 2008). "Neural Stem Cell Transplantation Can Ameliorate the Phenotype of a Mouse Model of Spinal Muscular Atrophy," The Journal of Clinical Investigation 118(10):3316-3330.

(56) References Cited

OTHER PUBLICATIONS

Cromartie, W.J. et al. (1977). "Arthritis In Rats After Systemic Injection Of Streptococcal Cells Or Cell Walls," *J. Exp. Med.* 146:1585-1602.
De La Maza, L.M. et al. (1980). "Molecular Structure Of Adeno-Associated Virus Variant DNA," *J. Biol. Chem.* 255:3194-3203.
Didonato, C.J. et al. (Jan. 20, 2003). "Development of a Gene Therapy Strategy for the Restoration of Survival Motor Neuron Protein Expression: Implications for Spinal Muscular Atrophy Therapy," *Hum Gene Ther.* 14(2):179-188. (Abstract Only).
Dong, J.Y. et al. (1996). "Quantitative Analysis Of The Packaging Capacity Of Recombinant Adeno-Associated Virus," *Hum. Gene Therapy* 7:2101-2112.
During, M. J. (1997). "Adeno-Associated Virus as a Gene Delivery System," *Advanced Drug Delivery Reviews* 27:83-94.
Ferrari, F.K. et al. (1996). "Second-Strand Synthesis Is A Rate-Limiting Step For Efficient Transduction By Recombinant Adeno-Associated Virus Vectors," *J. Virol.* 70:3227-3234.
Ferrari, F.K. et al. (Nov. 1997). "New Developments in the Generation of Ad-Free, High-Titer rAAV Gene Therapy Vectors," *Nature Med.* 3(11):1295-1297.
Fisher, K.J. et al. (1996). "Transduction With Recombinant Adeno-Associated Virus For Gene Therapy Is Limited By Leading-Strand Synthesis," *J. Virol.* 70:520-532.
Flotte, T.R. et al. (1992). "Gene Expression From Adeno-Associated Virus Vectors In Airway Epithelial Cells," *Am. J. Respir. Cell. Mol. Biol.* 7:349-356.
Flotte, T.R. et al. (Feb. 15, 1993). "Expression of the Cystic Fibrosis Transmembrane Conductance Regulator from a Novel Adeno-Associated Virus Promoter," *J. Biol. Chem.* 268(5):3781-3790.
Flotte, T.R. et al. (1995). "Adeno-Associated Virus Vectors For Gene Therapy," *Gene Therapy* 2:357-362.
Foust, K. D. et al. (Jan. 2009, e-pub. Dec. 21, 2008). "Intravascular AAV9 Preferentially Targets Neonatal Neurons and Adult Astrocytes," *Nature Biotechnology* 27(1):59-65.
Foust, K. D. et al. (Jan. 2008, e-pub. Dec. 3, 2007). "Neonatal Intraperitoneal or Intravenous Injections of Recombinant Adeno-Associated Virus Type 8 Transduce Dorsal Root Ganglia and Lower Motor Neurons," *Human Gene Therapy* 19:61-69.
Franz, C.K. (Mar. 2009, e-pub. Dec. 24, 2008). "Intraspinal Cord Delivery Of IGF-1 Mediated By Adeno-Associated Virus 2 Is Neuroprotective In A Rat Model Of Familial ALS" *Neurobiology of Disease* 33:473-481.
Fu, H. et al. (2003). "Self-Complementary Adeno-Associated Virus Serotype 2 Vector: Global Distribution and Broad Dispersion of AAV-Mediated Transgene Expression in Mouse Brain," *Molecular Therapy* 8:911-917.
Hauswirth, W.W. et al. (1979). "Adeno-Associated Virus DNA Replication: Nonunit-Length Molecules," *Virology* 93:57-68.
Hermonat, P.L. et al. (1984). "Genetics Of Adeno-Associated Virus: Isolation and Preliminary Characterization Of Adeno-Associated Virus Type 2 Mutants," *J. Virol.* 51:329-339.
Hermonat, P.L. et al. (1984). "Use Of Adeno-Associated Virus As A Mammalian DNA Cloning Vector: Transduction Of Neomycin Resistance Into Mammalian Tissue Culture Cells," *Proc. Natl. Acad. Sci. USA,* 81:6466-6470.
Hollis, E.R. et al., (Feb. 2008). "Efficient Retrograde Neuronal Transduction Utilizing Self Complementary AAV1," *Molecular Therapy* 16(2):296-301.
Klein, R.L. et al. (Jan. 2008). "AAV8, 9, Rh10, Rh43 Vector Gene Transfer in the Rat Brain: Effects of Serotype, Promoter and Purification Method," *MolTher.* 16(1):89-96.
Lebkowski, J.S. et al. (1988). "Adeno-Associated Virus: A Vector System For Efficient Introduction and Integration Of DNA Into A Variety Of Mammalian Cell Types," *Mol. Cell. Biol.* 8(10):3988-3996.
Lefebvre, S. et al. (Jan. 13, 1995). "Identification and Characterization of a Spinal Muscular Atrophy-Determining Gene," *Cell* 80(1):155-165.
Lim, S.T., (2010). "Viral Vectors For Neurotrophic Factor Delivery: A Gene Therapy Approach For Neurodegenerative Diseases Of The CNS," *Pharmacological Research* 61:14-26.
Liu, G. et al. (Oct. 2005). "Adeno-Associated Virus Type 4 (AAV4) Targets Ependyma and Astrocytes in the Subventricular Zone and RMS," *Gene Therapy* 12(20):1503-1508.
Lynch, C.M. et al. (1997). "Adeno-Associated Virus Vectors For Vascular Gene Delivery," *Circ. Res.* 80:497-505.
McCarty, D.M., (Oct. 2008, e-pub. Aug. 5, 2008). "Self-Complementary AAV Vectors; Advances and Applications," *Molecular Therapy* 16(10):1648-1656.
McLaughlin, S.K. et al. (1988). "Adeno-Associated Virus General Transduction Vectors: Analysis Of Proviral Structures," *J. Virol.* 62:1963-1973.
Muzyczka, N. (1992). "Use Of Adeno-Associated Virus As A General Transduction Vector For Mammalian Cells," *Curr. Top. Microbiol. Immunol.* 158:97-129.
Natkunarajah, M. et al., (Mar. 2008, e-pub. Nov. 15, 2007). "Assessment of Ocular Transduction Using Single-Stranded and Self-Complementary Recombinant Adeno-Associated Virus Serotype 2/8," *Gene Therapy* 15(6):463-467.
Narver, H. L. (Oct. 2008). "Sustained Improvement of Spinal Muscular Atrophy Mice Treated with Trichostatin A Plus Nutrition," *Ann Neurol* 64:465-470.
Passini, M.A., (Apr. 2010). "CNS-Targeted Gene Therapy Improves Survival And Motor Function In A Mouse Model Of Spinal Muscular Atrophy," *Journal of Clinical Investigation* 120(4):1253-1264.
Russell, J. et al. (1995). "Cis-Acting Components Of Human Papillomavirus (Hpv) Dna Replication: Linker Substitution Analysis Of The Hpv Type 11 Origin," *J. Virol.* 69(2):651-660.
Samulski, R.J. et al. (1989). "Helper-Free Stocks Of Recombinant Adeno-Associated Viruses: Normal Integration Does Not Require Viral Gene Expression," *J. Virol.* 63:3822-3828.
Sanlioglu, S. et al. (Mar. 1, 1999). "Two Independent Pathways for Recombinant Adeno-Associated Virus Genome Conversion Occur After UV-C and E4orf6 Augmentation of Transduction," *Hum. Gene Ther.* 10:591-602.
Srivastava, A. et al. (1983). "Nucleotide Sequence and Organization Of The Adeno-Associated Virus 2 Genome," *J. Virol.* 45:555-564.
Storek, B. et al. (Jan. 22, 2008). "Sensory Neuron Targeting by Self-Complementary AAV8 Via Lumbar Puncture for Chronic Pain," *PNAS* 105(3):1055-1060.
Su, H. et al. (Mar. 1, 1996). "Selective Killing of AFP-Positive Hepatocellular Carcinoma Cells by Adeno-Associated Virus Transfer of the Herpes Simplex Virus Thymidine Kinase Gene," *Hum. Gene Ther.* 7(4):463-470.
Supplementary European Search Report dated Oct. 17, 2012, for European Patent Application No. 10772363.7, filed on Apr. 27, 2010, 10 pages.
Tratschin, J. et al. (1984). "A Human Parvovirus, Adeno-Associated Virus, As A Eucaryotic Vector: Transient Expression and Encasidation Of The Procaryotic Gene For Chloramphenicol Acetyltransferase," *Mol. Cell. Biol.* 4(10):2072-2081.
Tratschin, J. et al. (1984). "Genetic Analysis Of Adeno-Associated Virus: Properties Of Deletion Mutants Constructed In Vitro and Evidence For An Adeno-Assocaited Virus Replication Function," *J. Virol.* 51(3):611-619.
Tratschin, J. et al. (1985). "Adeno-Associated Virus Vector For High-Frequency Integration, Expresion and Rescue Of Genes In Mammalian Cells," *Mol. Cell. Biol.* 5(11):3251-3260.
Urcelay, E. et al. (Apr. 1995). "Asymmetric Replication In Vitro from a Human Sequence Element is Dependent on Adeno-Associated Virus Rep Protein," *J. Virol.* 69(4):2038-2046.
Verma, I.M. et al. (Sep. 18, 1997). "Gene Therapy—Promises, Problems and Prospects," *Nature* 389:239-242.
Verma, I.M. et al. (2005; e-pub. Mar. 11, 2005). "Gene Therapy: Twenty-First Century Medicine," *Annu. Rev. Biochem.* 74:711-738.
Xiao, X. et. al. (Mar. 1998). "Production of High-Titer Recombinant Adeno-Associated Virus Vectors in the Absence of Helper Adenovirus," *Journal of Virology* 72(3):2224-2232.
Yakobson, B. et al. (1987). "Replication Of Adeno-Associated Virus In Synchronized Cells Without The Addition Of A Helper Virus," *J. Virol.* 61(4):972-987.

(56) References Cited

OTHER PUBLICATIONS

Yakobson, B. et al. (1988). "Replication Of Adeno-Associated Virus In Cells Irradiated With Uv Light At 254nm," *J. Virol.* 63(3):1023-1030.

Yalkinoglu, A.O. et al. (1988). "DNA Amplification Of Adeno-Associated Virus As A Response To Cellular Genotoxic Stress," *Cancer Res.* 48:3123-3129.

Allocca et al., "Novel Adeno-Associated Virus Serotypes Efficiently Transduce Murine Photoreceptors", Journal of Virology, vol. 81, No. 20, pp. 11372-11380 (Oct. 2007).

Gao et al., "Clades of Adeno-Associated Viruses Are Widely Disseminated in Human Tissues", Journal of Virology, vol. 78, No. 12, pp. 6381-6388 (Jun. 2004).

Inagaki et al., "Robust Systemic Transduction with AAV9 Vectors in Mice: Efficient Global Cardiac Gene Transfer Superior to That of AAV8", Mol Ther, 14(1), pp. 45-53 (2006).

Royo et al., "Specific AAV Serotypes Stably Transduce Primary Hippocampal and Cortical Cultures with High Efficiency and Low Toxicity", Brian Res, 1190: 15-22 (Jan. 23, 2008).

Xu et al., Human Gene Therapy (Mar. 20, 2001) 12:563-573 (Year: 2001).

Declaration of Lamysa Shihabuddin, PhD Under 37 C.F.R. 1.131, dated Feb. 16, 2023, 9 pages.

Non-Final Office Action issued in corresponding U.S. Appl. No. 18/046,363, dated Jan. 31, 2023, 16 pages.

Appendix 2A to Laboratory Stock Solutions and Equipment, Common Buffers and Stock Solutions, Current Protocols in Nucleic Acid Chemistry (2000), A.2A.1-A.2A.12.

Berkowitz, Steven A. et al., "Characterizing Biopharmaceuticals using Analytical Ultracentrifugation", Biophysical Characterization of Proteins in Developing Biopharmaceuticals, 211-260, 2015).

Berkowitz, Steven A. et al., "Monitoring the homogeneity of adenovirus preparations (a gene therapy delivery system) using analytical ultracentrifugation", Anal Biochem. 2007; 362(1):16-37.

Carpenter, John F. et al., "Rational Design of Stable Protein Formulations", Pharmaceutical Biotechnology, vol. 13, 2002, 38 pages.

Center for Drug Evaluation and Research (CDER), "Guidance for Industry, Estimating the Maximum Safe Starting Dose in Initial Clinical Trials for Therapeutics in Adult Healthy Volunteers", Food and Drug Administration, Jul. 2005, 30 pages.

Cole, James L. et al., "Analytical Ultracentrifucation as a Contemporary Biomolecular Research Tool", Journal of Biomolecular Techniques, vol. 10, issue 4, Dec. 1999, 163-176.

Cole, James L. et al., "Analytical Ultracentrifugation: Sedimentation Velocity and Sedimentation Equilibrium", Methods Cell Biol. 2008; 84: 143-179.

Dafforn, Timothy R. et al., "So how do you know you have a macromolecular complex?", Acta Crystallographica (2007), D63, 17-25.

European Medicines Agency, Committee for Medicinal Products for Human Use, Glybera Assessment Report, Jul. 19, 2012, 147 pages.

Freireich, Emil J. et al., "Quantitative comparison of toxicity of anticancer agents in mouse, rat, hamster, dog, monkey, and man.", Cancer Chemother. Rep. 50:219-44, 1966.

Gao, Kai et al., "Empty virions in AAV8 vector preparations reduce transduction efficiency and may cause total viral particle dose-limiting side effects", Molecular Therapy—Methods & Clinical Development (2014) 1:9; 8 pages.

Gennaro, Alfonso R., "Remington: The Science and Practice of Pharmacy", Nineteenth Ed., vol. I, Chapters 17, 18, 23 and 36 (1995).

Gennaro, Alfonso R., "Remington: The Science and Practice of Pharmacy", Nineteenth Ed., vol. II, Chapter 87, Parenteral Preparations, (1995).

Genzyme Corporation, Transmittal of Third Party Observation for European Application No. EP20160703205, dated Jul. 30, 2020, 33 pages.

Gombold, Jim et al., "Lot Release and Characterization Testing of Live-Virus-Based Vaccines and Gene Therapy Products, Part 2", BioProcess International, 4(5): 56-65, 2006.

Hoque, Mainul et al., "Chimeric Virus-like Particle Formation of Adeno-Associated Virus", Biochemical and Biophysical Research Communications, 266, 371-376 (1999).

Huang, James et al., "Aggregation of AAV Vectors, its Impact on Liver-directed Gene Transfer and Development of Vector Formulations to Prevent and Dissolve Aggregation and Enhance Gene Transfer Efficiency", Molecular Therapy, vol. 1, No. 5, May 2000, p. S286.

Ralston, Greg, "Introduction to Analytical Ultracentrifugation", Beckman Coulter Life Sciences, 1993, 94 pages.

Schuck, Peter, "Size-Distribution Analysis of Macromolecules by Sedimentation Velocity Ultracentrifugation and Lamm Equation Modeling", Biophysical Journal, vol. 78, Mar. 2000, 1606-1619.

Steinbach, Silke et al., "Assembly of adeno-associated virus type 2 capsids in vitro", Journal of General Virology (1997), 78, 1453-1462.

Wade, Ainley et al., "Handbook of Phamaceutical Excipients", The Pharmaceutical press: London, 1994, 454-458.

Zhao, Huaying et al., "Current Methods in Sedimentation Velocity and Sedimentation Equilibrium Analytical Ultracentrifugation", Curr Protoc Protin Sci. Feb. 2013, doi:10.1002/0471140864.ps2012s71, 52 pages.

\* cited by examiner

Fig. 3A 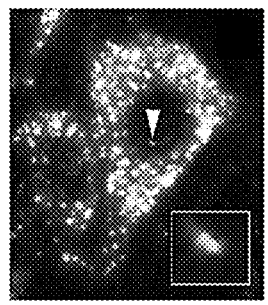 Fig. 3B 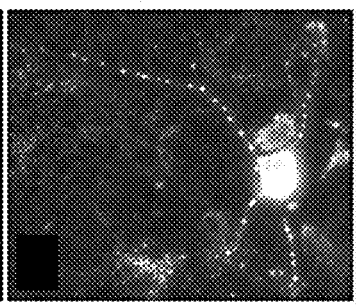 Fig. 3C 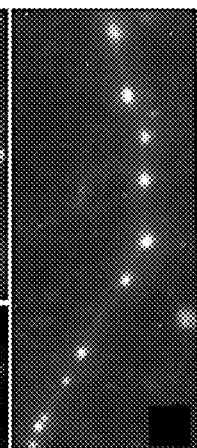

Fig. 3E 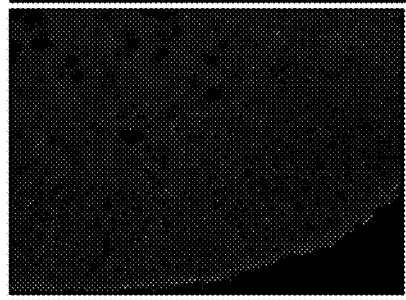 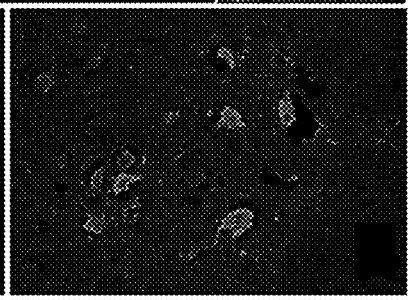 Fig. 3D
Fig. 3G 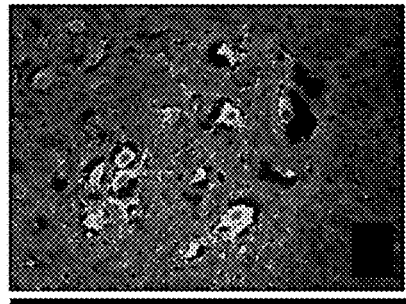 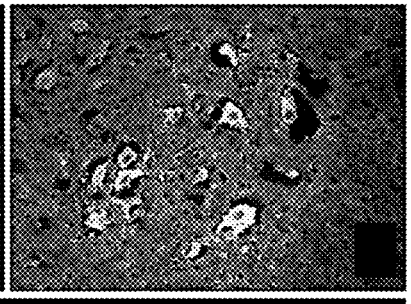 Fig. 3H
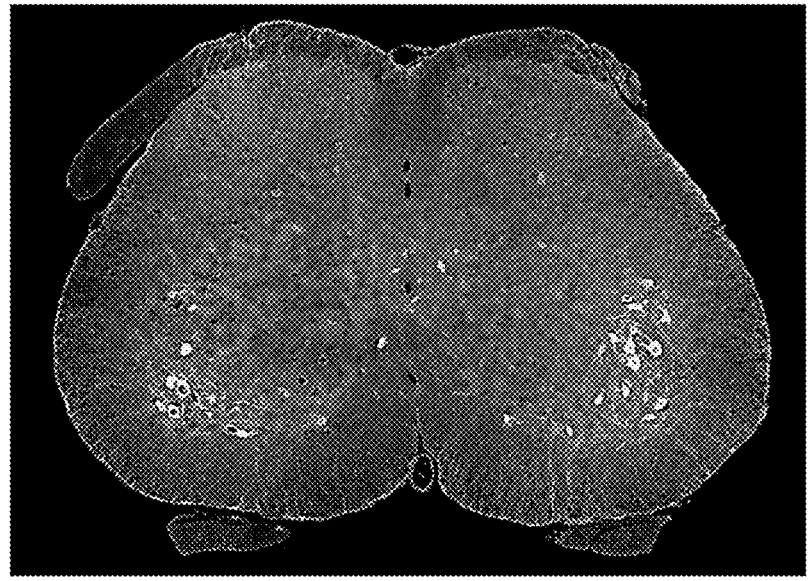
Fig. 3I

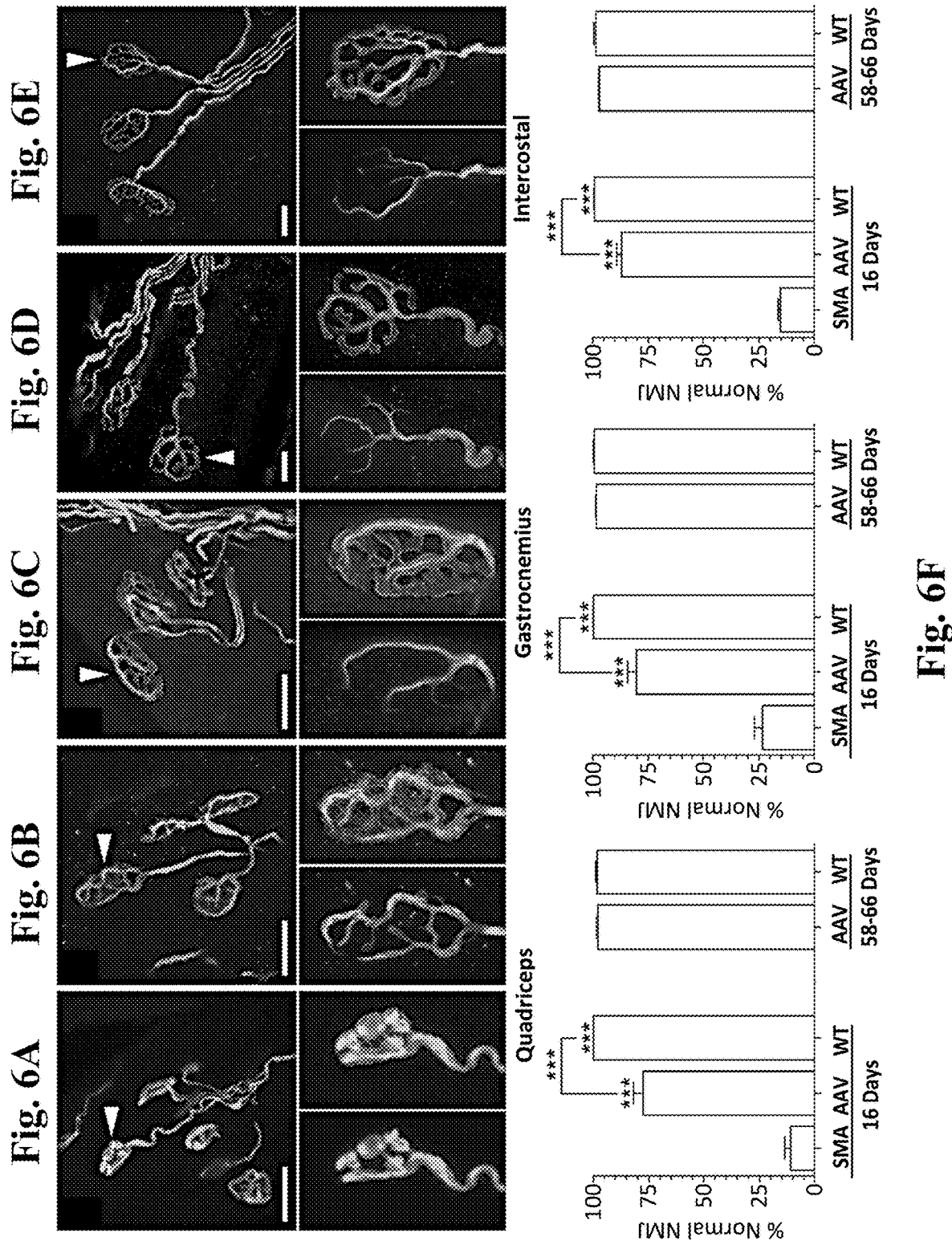

```
1    atggcgatga gcagcggcgg cagtggtggc ggcgtcccgg agcaggagga
51   ttccgtgctg ttccggcgcg gcacaggcca gagcgatgat tctgacattt
101  gggatgatac agcactgata aaagcatatg ataaagctgt ggcttcattt
151  aagcatgctc taaagaatgg tgacatttgt gaacttcgg gtaaaccaaa
201  aaccacacct aaaagaaaac ctgctaagaa gataaaagc caaagaaga
251  atactgcagc ttccttacaa cagtggaaag ttggggacaa atgttctgcc
301  atttggtcag aagacggttg catttaccca gctaccattg cttcaattga
351  ttttaagaga gaaacctgtg ttgtggttta cactggatat ggaaatagag
401  aggagcaaaa tctgtccgat ctactttccc caatctgtga agtagctaat
451  aatatagaac aaaatgctca agagaatgaa aatgaaagcc aagtttcaac
501  agatgaaagt gagaactcca ggtctcctgg aaataaatca gataacatca
551  agcccaaatc tgctccatgg aactctttc tccctccacc accccccatg
601  ccagggccaa gactgggacc aggaaagcca ggtctaaaat tcaatggccc
651  accaccgcca ccgccaccac caccacccca ttactatca tgctggctgc
701  ctccatttcc ttctggacca ccaataattc ccccaccacc tccatatgt
751  ccagattctc ttgatgatgc tgatgctttg ggaagtatgt taatttcatg
801  gtacatgagt ggctatcata ctggctatta tatgggtttc agacaaaatc
851  aaaagaagg aaggtgctca cattccttaa attaa
```

(SEQ ID NO: 1)

Fig. 9A

```
1    MAMSSGGSGGGVPEQEDSVLFRRGTGQSDDSDIWDDTALIKAYDKAVASF
51   KHALKNGDICETSGKPKTTPKRKPAKKNKSQKKNTAASLQQWKVGDKCSA
101  IWSEDGCIYPATIASIDFKRETCVVVYTGYGNREEQNLSDLLSPICEVAN
151  NIEQNAQENENESQVSTDESENSRSPGNKSDNIKPKSAPWNSFLPPPPPM
201  PGPRLGPGKPGLKFNGPPPPPPPPPHLLSCWLPPFPSGPPIIPPPPPIC
251  PDSLDDADALGSMLISWYMSGYHTGYYMGFRQNQKEGRCSHSLN
```

(SEQ ID NO: 2)

Fig. 9B

GENE THERAPY FOR NEURODEGENERATIVE DISORDERS

CROSS-REFERENCE TO RELATED APPLICATIONS

This application is a continuation of U.S. application Ser. No. 16/794,031, filed Feb. 18, 2020, which is a continuation of U.S. application Ser. No. 16/449,221, filed Jun. 21, 2019, now abandoned, which is a continuation of Ser. No. 15/160, 949, filed May 20, 2016, now granted as U.S. Pat. No. 10,369,193, which is a continuation of U.S. application Ser. No. 13/287,583, filed Nov. 2, 2011, now abandoned, which is a continuation of PCT/US2010/001239 filed Apr. 27, 2010, which claims the benefit under 35 USC § 119(e)(1) of U.S. Provisional Applications Nos. 61/174,982, filed May 2, 2009 and 61/268,059, filed Jun. 8, 2009, each of which are incorporated herein by reference in their entireties.

SEQUENCE LISTING

The present application contains a Sequence Listing which has been submitted electronically in XML format and is hereby incorporated by reference in its entirety. Said XML copy, created on Nov. 10, 2022, is named "2022-10-13_01183-0219-06US-T1_Seq_List.xml" and is 4,766 bytes in size.

TECHNICAL FIELD

The present invention relates generally to gene delivery methods. In particular, the invention relates to compositions and methods for treating disorders affecting motor function, such as motor function affected by disease or injury to the brain and/or spinal cord.

DESCRIPTION OF THE INVENTION

Gene therapy is an emerging treatment modality for disorders affecting the central nervous system (CNS). CNS gene therapy has been facilitated by the development of viral vectors capable of effectively infecting post-mitotic neurons. The central nervous system is made up of the spinal cord and the brain. The spinal cord conducts sensory information from the peripheral nervous system to the brain and conducts motor information from the brain to various effectors. For a review of viral vectors for gene delivery to the central nervous system, see Davidson et al., *Nature Rev.* (2003) 4:353-364.

Adeno-associated virus (AAV) vectors are considered useful for CNS gene therapy because they have a favorable toxicity and immunogenicity profile, are able to transduce neuronal cells, and are able to mediate long-term expression in the CNS (Kaplitt et al., *Nat. Genet.* (1994) 8:148-154; Bartlett et al., *Hum. Gene Ther.* (1998) 9:1181-1186; and Passini et al., *J. Neurosci.* (2002) 22:6437-6446).

One useful property of AAV vectors lies in the ability of some AAV vectors to undergo retrograde and/or anterograde transport in neuronal cells. Neurons in one brain region are interconnected by axons to distal brain regions thereby providing a transport system for vector delivery. For example, an AAV vector may be administered at or near the axon terminals of neurons. The neurons internalize the AAV vector and transport it in a retrograde manner along the axon to the cell body. Similar properties of adenovirus, HSV, and pseudo-rabies virus have been shown to deliver genes to distal structures within the brain (Soudan et al., *FASEB J.* (2001) 15:2283-2285; Breakefield et al., *New Biol.* (1991) 3:203-218; and deFalco et al., *Science* (2001) 291:2608-2613).

Several experimenters have reported that the transduction of the brain by AAV serotype 2 (AAV2) is limited to the intracranial injection site (Kaplitt et al., *Nat. Genet.* (1994) 8:148-154; Passini et al., *J. Neurosci.* (2002) 22:6437-6446; and Chamberlin et al., *Brain Res.* (1998) 793:169-175). There is also evidence that retrograde axonal transport of neurotrophic viral vectors, including AAV and lentiviral vectors, can also occur in select circuits of the normal rat brain (Kasper et al., *Mol. Ther.* (2002) 5:50-56; Kasper et al., *Science* (2003) 301:839-842 and Azzouz et al., *Nature* (2004) 429:413-417. Roaul et al., *Nat. Med.* (2005) 11(4): 423-428 and Ralph et al., *Nat. Med.* (2005) 11(4):429-433 report that intramuscular injection of lentivirus expressing silencing human Cu/Zn superoxide dismutase (SODI) interfering RNA retarded disease onset of amyotrophic lateral sclerosis (ALS) in a therapeutically relevant rodent model of ALS.

Cells transduced by AAV vectors may express a therapeutic transgene product, such as an enzyme or a neurotrophic factor, to mediate beneficial effects intracellularly. These cells may also secrete the therapeutic transgene product, which may be subsequently taken up by distal cells where it may mediate its beneficial effects. This process has been described as cross-correction (Neufeld et al., *Science* (1970) 169:141-146).

A property of the recombinant AAV vectors described above is the requirement that the single-stranded DNA (ssDNA) AAV genome must be converted into into double-stranded DNA (dsDNA) prior to expression of the encoded transgene. This step can be circumvented by the use of self-complementary vectors which package an inverted repeat genome that folds into dsDNA without requiring DNA synthesis or base-pairing between multiple vector genomes, thereby increasing efficiency of AAV-mediated gene transfer. For a review of self-complementary AAV vectors, see e.g., McCarty, D. M. *Molec. Ther.* (2008) 16:1648-1656.

Spinal muscular atrophy (SMA) is an autosomal recessive neuromuscular disorder caused by mutations in the survival motor neuron 1 (SMN1) gene and loss of encoded SMN protein (Lefebvre et al., *Cell* (1995) 80:155-165). The lack of SMN results in motor neuron degeneration in the ventral (anterior) horn of the spinal cord, which leads to weakness of the proximal muscles responsible for crawling, walking, neck control and swallowing, and the involuntary muscles that control breathing and coughing (Sumner C. J., *NeuroRx* (2006) 3:235-245). Consequently, SMA patients present with increased tendencies for pneumonia and other pulmonary problems such as restrictive lung disease. The onset of disease and degree of severity are determined in part by the phenotypic modifier gene SMN2, which is capable of making a small amount of SMN (Monani et al., *Hum. Mol. Genet.* (1999) 8:1177-1183; Lorson et al., *Proc. Natl. Acad. Sci. USA* (1999) 96:6307-6311). Thus, patients with a high SMN2 copy number (3-4 copies) exhibit a less severe form of the disease (referred to as Types II or III), whereas 1-2 copies of SMN2 typically result in the more severe Type I disease (Campbell et al., *Am. J. Hum. Genet.* (1997) 61:40-50; Lefebvre et al., *Nat. Genet.* (1997) 16:265-269). Currently, there are no effective therapies for SMA.

A fundamental strategy for treating this monogenic disorder is to increase SMN levels in SMA patients. One approach to accomplish this is to modulate the endogenous SMN2 gene with small molecules that activate the SMN2 promoter or correct the SMN2 pre-mRNA splicing pattern. The alteration of SMN2 splicing also can be realized with antisense oligonucleotides and trans-splicing RNAs. However, while modulating SMN2 in vitro increased SMN levels and reconstituted nuclear gems in SMA cell lines, efficacy studies with small molecule drugs have not translated to measurable improvements in the clinic (Oskoui et al., *Nerotherapeutics* (2008) 5:499-506).

SUMMARY OF THE INVENTION

The present invention is based on the discovery that both conventional recombinant AAV (rAAV) virions, as well as recombinant self-complementary AAV vectors (scAAV), are able to deliver genes to the CNS with successful expression in the CNS and treatment of neurodegenerative disease. This therapy approach for the delivery of genes encoding therapeutic molecules that result in at least partial correction of neuropathologies provides a highly desirable method for treating a variety of neurodegenerative disorders, including SMA.

Thus in one embodiment, the invention is directed to a self-complementary adeno-associated virus (scAAV) vector comprising a polynucleotide encoding a protein that modulates motor function in a subject with a motor neuron disorder. In certain embodiments, the motor neuron disorder is selected from spinal muscular atrophy (SMA), amytrophic lateral sclerosis (ALS), spinal bulbar muscular atrophy, spinal cerebellar ataxia, primary lateral sclerosis (PLS), or traumatic spinal cord injury.

In additional embodiments, the polynucleotide present in the scAAV vector encodes a survival motor neuron (SMN) protein. In certain embodiments, the SMN protein is human SMN-1. In further embodiments, the SMN-1 comprises an amino acid sequence with at least 90% sequence identity to the sequence depicted in FIG. 9B. In additional embodiments, the SMN-1 comprises an amino acid sequence as depicted in FIG. 9B.

In yet further embodiments, the invention is directed to a recombinant AAV virion, comprising an scAAV vector as described above.

In additional embodiments, the invention is directed to a composition comprising a recombinant AAV virion as above and a pharmaceutically acceptable excipient.

In further embodiments, the invention is directed to a method of modulating motor function in a subject with a motor neuron disorder comprising administering a therapeutically effective amount of the composition above to cells of the subject. In certain embodiments, the composition is administered to cells in vitro to transduce the cells and the transduced cells are administered to the subject. In alternative embodiments, the composition is administered to cells in vivo.

In further embodiments, the invention is directed to a method of providing an SMN protein to a subject with spinal muscular atrophy (SMA) comprising administering a recombinant AAV virion comprising an AAV vector as described above to cells of a subject in need thereof. In certain embodiments the composition is administered to cells in vitro to transduce the cells and the transduced cells are administered to the subject. In alternative embodiments, the composition is administered to cells in vivo.

In each of the methods above, the composition can be administered via direct spinal cord injection. In other embodiments, the composition is administered via intracerebroventricular injection. In additional embodiments, the composition is administered into a cerebral lateral ventricle. In certain embodiments, the composition is administered into both cerebral lateral ventricles. In other embodiments, the composition is administered via both intracerebroventricular injection and direct spinal cord injection. In additional embodiments, the composition is administered by intrathecal injection.

These and other embodiments of the subject invention will readily occur to those of skill in the art in view of the disclosure herein.

BRIEF DESCRIPTION OF THE FIGURES

FIGS. 3A-3J show the sub-cellular distribution of hSMN protein and expression in motor neurons of the spinal cord in treated and untreated SMA mice. hSMN protein was abundantly detected in the cytoplasm of transduced cells (FIGS. 3A and 3B). Furthermore, hSMN protein was detected in the nucleus, as illustrated by the pair of gem-like structures (arrowhead) magnified in the inset (FIG. 3A). hSMN protein was also detected in the dendrites (FIGS. 3B and 3C) and axons (FIG. 3D) of neurons. hSMN protein was not detectable on the tissue sections from untreated SMA mice (FIG. 3E). Co-localization of hSMN protein (FIG. 3F) with mouse ChAT (FIG. 3G) showed that a subset of transduced cells were motor neurons (FIGS. 3H and 3I). The percentage of ChAT cells that were immuno-positive for hSMN protein was determined at 16 (white bars) and 58-66 (black bars) days (FIG. 3J). Values represent the mean±SEM.

FIGS. 6A-6F show the structure of the NMJ in muscles in treated and untreated SMA mice. The structure in the quadriceps, gastrocnemius, and intercostal was improved with gene therapy. Shown are the neuromuscular junction (NMJ) from the quadriceps of untreated SMA (FIG. 6A), treated SMA (FIG. 6B), and untreated wild type (FIG. 6C) mice at 16 days, and from treated SMA (FIG. 6D) and untreated wild type (FIG. 6E) mice at 58-66 days. The pre- and post-synaptic NMJ was labeled with a neurofilament antibody (green) and with α-bungarotoxin staining (red), respectively. The arrowhead in the main panel points to the NMJ that is highlighted in the insets below. At least 100 NMJs was randomly scored in each muscle per animal. A normal NMJ was defined as having a pre-synaptic terminus that did not exhibit the abnormal accumulation of neurofilament protein shown in FIG. 6A. Values in FIG. 6F represent the mean±SEM. Key: WT, untreated wild type; HET, untreated heterozygote; SMA, untreated knockout; AAV, AAVhSMN1-treated SMA mice; *, $p<0.05$; , $p<0.01$; *, $p<0.001$. Scale bars: 20 μm.

FIGS. 9A-9B (SEQ ID NOS:1 and 2) show the coding DNA sequence (FIG. 9A) and the corresponding amino acid sequence (FIG. 9B) of a representative human survival motor neuron (SMN1) gene.

FIG. 10A shows the percentage of mChAT immunopositive cells that co-localized with hSMN expression in the thoracic-lumbar region at 16 days post-injection. FIGS. 10B-10F show the average numbers of mChAT immunopositive cells in the lumbar (FIG. 10B), thoracic (FIG. 10C), and cervical (FIG. 10D) segments, and the average percentages of collapsed NMJs in the quadriceps (FIG. 10E) and intercostal (FIG. 10F) muscles at 16, 58-66 and 214-269 days. As a reference for FIGS. 10E and 10F, 75-90% of NMJ in the quadriceps and intercostal muscles of untreated SMA mice contained an aberrant collapsed structure at 16 days (see FIG. 6F). Key and n-values: SMA, untreated knockout (open bars, n=8 at 16 days), AAV, AAV8-hSMN (hatched bars, n=8 at 16 days, n=5 at 58-66 days); scAAV, scAAV8-hSMN (closed bars, n=5 at each time point); WT, untreated WT (checkered bars, n=8 at 16 days, n=5 each at 58-66 and 216-269 days). Values represent the mean±SEM. Statistical comparisons were performed with one-way ANOVA and Bonferroni multiple post hoc tests at 16 days (FIGS. 10B-10F). The unpaired two-tailed student t-test compared 1) the two vectors to each other at 16 days (FIG. 10A) and 58-66 days (FIGS. 10B-10D); 2) the relative number of ChAT cells in the 58-66 d and 214-269 d groups with scAAV8-hSMN treatment (FIGS. 10B-10D); 3) the relative number of abnormal NMJs between the age-matched untreated WT and scAAV8-hSMN-treated SMA mice at 214-269 days (E, F); *$p<0.05$, $p<0.01$, *$p<0.001$.

DETAILED DESCRIPTION OF THE INVENTION

Figure 1:
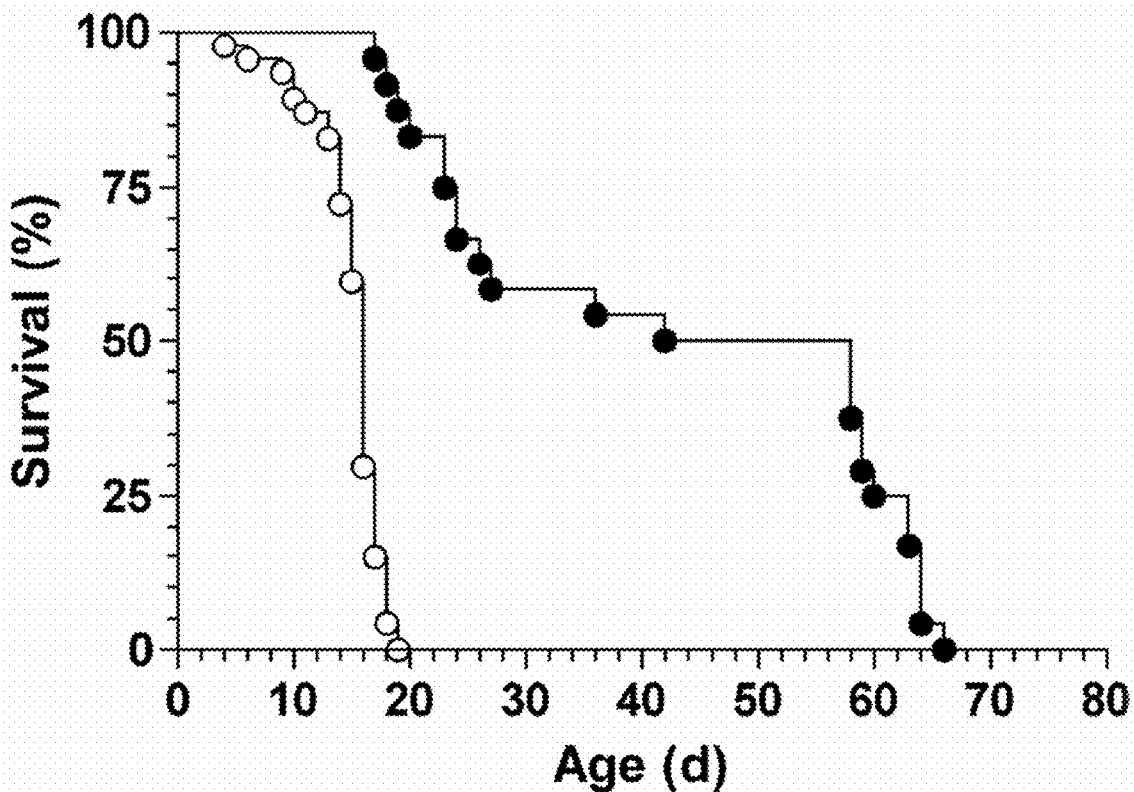
FIG. 1 shows survival of mice treated with AAVhSMN1 versus untreated SMA mice. Treatment with AAVhSMN1 increased survival in SMA mice. Untreated SMA mice (n=34, open circles) had a median life span of 15 days. SMA mice treated at P0 with AAVhSMN1 (n=24, closed circles) had a median lifespan of 50 days (p<0.0001), which was a +233% increase in longevity.

The practice of the present invention will employ, unless otherwise indicated, conventional methods of chemistry, biochemistry, recombinant DNA techniques and immunology, within the skill of the art. Such techniques are explained fully in the literature. See, e.g., *Fundamental Virology*, 2nd Edition, vol. I & II (B. N. Fields and D. M. Knipe, eds.); *Handbook of Experimental Immunology*, Vols. I-IV (D. M. Weir and C. C. Blackwell eds., Blackwell Scientific Publications); T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.).

All publications, patents and patent applications cited herein, whether supra or infra, are hereby incorporated by reference in their entirety.

1. Definitions

In describing the present invention, the following terms will be employed, and are intended to be defined as indicated below.

It must be noted that, as used in this specification and the appended claims, the singular forms "a", "an" and "the" include plural referents unless the content clearly dictates otherwise. Thus, for example, reference to "an interleukin receptor" includes a mixture of two or more such receptors, and the like.

The terms "polypeptide" and "protein," used interchangeably herein, or a nucleotide sequence encoding the same, refer to a protein or nucleotide sequence, respectively, that represents either a native sequence, a variant thereof or a fragment thereof. The full-length proteins, with or without the signal sequence, and fragments thereof, as well as proteins with modifications, such as deletions, additions and substitutions (either conservative or non-conservative in nature), to the native sequence, are intended for use herein, so long as the protein maintains the desired activity. These modifications may be deliberate, as through site-directed mutagenesis, or may be accidental, such as through mutations of hosts which produce the proteins or errors due to PCR amplification. Accordingly, active proteins substantially homologous to the parent sequence, e.g., proteins with 70 ... 80 ... 85 ... 90 ... 95 ... 98 ... 99% etc. identity that retain the desired activity of the native molecule, are contemplated for use herein.

A "native" polypeptide, such as a survival motor neuron (SMN) polypeptide, refers to a polypeptide having the same amino acid sequence as the corresponding molecule derived from nature. Such native sequences can be isolated from nature or can be produced by recombinant or synthetic means. The term "native" sequence specifically encompasses naturally-occurring truncated or secreted forms of the specific molecule (e.g., an extracellular domain sequence), naturally-occurring variant forms (e.g., alternatively spliced forms) and naturally-occurring allelic variants of the polypeptide. in various embodiments of the invention, the native molecules disclosed herein are mature or full-length native sequences comprising the full-length amino acids sequences shown in the accompanying figures. However, while some of the molecules disclosed in the accompanying figures begin with methionine residues designated as amino acid position 1 in the figures, other methionine residues located either upstream or downstream from amino acid position 1 in the figures may be employed as the starting amino acid residue for the particular molecule. Alternatively, depending on the expression system used, the molecules described herein may lack an N-terminal methionine.

By "variant" is meant an active polypeptide as defined herein having at least about 80% amino acid sequence identity with the corresponding full-length native sequence, a polypeptide lacking the signal peptide, an extracellular domain of a polypeptide, with or without a signal peptide, or any other fragment of a full-length polypeptide sequence as disclosed herein. Such polypeptide variants include, for instance, polypeptides wherein one or more amino acid residues are added, or deleted, at the N- and/or C-terminus of the fill-length native amino acid sequence. Ordinarily, a variant will have at least about 80% amino acid sequence identity, alternatively at least about 81% amino acid sequence identity, alternatively at least about 82% amino acid sequence identity, alternatively at least about 83% amino acid sequence identity, alternatively at least about 84% amino acid sequence identity, alternatively at least about 85% amino acid sequence identity, alternatively at least about 86% amino acid sequence identity, alternatively at least about 87% amino acid sequence identity, alternatively at least about 88% amino acid sequence identity, alternatively at least about 89% amino acid sequence identity, alternatively at least about 90% amino acid sequence identity, alternatively at least about 91% amino acid sequence identity, alternatively at least about 92% amino acid sequence identity, alternatively at least about 93% amino acid sequence identity, alternatively at least about 94% amino acid sequence identity, alternatively at least about 95% amino acid sequence identity, alternatively at least about 96% amino acid sequence identity, alternatively at least about 97% amino acid sequence identity, alternatively at least about 98% amino acid sequence identity and alternatively at least about 99% amino acid sequence identity to the corresponding full-length native sequence. Ordinarily, variant polypeptides are at least about 10 amino acids in length, such as at least about 20 amino acids in length, e.g., at least about 30 amino acids in length, alternatively at least about 40 amino acids in length, alternatively at least about 50 amino acids in length, alternatively at least about 60 amino acids in length, alternatively at least about 70 amino acids in length, alternatively at least about 80 amino acids in length, alternatively at least about 90 amino acids in length, alternatively at least about 100 amino acids in length, alternatively at least about 150 amino acids in length, alternatively at least about 200 amino acids in length, alternatively at least about 300 amino acids in length, or more.

Particularly preferred variants include substitutions that are conservative in nature, i.e., those substitutions that take place within a family of amino acids that are related in their side chains. Specifically, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine threonine, tyrosine. Phenylalanine, tryptophan, and tyrosine are sometimes classified as aromatic amino acids. For example, it is reasonably predictable that an isolated replacement of leucine with isoleucine or valine, an aspartate with a glutamate, a threonine with a serine, or a similar conservative replacement of an amino acid with a structurally related amino acid, will not have a major effect on the biological activity. For example, the polypeptide of interest may include up to about 5-10 conservative or non-conservative amino acid substitutions; or even up to about 15-25 or 50 conservative or non-conservative amino acid substitutions, or any number between 5-50, so long as the desired function of the molecule remains intact.

"Homology" refers to the percent identity between two polynucleotide or two polypeptide moieties. Two DNA, or two polypeptide sequences are "substantially homologous" to each other when the sequences exhibit at least about 50%, preferably at least about 75%, more preferably at least about 80%-85%, preferably at least about 90%, and most preferably at least about 95%-98% sequence identity over a defined length of the molecules. As used herein, substantially homologous also refers to sequences showing complete identity to the specified DNA or polypeptide sequence.

In general, "identity" refers to an exact nucleotide-to-nucleotide or amino acid-to-amino acid correspondence of two polynucleotides or polypeptide sequences, respectively. Percent identity can be determined by a direct comparison of the sequence information between two molecules by aligning the sequences, counting the exact number of matches between the two aligned sequences, dividing by the length of the shorter sequence, and multiplying the result by 100. Readily available computer programs can be used to aid in the analysis, such as ALIGN, Dayhoff, M. O. in *Atlas of Protein Sequence and Structure* M. O. Dayhoff ed., 5 Suppl. 3:353-358, National Biomedical Research Foundation, Washington, DC, which adapts the local homology algorithm of Smith and Waterman *Advances in Appl. Math.* 2:482-489, 1981 for peptide analysis. Programs for determining nucleotide sequence identity are available in the Wisconsin Sequence Analysis Package, Version 8 (available from Genetics Computer Group, Madison, WI) for example, the BES FIT, FASTA and GAP programs, which also rely on the Smith and Waterman algorithm. These programs are readily utilized with the default parameters recommended by the manufacturer and described in the Wisconsin Sequence Analysis Package referred to above. For example, percent identity of a particular nucleotide sequence to a reference sequence can be determined using the homology algorithm of Smith and Waterman with a default scoring table and a gap penalty of six nucleotide positions.

Another method of establishing percent identity in the context of the present invention is to use the MPSRCH package of programs copyrighted by the University of Edinburgh, developed by John F. Collins and Shane S.

Sturrok, and distributed by IntelliGenetics, Inc. (Mountain View, CA). From this suite of packages the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+ PDB+GenBank CDS translations+Swiss protein+Spupdate+ PIR. Details of these programs are well known in the art.

Alternatively, homology can be determined by hybridization of polynucleotides under conditions which form stable duplexes between homologous regions, followed by digestion with single-stranded-specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *DNA Cloning*, supra; *Nucleic Acid Hybridization*, supra.

By the term "degenerate variant" is intended a polynucleotide containing changes in the nucleic acid sequence thereof, that encodes a polypeptide having the same amino acid sequence as the polypeptide encoded by the polynucleotide from which the degenerate variant is derived.

A "coding sequence" or a sequence which "encodes" a selected polypeptide, is a nucleic acid molecule which is transcribed (in the case of DNA) and translated (in the case of mRNA) into a polypeptide in vivo when placed under the control of appropriate regulatory sequences. The boundaries of the coding sequence are determined by a start codon at the 5' (amino) terminus and a translation stop codon at the 3' (carboxy) terminus. A transcription termination sequence may be located 3' to the coding sequence.

By "vector" is meant any genetic element, such as a plasmid, phage, transposon, cosmid, chromosome, virus, virion, etc., which is capable of replication when associated with the proper control elements and which can transfer gene sequences to cells. Thus, the term includes cloning and expression vehicles, as well as viral vectors.

By "recombinant vector" is meant a vector that includes a heterologous nucleic acid sequence which is capable of expression in vivo.

By "recombinant virus" is meant a virus that has been genetically altered, e.g., by the addition or insertion of a heterologous nucleic acid construct into the particle.

The term "transgene" refers to a polynucleotide that is introduced into a cell and is capable of being transcribed into RNA and optionally, translated and/or expressed under appropriate conditions. In one aspect, it confers a desired property to a cell into which it was introduced, or otherwise leads to a desired therapeutic or diagnostic outcome.

The terms "genome particles (gp)," or "genome equivalents," as used in reference to a viral titer, refer to the number of virions containing the recombinant AAV DNA genome, regardless of infectivity or functionality. The number of genome particles in a particular vector preparation can be measured by procedures such as described in the Examples herein, or for example, in Clark et al., *Hum. Gene Ther.* (1999) 10:1031-1039; and Veldwijk et al., *Mol. Ther.* (2002) 6:272-278.

The terms "infection unit (iu)," "infectious particle," or "replication unit," as used in reference to a viral titer, refer to the number of infectious recombinant AAV vector particles as measured by the infectious center assay, also known as replication center assay, as described, for example, in McLaughlin et al., *J. Virol.* (1988) 62:1963-1973.

The term "transducing unit (tu)" as used in reference to a viral titer, refers to the number of infectious recombinant AAV vector particles that result in the production of a functional transgene product as measured in functional assays such as described in Examples herein, or for example, in Xiao et al., *Exp. Neurobiol.* (1997) 144:1 13-124; or in Fisher et al., *J. Virol.* (1996) 70:520-532 (LFU assay).

The term "transfection" is used to refer to the uptake of foreign DNA by a cell, and a cell has been "transfected" when exogenous DNA has been introduced inside the cell membrane. A number of transfection techniques are generally known in the art. See, e.g., Graham et al. (1973) *Virology*, 52:456, Sambrook et al, (1989) *Molecular Cloning, a laboratory manual*, Cold Spring Harbor Laboratories, New York, Davis et al. (1986) *Basic Methods in Molecular Biology*, Elsevier, and Chu et al. (1981) *Gene* 13:197. Such techniques can be used to introduce one or more exogenous DNA moieties into suitable host cells.

The term "heterologous" as it relates to nucleic acid sequences such as coding sequences and control sequences, denotes sequences that are not normally joined together, and/or are not normally associated with a particular cell. Thus, a "heterologous" region of a nucleic acid construct or a vector is a segment of nucleic acid within or attached to another nucleic acid molecule that is not found in association with the other molecule in nature. For example, a heterologous region of a nucleic acid construct could include a coding sequence flanked by sequences not found in association with the coding sequence in nature. Another example of a heterologous coding sequence is a construct where the coding sequence itself is not found in nature (e.g., synthetic sequences having codons different from the native gene). Similarly, a cell transformed with a construct which is not normally present in the cell would be considered heterologous for purposes of this invention. Allelic variation or naturally occurring mutational events do not give rise to heterologous DNA, as used herein.

A "nucleic acid" sequence refers to a DNA or RNA sequence. The term captures sequences that include any of the known base analogues of DNA and RNA such as, but not limited to 4-acetylcytosine, 8-hydroxy-N6-methyladenosine, aziridinylcytosine, pseudoisocytosine, 5-(carboxyhydroxyl-methyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methyl-cytosine, 5-methylcytosine, N6-methyladenine, 7-methylguanine, 5-methylaminomethyluracil, 5-methoxyamino-methyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, -uracil-5-oxyacetic acid methylester, uracil-5-oxyacetic acid, pseudouracil, queosine, 2-thiocytosine, and 2,6-diaminopurine.

The term DNA "control sequences" refers collectively to promoter sequences, polyadenylation signals, transcription termination sequences, upstream regulatory domains, origins of replication, internal ribosome entry sites ("IRES"), enhancers, and the like, which collectively provide for the replication, transcription and translation of a coding sequence in a recipient cell. Not all of these control sequences need always be present so long as the selected coding sequence is capable of being replicated, transcribed and translated in an appropriate host cell.

The term "promoter" is used herein in its ordinary sense to refer to a nucleotide region comprising a DNA regulatory sequence, wherein the regulatory sequence is derived from a gene which is capable of binding RNA polymerase and initiating transcription of a downstream (3'-direction) coding sequence. Transcription promoters can include "inducible promoters" (where expression of a polynucleotide sequence operably linked to the promoter is induced by an analyte, cofactor, regulatory protein, etc.), "repressible promoters" (where expression of a polynucleotide sequence operably linked to the promoter is induced by an analyte, cofactor, regulatory protein, etc.), and "constitutive promoters".

"Operably linked" refers to an arrangement of elements wherein the components so described are configured so as to perform their usual function. Thus, control sequences operably linked to a coding sequence are capable of effecting the expression of the coding sequence. The control sequences need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

The term "nervous system" includes both the central nervous system and the peripheral nervous system. The term "central nervous system" or "CNS" includes all cells and tissue of the brain and spinal cord of a vertebrate. The term "peripheral nervous system" refers to all cells and tissue of the portion of the nervous system outside the brain and spinal cord. Thus, the term "nervous system" includes, but is not limited to, neuronal cells, glial cells, astrocytes, cells in the cerebrospinal fluid (CSF), cells in the interstitial spaces, cells in the protective coverings of the spinal cord, epidural cells (i.e., cells outside of the dura mater), cells in non-neural tissues adjacent to or in contact with or innervated by neural tissue, cells in the epineurium, perineurium, endoneurium, funiculi, fasciculi, and the like.

"Active" or "activity" for purposes of the present invention refers to forms of a therapeutic protein which retain a biological activity of the corresponding native or naturally occurring polypeptide. The activity may be greater than, equal to, or less than that observed with the corresponding native or naturally occurring polypeptide.

By "isolated" when referring to a nucleotide sequence, is meant that the indicated molecule is present in the substantial absence of other biological macromolecules of the same type. Thus, an "isolated nucleic acid molecule which encodes a particular polypeptide" refers to a nucleic acid molecule which is substantially free of other nucleic acid molecules that do not encode the subject polypeptide; however, the molecule may include some additional bases or moieties which do not deleteriously affect the basic characteristics of the composition.

For the purpose of describing the relative position of nucleotide sequences in a particular nucleic acid molecule throughout the instant application, such as when a particular nucleotide sequence is described as being situated "upstream," "downstream," "3-prime (3')" or "5-prime (5')" relative to another sequence, it is to be understood that it is the position of the sequences in the "sense" or "coding" strand of a DNA molecule that is being referred to as is conventional in the art.

The term "about", particularly in reference to a given quantity, is meant to encompass deviations of plus or minus five percent.

The terms "subject", "individual" or "patient" are used interchangeably herein and refer to a vertebrate, preferably a mammal. Mammals include, but are not limited to, murines, rodents, simians, humans, farm animals, sport animals and pets.

The term "modulate" as used herein means to vary the amount or intensity of an effect or outcome, e.g., to enhance, augment, diminish, reduce or eliminate.

As used herein, the term "ameliorate" is synonymous with "alleviate" and means to reduce or lighten. For example, one may ameliorate the symptoms of a disease or disorder by making the disease or symptoms of the disease less severe.

The terms "therapeutic," "effective amount" or "therapeutically effective amount" of a composition or agent, as provided herein, refer to a sufficient amount of the composition or agent to provide the desired response, such as the prevention, delay of onset or amelioration of symptoms in a subject or an attainment of a desired biological outcome, such as correction of neuropathology, e.g., cellular pathology associated with a motor neuronal disease such as spinal muscular atrophy (SMA). The term "therapeutic correction" refers to that degree of correction that results in prevention or delay of onset or amelioration of symptoms in a subject. The exact amount required will vary from subject to subject, depending on the species, age, and general condition of the subject, the severity of the condition being treated, and the particular macromolecule of interest, mode of administration, and the like. An appropriate "effective" amount in any individual case may be determined by one of ordinary skill in the art using routine experimentation.

"Treatment" or "treating" a particular disease includes: (1) preventing the disease, i.e. preventing the development of the disease or causing the disease to occur with less intensity in a subject that may be exposed to or predisposed to the disease but does not yet experience or display symptoms of the disease, (2) inhibiting the disease, i.e., arresting the development or reversing the disease state, or (3) relieving symptoms of the disease i.e., decreasing the number of symptoms experienced by the subject, as well as changing the cellular pathology associated with the disease.

2. Modes of Carrying Out the Invention

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of methods and materials similar or equivalent to those described herein can be used in the practice of the present invention, the preferred materials and methods are described herein.

Central to the present invention is the discovery that delivery of rAAV virions containing the human survival motor neuron 1 (hSMN1) cDNA to the CNS of an aggressive mouse model of spinal muscular atrophy (SMA), produced expression of SMN1 throughout the spinal cord. Treated SMA mice contained a higher number of motor neurons compared to untreated, age-matched mutants. In addition, the evaluation of myofiber size demonstrated that the size of individual myofibers from a variety of muscle groups in treated SMA mice approximated those observed in wild-type mice. Furthermore, the structure of the neuromuscular junction (NMJ) in treated SMA mice was similar to wild-type mice, which was in contrast to untreated SMA that showed abnormal accumulation of neurofilament protein at the presynaptic termini. Treated SMA mice also displayed significant improvements on a battery of behavioral tests suggesting that the NMJ was functional. Importantly, recombinant AAV treated mice had a significantly increased lifespan as compared to their untreated counterparts. SMA mice treated with a self-complementary rAAV vector also displayed a remarkable improvement in median survival, even as compared to treatment with conventional, non-self-complementary rAAV vectors.

These results demonstrate that CNS-directed, AAV-mediated SMN1 gene augmentation is highly efficacious in addressing both the neuronal and muscular pathologies of SMA and evidence the utility of viral gene therapy as a therapeutic strategy for treating and preventing neuronal and muscular pathologies, such as SMA, as well as other diseases that affect motor function. The gene therapy techniques described herein can be used alone, or in conjunction with traditional drugs.

In order to further an understanding of the invention, a more detailed discussion is provided below regarding motor neuron pathologies and therapeutic molecules, as well as various gene delivery methods for use with the present invention.

Motor Neuron Pathologies and Therapeutic Molecules

The subject invention provides compositions and methods to modulate, correct or augment motor function in a subject afflicted with a motor neuron disorder or with motor neuronal damage. For the purpose of illustration only, the subject may suffer from one or more of spinal muscular atrophy (SMA), amytrophic lateral sclerosis (ALS), spinal bulbar muscular atrophy, spinal cerebellar ataxia, primary lateral sclerosis (PLS), or traumatic spinal cord injury. Without being bound by a particular theory, the pathology associated with motor neuron damage may include motor neuron degeneration, gliosis, neurofilament abnormalities, loss of myelinated fibers in corticospinal tracts and ventral roots. For example, two types of onset have been recognized—bulbar onset, which affects the upper motor neurons (cortex and brainstem motor neurons), affects the facial muscles, speech, and swallowing; and limb onset, which affects the lower motor neurons (spinal cord motor neurons), is reflected by spasticity, generalized weakness, muscular atrophy, paralysis, and respiratory failure. In ALS, subjects have both bulbar and limb onset. In PLS, subjects just have bulbar onset.

Thus, in certain embodiments, the subject is provided with rAAV constructs that encode a biologically active molecule, the expression of which in the CNS results in at least partial correction of neuropathology and/or stabilization of disease progression, such as the prevention, delay of onset or amelioration of symptoms in a subject or an attainment of a desired biological outcome, including for example, a change in the cellular pathology associated with a motor neuronal disease described above.

By way of example, the transgene present in the rAAV construct may be, but is not limited to, survival motor neuron protein (via the SMN1 gene or SMN2 gene), insulin growth factor-1 (IGF-1), calbindin D28, parvalbumin, HIF1-alpha, SIRT-2, VEGF such as VEGF165, CNTF (Ciliary neurotrophic factor), sonic hedgehog (shh), erythropoietin (EPO), lysyl oxidase (LOX), progranulin, prolactin, ghrelin, neuroserpin, angiogenin, and placenta lactogen.

The molecular basis of SMA, an autosomal recessive neuromuscular disorder, is the homozygous loss of the survival motor neuron gene 1 (SMN1), which may also be known as SMN Telomeric. A nearly identical copy of the SMN1 gene, called SMN2, which may also be known as SMN Centromeric, is found in humans and modulates the disease severity. Expression of the normal SMN1 gene results solely in expression of survival motor neuron (SMN) protein. Expression of the SMN2 gene results in approximately 10-20% of the SMN protein and 80-90% of an unstable/non-functional SMNdelta7 protein. Only 10% of SMN2 transcripts encode a functional full-length protein identical to SMN1. This functional difference between both genes results from a translationally silent mutation that, however, disrupts an exonic splicing enhancer causing exon 7 skipping in most SMN2 transcripts. SMN protein plays a well-established role in assembly of the spliceosome and may also mediate mRNA trafficking in the axon and nerve terminus of neurons.

The nucleotide and amino acid sequences of various SMN1 molecules and SMN proteins are known. See, for example, FIGS. 9A-9B; NCBI accession numbers NM_00344 (human), NP_000335 (human), NM_11420 (mouse), EU_791616 (porcine), NM_001131470 (orangutan), NM_131191 (zebrafish), BC062404 (rat), NM_001009328 (cat), NM_001003226 (dog), NM_175701 (cow). Similarly, various SMN2 sequences are known. See, e.g., NCBI accession numbers NM_022876, NM_022877, NM_017411, NG_008728, BC_000908, BC070242, DQ185039 (all human).

Insulin-like growth factor 1 (IGF-I) is a therapeutic protein for the treatment of neurodegenerative disorders, including motor neuron disorders, due to its many actions at different levels of neuraxis (see Dore et al., *Trends Neurosci* (1997) 20:326-331). For example, in the brain it is thought to reduce both neuronal and glial apoptosis, protect neurons against toxicity induced by iron, colchicine, calcium destabilizers, peroxides, and cytokines. It also appears to modulate the release of neurotransmitters acetylcholine and glutamate and induce the expression of neurofilament, tublin, and myelin basic protein. In the spinal cord, IGF-I is believed to modulate ChAT activity and attenuate loss of cholinergic phenotype, enhance motor neuron sprouting, increase myelination, inhibit demyelination, stimulate motor neuron proliferation and differentiation from precursor cells, and promote Schwann cell division, maturation, and growth. In the muscle, IGF-I appears to induce acetylcholine receptor cluster formation at the neuromuscular junction and increase neuromuscular function and muscle strength.

The IGF-1 gene has a complex structure, which is well-known in the art. It has at least two alternatively spliced mRNA products arising from the gene transcript. There is a 153 amino acid peptide, known by several names including IGF-IA or IGF-IEa, and a 195 amino acid peptide, known by several names including IGF-IB or IGF-IEb. The Eb form is also be known as Ec in humans. The mature form of IGF-I is a 70 amino acid polypeptide. Both IGF-IEa and IGF-IEb contain the 70 amino acid mature peptide, but differ in the sequence and length of their carboxyl-terminal extensions.

The IGF-1 proteins, as well as the peptide sequences of IGF-IEa and IGF-IEb are known and described in, e.g., International Publication No. WO 2007/146046, incorporated herein by reference in its entirety. The genomic and functional cDNAs of human IGF-I, as well as additional information regarding the IGF-I gene and its products, are available at Unigene Accession No. NM_000618.

Calbindin D28K (also referred to as calbindin D28) and parvalbumin are calcium-binding proteins believed to be involved in calcium buffering. Without being bound by a particular theory, calcium homeostasis appears to be altered in subjects with motor neuron disorders (e.g., ALS) and low levels of calbindin-D28K and/or parvalbumin may increase the vulnerability of motor neurons by reducing their ability to handle an increased calcium load. This reduction may lead to cell injury and eventual motor neuron death. Further evidence suggests that neurons rich in calcium-binding proteins, such as calbindin D28K and parvalbumin, are resistant to degeneration.

HIF-I is a heterodimeric protein composed of two subunits: (i) a constitutively expressed β subunit also known as aryl hydrocarbon nuclear translocator (ARNT) (which is shared by other related transcription factors (e.g., the dioxin/aryl hydrocarbon receptor (DR/AhR)); and (ii) an α subunit (see, e.g., International publication No. WO 96/39426, describing the recent affinity purification and molecular cloning of HIF-Iα. Both subunits are members of the basic helix-loop-helix (bHLH)-PAS family of transcription factors. These domains regulate DNA binding and dimerization. The transactivation domain resides in the C-terminus of the protein. The basic region consists of approximately 15 predominantly basic amino acids responsible for direct DNA binding. This region is adjacent to two amphipathic α helices, separated by a loop of variable length, which forms the primary dimerization interface between family members (Moore, et al., *Proc. Natl. Acad. Sci. USA* (2000) 97:10436-10441). The PAS domain encompasses 200-300 amino acids containing two loosely conserved, largely hydrophobic regions approximately 50 amino acids, designated PAS A and PAS B. The HIF-Iα subunit is unstable during normoxic conditions, overexpression of this subunit in cultured cells under normal oxygen levels is capable of inducing expression of genes normally induced by hypoxia. Replacement of the C terminal (or transactivation) region of the hypoxia-inducible factor protein with a strong transactivation domain from a transcriptional activator protein such as, for example, Herpes Simplex Virus (HSV) VP16, NFκB or yeast transcription factors GAL4 and GCN4, is designed to stabilize the protein under normoxic conditions and provide strong, constitutive, transcriptional activation. See, e.g., International Publication No. WO 2008/042420 for a description and sequence of a representative stabilized hypoxia-inducible factor protein that is a hybrid/chimeric fusion protein consisting of the DNA-binding and dimerization domains from HIF-Iα and the transactivation domain from the HSV VP16 protein, incorporated herein by reference in its entirety. See, also, U.S. Pat. Nos. 6,432,927 and 7,053,062 for a description of a constitutively stable hybrid HIF-Iα, both of which are incorporated by reference herein in their entirety, Members of the vascular endothelial growth factor (VEGF) family are among the most powerful modulators of vascular biology. They regulate vasculogenesis, angiogenesis, and vascular maintenance. Four different molecular variants of VEGF have been described. The 165 amino acid variant is the predominant molecular form found in normal cells and tissues. A less abundant, shorter form with a deletion of 44 amino acids between positions 116 and 159 ($VEGF_{121}$), a longer form with an insertion of 24 basic residues in position 116 ($VEGF_{189}$), and another longer form with an insertion of 41 amino acids ($VEGF_{206}$), which includes the 24 amino acid insertion found in $VEGF_{189}$, are also known. $VEGF_{121}$ and $VEGF_{165}$ are soluble proteins. $VEGF_{189}$ and $VEGF_{206}$ appear to be mostly cell-associated. All of the versions of VEGF are biologically active. See, e.g., Tischer et al., *J. Biol. Chem.* (1991) 266:11947-11954, describing the sequence of $VEGF_{165}$ (see, also, GenBank Accession no. AB021221), $VEGF_{121}$ (see, also, GenBank Accession no. AF214570) and $VEGF_{189}$; and Houck et al., *Mol. Endocrinol*, (1991) 5:1806-1814, describing the sequence of $VEGF_{206}$.

CNTF (Ciliary neurotrophic factor) is a neurocytokine expressed by glial cells in peripheral nerves and the central nervous system. CNTF is generally recognized for its function in support and survival of non-neuronal and neuronal cell types. See e.g., Vergara, C and Ramirez, B; *Brain Res, Brain Res. Rev.* (2004) 47: 161-73.

Sonic hedgehog (Shh) controls important developmental processes, including neuronal and glial cell survival.

Erythropoietin (EPO) is a principal regulator of erythroid progenitor cells. However, it is functionally expressed in the nervous system and has been reported to have a neuroprotective effects. See e.g., Bartesaghi, S., 2005. Neurotoxicology, 26:923-8. Genes encoding human and other mammalian EPO have been cloned, sequenced and expressed, and show a high degree of sequence homology in the coding region across species. Wen et al., *Blood* (1993) 82:1507-1516. The sequence of the gene encoding native human EPO, as well as methods of obtaining the same, are described in, e.g., U.S. Pat. Nos. 4,954,437 and 4,703,008, incorporated herein by reference in their entirety, as well as in Jacobs et al. (1985) *Nature* 313:806-810; Lin et al. (1985) *Proc. Natl. Acad. Sci. USA* 82:7580; International Publication Number WO 85/02610; and European Patent Publication Number 232,034 B1. In addition, the sequences of the genes encoding native feline, canine and porcine EPO are known and readily available (GenBank Accession Nos.: L10606; L13027; and L10607, respectively), and the sequence of the gene encoding monkey (*Macaca mulatta*) is also known and available (GenBank Accession No.: L10609).

Lysyl oxidase (LOX) oxidizes the side chain of peptidyl lysine thereby converting certain lysine residues to alpha-aminoadipic-delta-semialdehyde. This is a post-translational change that, for example, enables the covalent cross-linking of the component chains of collagen and elastin. It stabilizes the fibrous deposits of these proteins in the extracellular matrix. LOX can also oxidize lysine within a variety of cationic proteins, which suggests that its functions are broader than stabilization or the extracellular matrix. LOX is synthesized as a preprotein; it emerges from the cell as proLOX and is processed proteolytically to the active enzyme. See e.g., Lucero, H A and Kagan, H M, *Cell Mol. Life Sci.* (2006) 63:2304-2316.

Progranulin (PGRN) is a pleitropic protein. Mutations in the gene cause frontotemporal lobar degeneration. PGRN in the CNS is expressed by microglia and neurons and plays a role in brain development. PGRN is also involved in multiple "tissue modeling" processes including development, wound repair and tumorogenesis. PGRN is converted to Granulin (GRN) by elastase enzymes. While progranulin has trophic properties, GRNs are more akin to inflammatory mediators. Gene expression studies from animal models of CNS disease show a differential increase in PRGN combined with microglial activation and inflammation. Increase in PGRN expression may be closely related to microglial activation and neuroinflammation. Moreover, PGRN expression is increased in activated microglia in many neurodegenerative diseases including motor neuron disease and Alzheimer's disease. Studies have identified mutations in PGRN as a cause of neurodegenerative disease and indicate the importance of PGRN function for neuronal survival.

Oligodendrocytes, the myelinating cells of the CNS, continue to be generated by oligodendrocyte precursor cells (OPCs) throughout adulthood and are required for the intrinsic repair of myelin damage in the adult CNS. The physiological events that modulate OPC proliferation and the generation of new myelinating oligodendrocytes in the adult CNS are largely known. Recently it has been reported that patients with Multiple Sclerosis (MS), a demyelinating disease, have a reduced relapse rate during the third trimester of pregnancy suggesting that hormones influence oligodendrocyte generation. Remission in MS patients is correlated with a decrease in the number and size of active white matter lesions. Pregnancy in mice results in an increase in the generation of new oligodendrocytes and the number of myelinated axons within the maternal CNS (Gregg et al., *J. Neurosci.* (2007) 27:1812-1823). Prolactin, a hormone that plateaus during the final stage of pregnancy, has been shown to regulate OPC proliferation during pregnancy and promote white matter repair in virgin female mice (Gregg et al., *J. Neurosci.* (2007) 27:1812-1823).

Human placenta lactogen (hPL), a hormone that also peaks during the third trimester of pregnancy may have a similar influence on oligodendrocyte generation. hPL has a number of biological activities that are qualitatively similar to human growth hormone (hGH) and prolactin and appears to be a major regulator of IGF-I production. Both hGH and IGF-1 have been shown to be stimulators of myelination in the adult CNS (Carson et al., *Neuron* (1993) 10:729-740; Peltwon et al., *Neurology* (1977) 27:282-288). Therefore, the treatment of CNS diseases involving demyelination such as MS, ALS, stroke and spinal cord injury may benefit from PRL- or hPL-based therapies, such as by the intraventricular injection of an rhPRL or hPL expressing viral vector.

Ghrelin is a gastric hormone that is a mediator of growth hormone release. See e.g. Wu, et al., *Ann. Surg.* (2004) 239:464.

Neuroserpin is a serpin protease inhibitor family member. In certain CNS conditions, neuroserpin can play a neuroprotective role potentially through the blockage of the effects of tPA. See, e.g., Galliciotti, G and Sonderegger, P, *Front Biosci* (2006) 11:33; Simonin, et al., (2006) 26:10614; Miranda, E and Lomas, D A, *Cell Mol Life Sci* (2006) 63:709.

Angiogenin is a member of the RNAse superfamily. It is a normal constituent of circulation but has also been implicated as a risk factor in motor neuron disorders.

In certain compositions and methods of the invention, more than one transgene encoding more than one of the therapeutic molecules described above can be delivered, wherein each transgene is operably linked to a promoter to enable the expression of the trangenes from a single AAV vector. In additional methods, the transgenes may be operably linked to the same promoter. Each transgene encodes a biologically active molecule, expression of which in the CNS results in at least partial correction of neuropathology. Additionally, in cases where more than one transgene is delivered, the transgenes may be delivered via more than one AAV vector, wherein each AAV vector comprises a transgene operably linked to a promoter.

The native molecules, as well as active fragments and analogs thereof, which retain the desired biological activity, as measured in any of the various assays and animal models including those described further herein, are intended for use with the present invention.

Polynucleotides encoding the desired protein for use with the present invention can be made using standard techniques of molecular biology. For example, polynucleotide sequences coding for the above-described molecules can be obtained using recombinant methods, such as by screening cDNA and genomic libraries from cells expressing the gene, or by deriving the gene from a vector known to include the same. The gene of interest can also be produced synthetically, rather than cloned, based on the known sequences. The molecules can be designed with appropriate codons for the particular sequence. The complete sequence is then assembled from overlapping oligonucleotides prepared by standard methods and assembled into a complete coding sequence. See, e.g., Edge, *Nature* (1981) 292:756; Nambair et al., *Science* (1984) 223:1299; and Jay et al., *J. Biol. Chem.* (1984) 259:6311.

Thus, particular nucleotide sequences can be obtained from vectors harboring the desired sequences or synthesized completely or in part using various oligonucleotide synthesis techniques known in the art, such as site-directed mutagenesis and polymerase chain reaction (PCR) techniques where appropriate. See, e.g., Sambrook, supra. One method of obtaining nucleotide sequences encoding the desired sequences is by annealing complementary sets of overlapping synthetic oligonucleotides produced in a conventional, automated polynucleotide synthesizer, followed by ligation with an appropriate DNA ligase and amplification of the ligated nucleotide sequence via PCR. See, e.g., Jayaraman et al., *Proc. Natl. Acad. Sci. USA* (1991) 88:4084-4088. Additionally, oligonucleotide-directed synthesis (Jones et al., *Nature* (1986) 54:75-82), oligonucleotide directed mutagenesis of preexisting nucleotide regions (Riechmann et al., *Nature* (1988) 332:323-327 and Verhoeyen et al., *Science* (1988) 239:1534-1536), and enzymatic filling-in of gapped oligonucleotides using $T_4$ DNA polymerase (Queen et al., *Proc. Natl. Acad. Sci. USA* (1989) 86:10029-10033) can be used to provide molecules for use in the subject methods.

Once produced, the constructs are delivered using recombinant viral vectors as described further below.

AAV Gene Delivery Techniques

The constructs described above, are delivered to the subject in question using any of several rAAV gene delivery techniques. Several AAV-mediated methods for gene delivery are known in the art. As described further below, genes can be delivered either directly to the subject or, alternatively, delivered ex vivo, to appropriate cells, such as cells derived from the subject, and the cells reimplanted in the subject.

Various AAV vector systems have been developed for gene delivery. AAV vectors can be readily constructed using techniques well known in the art. See, e.g., U.S. Pat. Nos. 5,173,414 and 5,139,941; International Publication Nos. WO 92/01070 (published 23 Jan. 1992) and WO 93/03769 (published 4 Mar. 1993); Lebkowski et al., *Molec. Cell. Biol.* (1988) 8:3988-3996; Vincent et al., *Vaccines* 90 (1990) (Cold Spring Harbor Laboratory Press); Carter, B. J. *Current Opinion in Biotechnology* (1992) 3:533-539; Muzyczka, N. *Current Topics in Microbiol. and Immunol.* (1992) 158:97-

129; Kotin, R. M. *Human Gene Therapy* (1994) 5:793-801; Shelling and Smith, *Gene Therapy* (1994) 1:165-169; and Zhou et al., *J. Exp. Med.* (1994) 179:1867-1875. AAV vector systems are also described in further detail below.

The AAV genome is a linear, single-stranded DNA molecule containing about 4681 nucleotides. The AAV genome generally comprises an internal, nonrepeating genome flanked on each end by inverted terminal repeats (ITRs). The ITRs are approximately 145 base pairs (bp) in length. The ITRs have multiple functions, including providing origins of DNA replication, and packaging signals for the viral genome. The internal nonrepeated portion of the genome includes two large open reading frames, known as the AAV replication (rep) and capsid (cap) genes. The rep and cap genes code for viral proteins that allow the virus to replicate and package into a virion. In particular, a family of at least four viral proteins are expressed from the AAV rep region, Rep 78, Rep 68, Rep 52, and Rep 40, named according to their apparent molecular weight. The AAV cap region encodes at least three proteins, VP1, VP2, and VP3.

AAV has been engineered to deliver genes of interest by deleting the internal nonrepeating portion of the AAV genome (i.e., the rep and cap genes) and inserting a heterologous gene between the ITRs. The heterologous gene is typically functionally linked to a heterologous promoter (constitutive, cell-specific, or inducible) capable of driving gene expression in the patient's target cells under appropriate conditions. Examples of each type of promoter are well-known in the art. Termination signals, such as polyadenylation sites, can also be included.

AAV is a helper-dependent virus; that is, it requires coinfection with a helper virus (e.g., adenovirus, herpesvirus or vaccinia), in order to form AAV virions. In the absence of coinfection with a helper virus, AAV establishes a latent state in which the viral genome inserts into a host cell chromosome, but infectious virions are not produced. Subsequent infection by a helper virus "rescues" the integrated genome, allowing it to replicate and package its genome into an infectious AAV virion. While AAV can infect cells from different species, the helper virus must be of the same species as the host cell. Thus, for example, human AAV will replicate in canine cells coinfected with a canine adenovirus.

Recombinant AAV virions comprising the gene of interest may be produced using a variety of art-recognized techniques described more fully below. Wild-type AAV and helper viruses may be used to provide the necessary replicative functions for producing rAAV virions (see, e.g., U.S. Pat. No. 5,139,941, incorporated herein by reference in its entirety), Alternatively, a plasmid, containing helper function genes, in combination with infection by one of the well-known helper viruses can be used as the source of replicative functions (see e.g., U.S. Pat. Nos. 5,622,856 and 5,139,941, both incorporated herein by reference in their entireties). Similarly, a plasmid, containing accessory function genes can be used in combination with infection by wild-type AAV, to provide the necessary replicative functions. These three approaches, when used in combination with a rAAV vector, are each sufficient to produce rAAV virions. Other approaches, well known in the art, can also be employed by the skilled artisan to produce rAAV virions.

In one embodiment of the present invention, a triple transfection method (described in detail in U.S. Pat. No. 6,001,650, incorporated by reference herein in its entirety) is used to produce rAAV virions because this method does not require the use of an infectious helper virus, enabling rAAV virions to be produced without any detectable helper virus present. This is accomplished by use of three vectors for rAAV virion production: an AAV helper function vector, an accessory function vector, and a rAAV expression vector. One of skill in the art will appreciate, however, that the nucleic acid sequences encoded by these vectors can be provided on two or more vectors in various combinations.

As explained herein, the AAV helper function vector encodes the "AAV helper function" sequences (i.e., rep and cap), which function in trans for productive AAV replication and encapsidation. Preferably, the AAV helper function vector supports efficient AAV vector production without generating any detectable wt AAV virions AAV virions containing functional rep and cap genes), An example of such a vector, pHLP19, is described in U.S. Pat. No. 6,001,650, incorporated herein by reference in its entirety. The rep and cap genes of the AAV helper function vector can be derived from any of the known AAV serotypes, as explained above. For example, the AAV helper function vector may have a rep gene derived from AAV-2 and a cap gene derived from AAV-6; one of skill in the art will recognize that other rep and cap gene combinations are possible, the defining feature being the ability to support rAAV virion production.

The accessory function vector encodes nucleotide sequences for non-AAV-derived viral and/or cellular functions upon which AAV is dependent for replication (i.e., "accessory functions"). The accessory functions include those functions required for AAV replication, including, without limitation, those moieties involved in activation of AAV gene transcription, stage specific AAV mRNA splicing, AAV DNA replication, synthesis of cap expression products, and AAV capsid assembly. Viral-based accessory functions can be derived from any of the well-known helper viruses such as adenovirus, herpesvirus, and vaccinia virus. In one embodiment, the accessory function plasmid pLadeno5 is used (details regarding pLadeno5 are described in U.S. Pat. No. 6,004,797, incorporated herein by reference in its entirety). This plasmid provides a complete set of adenovirus accessory functions for AAV vector production, but lacks the components necessary to form replication-competent adenovirus.

In order to further an understanding of AAV, a more detailed discussion is provided below regarding recombinant AAV expression vectors and AAV helper and accessory functions Recombinant AAV Expression Vectors Recombinant AAV (rAAV) expression vectors are constructed using known techniques to at least provide as operatively linked components in the direction of transcription, control elements including a transcriptional initiation region, the polynucleotide of interest and a transcriptional termination region. The control elements are selected to be functional in the cell of interest, such as in a mammalian cell. The resulting construct which contains the operatively linked components is bounded (5' and 3') with functional AAV ITR sequences.

The nucleotide sequences of AAV ITR regions are known. See, e.g., Kotin, R. M. (1994) *Human Gene Therapy* 5:793-801; Berns, K. I. "Parvoviridae and their Replication" in *Fundamental Virology*, 2nd Edition, (B. N. Fields and D. M. Knipe, eds.) for the AAV-2 sequence. AAV ITRs used in the vectors of the invention need not have a wild-type nucleotide sequence, and may be altered, e.g., by the insertion, deletion or substitution of nucleotides. Additionally, AAV ITRs may be derived from any of several AAV serotypes, including without limitation, AAV-1, AAV-2, AAV-3, AAV- 4, AAV-5, AAV-6, AAV-7, AAV-8, AAV-9, etc. Furthermore, 5' and 3' ITRs which flank a selected nucleotide sequence in an AAV expression vector need not necessarily be identical or derived from the same AAV serotype or isolate, so long as they function as intended, i.e., to allow for excision and rescue of the sequence of interest from a host cell genome or vector, and to allow integration of the DNA molecule into the recipient cell genome when AAV Rep gene products are present in the cell.

Suitable polynucleotide molecules for use in traditional AAV vectors will be less than or about 5 kilobases (kb) in size. The selected polynucleotide sequence is operably linked to control elements that direct the transcription or expression thereof in the subject in vivo. Such control elements can comprise control sequences normally associated with the selected gene. Alternatively, heterologous control sequences can be employed. Useful heterologous control sequences generally include those derived from sequences encoding mammalian or viral genes. Non limiting examples of promoters include, but are not limited to, the cytomegalovirus (CMV) promoter (Kaplitt et al., *Nat. Genet.* (1994) 8:148-154), CMV/human β3-globin promoter (Mandel et al., *J. Neurosci.* (1998) 18:4271-4284), GFAP promoter (Xu et al., *Gene Ther.* (2001) 8:1323-1332), the 1.8-kb neuron-specific enolase (NSF) promoter (Klein et al., *Exp. Neurol.* (1998) 150:183-194), chicken beta actin (CBA) promoter (Miyazaki, *Gene* (1989) 79:269-277), the β-glucuronidase (GUSB) promoter (Shipley et al., *Genetics* (1991) 10:1009-1018), and ubiquitin promoters such as those isolated from human ubiquitin A, human ubiquitin B, and human ubiquitin C, as described in U.S. Pat. No. 6,667,174, incorporated herein by reference in its entirety. To prolong expression, other regulatory elements may additionally be operably linked to the transgene, such as, e.g., the Woodchuck Hepatitis Virus Post-Regulatory Element (WPRE) (Donello et al., *J. Virol.* (1998) 72:5085-5092) or the bovine growth hormone (BGH) polyadenylation site. In addition, sequences derived from nonviral genes, such as the murine metallothionein gene, will also find use herein. Such promoter sequences are commercially available from, e.g., Stratagene (San Diego, CA).

For some CNS gene therapy applications, it may be necessary to control transcriptional activity. To this end, pharmacological regulation of gene expression with viral vectors can be obtained by including various regulatory elements and drug-responsive promoters as described, for example, in Habermaet al., *Gene Ther.* (1998) 5.1604-16011; and Ye et al., *Science* (1995) 283:88-91.

The AAV expression vector which harbors the polynucleotide molecule of interest bounded by AAV ITRs, can be constructed by directly inserting the selected sequence(s) into an AAV genome which has had the major AAV open reading frames ("ORFs") excised therefrom. Other portions of the AAV genome can also be deleted, so long as a sufficient portion of the ITRs remain to allow for replication and packaging functions. Such constructs can be designed using techniques well known in the art. See, e.g., U.S. Pat. Nos. 5,173,414 and 5,139,941; International Publication Nos. WO 92/01070 (published 23 Jan. 1992) and WO 93/03769 (published 4 Mar. 1993); Lebkowski et al. (1988) *Molec. Cell. Biol.* 8:3988-3996; Vincent et al. (1990) *Vaccines* 90 (Cold Spring Harbor Laboratory Press); Carter (1992) *Current Opinion in Biotechnology* 3:533-539; Muzyczka (1992) *Current Topics in Microbial. and Immunol.* 158:97-129; Kotin (1994) *Human Gene Therapy* 5:793-801; Shelling and Smith (1994) *Gene Therapy* 1:165-169; and Zhou et al. (1994) *J. Exp. Med.* 179:1867-1875.

Alternatively, AAV ITRs can be excised from the viral genome or from an AAV vector containing the same and fused 5' and 3' of a selected nucleic acid construct that is present in another vector using standard ligation techniques, such as those described in Sambrook et al., supra. For example, ligations can be accomplished in 20 mM Tris-Cl pH 7.5, 10 mM MgCl2, 10 mM DTT, 33 µg/ml BSA, 10 mM-50 mM NaCl, and either 40 µM ATP, 0.01-0.02 (Weiss) units T4 DNA ligase at 0° C. (for "sticky end" ligation) or 1 mM ATP, 0.3-0.6 (Weiss) units T4 DNA ligase at 14° C. (for "blunt end" ligation). Intermolecular "sticky end" ligations are usually performed at 30-100 µg/ml total DNA concentrations (5-100 nM total end concentration). AAV vectors which contain ITRs have been described in, e.g., U.S. Pat. No. 5,139,941. In particular, several AAV vectors are described therein which are available from the American Type Culture Collection ("ATCC") under Accession Numbers 53222, 53223, 53224, 53225 and 53226.

In certain embodiments, the rAAV expression vectors are provided as self-complementary rAAV constructs. Typically, rAAV DNA is packaged into the viral capsid as a single-stranded DNA (ssDNA) molecule about 4600 nucleotides in length. Following infection of the cell by the virus, the single DNA strand is converted into a double-stranded DNA (dsDNA) form. Only the dsDNA is useful to proteins of the cell that transcribe the contained gene or genes into RNA. Thus, the conventional replication scheme of AAV requires de nova synthesis of a complementary DNA strand. This step of converting the ssDNA AAV genome into dsDNA prior to expression can be circumvented by the use of self-complementary (sc) vectors.

Self-complementary vectors are produced by base pairing complementary strands from two infecting viruses, which does not require DNA synthesis (see, e.g., Nakai et al., *J. Viral.* (2000) 74:9451-9463). This interstrand base pairing, or strand annealing (SA), is possible because AAV packages either the plus or minus DNA strand with equal efficiency (Berns, K. I., *Microbial. Rev.* (1990) 54:316-329).

Thus and without being limited as to theory, the need for dsDNA conversion, either by SA or DNA synthesis, can be entirely circumvented by packaging both strands as a single molecule. This can be achieved by taking advantage of the tendency of AAV to produce dimeric inverted repeat genomes during the AAV replication cycle. If these dimers are small enough, they can be packaged in the same manner as conventional AAV genomes, and the two halves of the ssDNA molecule can fold and base pair to form a dsDNA molecule of half the length. dsDNA conversion is independent of host-cell DNA synthesis and vector concentration (McCarty et al., *Gene Ther.* (2001) 8:1248-1254).

scAAV viral constructs include approximately 4.6 kb and are able to be packaged into the normal AAV capsid. Each of the known AAV serotypes is capable of packaging scAAV genomes with similar efficiency (see, e.g., Sipo et al., *Gene Ther* (2007) 14:1319-1329). Thus, in certain embodiments of the instant invention, the scAAV vector comprises capsid proteins from serotypes selected from AAV1, AAV2, AAV3, AAV4, AAV5, AAV6, AAV7, AAV8, or AAV9 serotypes. However, an scAAV vector may comprise capsid proteins from any of the known serotypes or modified capsid proteins known in the art. These scAAV vectors may also be pseudo-typed vectors comprising which contain the genome of one AAV serotype in the capsid of a second AAV serotype. Such vectors may comprise, for example, an AAV vector that contains the AAV2 capsid and the AAV1 genome or an AAV vector that contains the AAV5 capsid and the AAV 2 genome (Auricchio et al., (2001) Hum. Mol. Genet., 10 (26):3075-81).

Initially, it was believed that the transgene sequence in an scAAV vector could only comprise approximately 2.2 kb. However, it appears there is greater latitude in packaging capacity than previously believed. For example, Wu et al., *Human Gene Ther.* (2007) 18:171-182 successfully packaged scAAV-2 constructs exceeding 3,300 bp and demonstrated dimeric inverted repeat genomes that were fully DNase resistant. These vectors yielded the expected increases in transduction efficiency over ssAAV when tested on cultured cells.

scAAV vectors can be produced either by generating vector plasmids that are approximately half of the conventional genome size combined with selective purification of the infectious double stranded form, or through the use of approximately half-genome sized vector plasmids with a mutation in one of the terminal resolution sequences of the AAV virus that provides for synthesis of double-stranded virus. Both strategies generate + and − strand viral genomes that are covalently linked at one terminal repeat.

In particular, the generation of normal monomeric AAV genomes relies on the efficient resolution of the two ITRs in turn, with each round of DNA synthesis. This reaction is mediated by the ssDNA endonuclease activity of the two larger isoforms of AAV Rep. Nicking the ITR at the terminal resolution site is followed by DNA elongation from the nick by host DNA polymerase. Dimeric genomes are formed when Rep fails to nick the terminal resolution site before it is reached by the replication complex initiated at the other end.

The yield of dimeric genomes in a scAAV prep can be increased dramatically by inhibiting resolution at one terminal repeat. This is readily accomplished by deleting the terminal resolution site sequence from one ITR, such that the Rep protein cannot generate the essential ssDNA nick (see, e.g., McCarty et al., *Gene Ther.* (2003) 10:2112-2118 and Wang et al., *Gene Ther.* (2003) 10:2105-2111). The replication complex initiated at the other ITR then copies through the hairpin and back toward the initiating end. Replication proceeds to the end of the template molecule, leaving a dsDNA inverted repeat with a wild-type ITR at each end and the mutated ITR in the middle. This dimeric inverted repeat can then undergo normal rounds of replication from the two wild-type ITR ends. Each displaced daughter strand comprises a ssDNA inverted repeat with a complete ITR at each end and a mutated ITR in the middle. Packaging into the AAV capsid starts at the 3' end of the displaced strand. Production of scAAV from constructs with one mutated ITR typically yields more than 90% dimeric genomes.

Production and purification of scAAV vector from mutated ITR constructs is the same as conventional ssAAV, as described further below. However, if dot blot or Southern blot is used, the vector DNA is preferably applied to hybridization membranes under alkaline conditions to prevent reannealing of the complementary strands. Additionally, it is possible for a spurious Rep-nicking site to be produced close enough to the mutated ITR to allow terminal resolution and generation of monomer genomes. This can typically be avoided by turning the transgene cassette around with respect to the mutant and wild-type terminal repeats.

See, e.g., McCarty, D. M., Molec. Ther. (2008) 16:1648-1656; McCarty et al., *Gene Ther.* (2001) 8:1248-1254; McCarty et al., *Gene Ther.* (2003) 10:2112-2118; Wang et. al., *Gene Ther.* (2003) 10:2105-2111); Wu et al., *Human Gene Ther.* (2007) 18:171-182; U.S. Patent Publication Nos. 2007/0243168 and 2007/0253936, incorporated herein by reference in their entireties; as well as the examples herein, for methods of producing scAAV constructs.

For the purposes of the invention, suitable host cells for producing rAAV virions from the AAV expression vectors (either conventional or sc vectors) include microorganisms, yeast cells, insect cells, and mammalian cells, that can be, or have been, used as recipients of a heterologous DNA molecule and that are capable of growth in, for example, suspension culture, a bioreactor, or the like. The term includes the progeny of the original cell which has been transfected. Thus, a "host cell" as used herein generally refers to a cell which has been transfected with an exogenous DNA sequence. Cells from the stable human cell line, 293 (readily available through, e.g., the American Type Culture Collection under Accession Number ATCC CRL1573) are preferred in the practice of the present invention. Particularly, the human cell line 293 is a human embryonic kidney cell line that has been transformed with adenovirus type-5 DNA fragments (Graham et al. (1977) *J. Gen. Virol.* 36:59), and expresses the adenoviral E1a and E1b genes (Aiello et al. (1979) *Virology* 94:460). The 293 cell line is readily transfected, and provides a particularly convenient platform in which to produce rAAV virions.

AAV Helper Functions

Host cells containing the above-described AAV expression vectors must be rendered capable of providing AAV helper functions in order to replicate and encapsidate the nucleotide sequences flanked by the AAV ITRs to produce rAAV virions. AAV helper functions are generally AAV-derived coding sequences which can be expressed to provide AAV gene products that, in turn, function in trans for productive AAV replication. AAV helper functions are used herein to complement necessary AAV functions that are missing from the AAV expression vectors. Thus, AAV helper functions include one, or both of the major AAV ORFs, namely the rep and cap coding regions, or functional homologues thereof.

By "AAV rep coding region" is meant the art-recognized region of the AAV genome which encodes the replication proteins Rep 78, Rep 68, Rep 52 and Rep 40. These Rep expression products have been shown to possess many functions, including recognition, binding and nicking of the AAV origin of DNA replication, DNA helicase activity and modulation of transcription from AAV (or other heterologous) promoters. The Rep expression products are collectively required for replicating the AAV genome. For a description of the AAV rep coding region, see, e.g., Muzyczka, N. (1992) *Current Topics in Microbial. and Immunol.* 158:97-129; and Kotin, R. M. (1994) *Human Gene Therapy* 5:793-801. Suitable homologues of the AAV rep coding region include the human herpesvirus 6 (HHV-6) rep gene which is also known to mediate AAV-2 DNA replication (Thomson et al. (1994) *Virology* 204:304-311).

By "AAV cap coding region" is meant the art-recognized region of the AAV genome which encodes the capsid proteins VP1, VP2, and VP3, or functional homologues thereof. These Cap expression products supply the packaging functions which are collectively required for packaging the viral genome. For a description of the AAV cap coding region, see, e.g., Muzyczka, N. and Kotin, R. M. (supra).

AAV helper functions are introduced into the host cell by transfecting the host cell with an AAV helper construct either prior to, or concurrently with, the transfection of the AAV expression vector. AAV helper constructs are thus used to provide at least transient expression of AAV rep and/or cap genes to complement missing AAV functions that are necessary for productive AAV infection. AAV helper constructs lack AAV ITRs and can neither replicate nor package themselves.

These constructs can be in the form of a plasmid, phage, transposon, cosmid, virus, or virion. A number of AAV helper constructs have been described, such as the commonly used plasmids pAAV/Ad and pIM29+45 which encode both Rep and Cap expression products. See, e.g., Samulski et al. (1989) *J. Virol.* 63:3822-3828; and McCarty et al. (1991) *J. Virol.* 65:2936-2945. A number of other vectors have been described which encode Rep and/or Cap expression products. See, e.g., U.S. Pat. No. 5,139,941.

AAV Accessory Functions

The host cell (or packaging cell) must also be rendered capable of providing nonAAV-derived functions, or "accessory functions," in order to produce rAAV virions. Accessory functions are nonAAV-derived viral and/or cellular functions upon which AAV is dependent for its replication. Thus, accessory functions include at least those nonAAV proteins and RNAs that are required in AAV replication, including those involved in activation of AAV gene transcription, stage specific AAV mRNA splicing, AAV DNA replication, synthesis of Cap expression products and AAV capsid assembly. Viral-based accessory functions can be derived from any of the known helper viruses.

In particular, accessory functions can be introduced into and then expressed in host cells using methods known to those of skill in the art. Typically, accessory functions are provided by infection of the host cells with an unrelated helper virus. A number of suitable helper viruses are known, including adenoviruses; herpesviruses such as herpes simplex virus types 1 and 2; and vaccinia viruses. Nonviral accessory functions will also find use herein, such as those provided by cell synchronization using any of various known agents. See, e.g., Buller et al. (1981) *J. Viral.* 40:241-247; McPherson et al. (1985) *Virology* 147:217-222; Schlehofer et al. (1986) *Virology* 152:110-117.

Alternatively, accessory functions can be provided using an accessory function vector as defined above. See, e.g., U.S. Pat. No. 6,004,797 and international Publication No. WO 01/83797, incorporated herein by reference in their entireties. Nucleic acid sequences providing the accessory functions can be obtained from natural sources, such as from the genome of an adenovirus particle, or constructed using recombinant or synthetic methods known in the art. As explained above, it has been demonstrated that the full-complement of adenovirus genes are not required for accessory helper functions. In particular, adenovirus mutants incapable of DNA replication and late gene synthesis have been shown to be permissive for AAV replication. Ito et al., (1970) *J. Gen. Virol.* 9:243; Ishibashi et al, (1971) *Virology* 45:317. Similarly, mutants within the E2B and E3 regions have been shown to support AAV replication, indicating that the E2B and E3 regions are probably not involved in providing accessory functions. Carter et al., (1983) *Virology* 126:505. However, adenoviruses defective in the E1 region, or having a deleted E4 region, are unable to support AAV replication. Thus, E1A and E4 regions are likely required for AAV replication, either directly or indirectly. Laughlin et al., (1982) *J. Virol.* 41:868; Janik et al., (1981) *Proc. Natl. Acad. Sci. USA* 78:1925; Carter et al., (1983) *Virology* 126:505. Other characterized Ad mutants include: E1B (Laughlin et al. (1982), supra; Janik et al. (1981), supra; Ostrove et al., (1980) *Virology* 105:502); E2A (Handa et al., (1975) *J. Gen. Virol.* 29:239; Strauss et al., (1976) *J. Virol.* 17:140; Myers et al., (1980) *J. Virol.* 35:665; Jay et al., (1981) *Proc. Natl. Acad. Sci. USA* 78:2927; Myers et al., (1981) *J. Biol. Chem.* 256:567); E2B (Carter, *Adeno-Associated Virus Helper Functions*, in I *CRC Handbook of Parvoviruses* (P. Tijssen ed., 1990)); E3 (Carter et al. (1983), supra); and E4 (Carter et al. (1983), supra; Carter (1995)). Although studies of the accessory functions provided by adenoviruses having mutations in the E1B coding region have produced conflicting results, Samulski et al., (1988) *J. Virol.* 62:206-210, has reported that E1B55k is required for AAV virion production, while E1B19k is not. In addition, International Publication WO 97/17458 and Matshushita et al., (1998) *Gene Therapy* 5:938-945, describe accessory function vectors encoding various Ad genes. Particularly preferred accessory function vectors comprise an adenovirus VA RNA coding region, an adenovirus E4 ORF6 coding region, an adenovirus E2A 72 kD coding region, an adenovirus E1A coding region, and an adenovirus E1B region lacking an intact E1B55k coding region. Such vectors are described in International Publication No. WO 01/83797.

As a consequence of the infection of the host cell with a helper virus, or transfection of the host cell with an accessory function vector, accessory functions are expressed which transactivate the AAV helper construct to produce AAV Rep and/or Cap proteins. The Rep expression products excise the recombinant DNA (including the DNA of interest) from the AAV expression vector. The Rep proteins also serve to duplicate the AAV genome. The expressed Cap proteins assemble into capsids, and the recombinant AAV genome is packaged into the capsids. Thus, productive AAV replication ensues, and the DNA is packaged into rAAV virions. A "recombinant AAV virion," or "rAAV virion" is defined herein as an infectious, replication-defective virus including an AAV protein shell, encapsidating a heterologous nucleotide sequence of interest which is flanked on both sides by AAV ITRs.

Following recombinant AAV replication, rAAV virions can be purified from the host cell using a variety of conventional purification methods, such as column chromatography, CsCl gradients, and the like. For example, a plurality of column purification steps can be used, such as purification over an anion exchange column, an affinity column and/or a cation exchange column. See, for example, International Publication No. WO 02/12455. Further, if infection is employed to express the accessory functions, residual helper virus can be inactivated, using known methods. For example, adenovirus can be inactivated by heating to temperatures of approximately 60° C. for, e.g., 20 minutes or more. This treatment effectively inactivates only the helper virus since AAV is extremely heat stable while the helper adenovirus is heat labile.

The resulting rAAV virions containing the nucleotide sequence of interest can then be used for gene delivery using the techniques described below.

Compositions and Delivery

A. Compositions

Once produced, the rAAV virions encoding the gene of interest, will be formulated into compositions suitable for delivery. Compositions will comprise sufficient genetic material to produce a therapeutically effective amount of the gene of interest, i.e., an amount sufficient to (1) prevent the development of the disease or cause the disease to occur with less intensity in a subject that may be exposed to or predisposed to the disease but does not yet experience or display symptoms of the disease, (2) inhibit the disease, i.e., arrest the development or reverse the disease state, or (3) relieve symptoms of the disease i.e., decrease the number of symptoms experienced by the subject, as well as change the cellular pathology associated with the disease.

Appropriate doses will also depend on the mammal being treated (e.g., human or nonhuman primate or other mammal), age and general condition of the subject to be treated, the severity of the condition being treated, the mode of administration, among other factors. An appropriate effective amount can be readily determined by one of skill in the art and representative amounts are provided below.

The compositions will also contain a pharmaceutically acceptable excipient. Such excipients include any pharmaceutical agent that does not itself induce the production of antibodies harmful to the individual receiving the composition, and which may be administered without undue toxicity. Pharmaceutically acceptable excipients include, but are not limited to, sorbitol, any of the various TWEEN compounds, and liquids such as water, saline, glycerol and ethanol. Pharmaceutically acceptable salts can be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, may be present in such vehicles. A thorough discussion of pharmaceutically acceptable excipients is available in REMINGTON'S PHARMACEUTICAL SCIENCES (Mack Pub. Co., N.J. 1991).

Formulations can be liquid or solid, for example, lyophilized. Formulations can also be administered as aerosols.

One particularly useful formulation comprises the rAAV virion of interest in combination with one or more dihydric or polyhydric alcohols, and, optionally, a detergent, such as a sorbitan ester. See, for example, U.S. Pat. No. 6,764,845, incorporated herein by reference in its entirety.

B. Delivery

Generally, the recombinant virions are introduced into the subject using either in vivo or in vitro transduction techniques. If transduced in vitro, the desired recipient cell will be removed from the subject, transduced with the recombinant vector and reintroduced into the subject. Alternatively, syngeneic or xenogeneic cells can be used where those cells will not generate an inappropriate immune response in the subject. Suitable cells for delivery to mammalian host animals include mammalian cell types from organs, tumors, or cell lines. For example, human, murine, goat, ovine, bovine, dog, cat, and porcine cells can be used. Suitable cell types for use include without limitation, fibroblasts, hepatocytes, endothelial cells, keratinocytes, hematopoietic cells, epithelial cells, myocytes, neuronal cells, and stem cells. Additionally, neural progenitor cells can be transduced in vitro and then delivered to the CNS.

Cells can be transduced in vitro by combining recombinant virions with the desired cell in appropriate media, and the cells can be screened for those cells harboring the DNA of interest using conventional techniques such as Southern blots and/or PCR, or by using selectable markers. Transduced cells can then be formulated into pharmaceutical compositions, as described above, and the composition introduced into the subject by various techniques as described below, in one or more doses.

For in vivo delivery, the recombinant virions will be formulated into pharmaceutical compositions and one or more dosages may be administered directly in the indicated manner. For identification of structures in the human brain, see, e.g., The Human Brain: Surface, Three-Dimensional Sectional Anatomy With MRI, and Blood Supply, 2nd ed., eds. Deuteron et al., Springer Vela, 1999; Atlas of the Human Brain, eds. Mai et al., Academic Press; 1997; and Co-Planar Sterotaxic Atlas of the Human Brain: 3-Dimensional Proportional System: An Approach to Cerebral Imaging, eds. Tamarack et al., Thyme Medical Pub., 1988. For identification of structures in the mouse brain, see, e.g., The Mouse Brain in Sterotaxic Coordinates, 2nd ed., Academic Press, 2000. If desired, the human brain structure can be correlated to similar structures in the brain of another mammal. For example, most mammals, including humans and rodents, show a similar topographical organization of the entorhinal-hippocampus projections, with neurons in the lateral part of both the lateral and medial entorhinal cortex projecting to the dorsal part or septal pole of the hippocampus, whereas the projection to the ventral hippocampus originates primarily from neurons in medial parts of the entorhinal cortex (Principles of Neural Science, 4th ed., eds Kandel et al., McGraw-Hill, 1991; The Rat Nervous System, 2nd ed., ed. Paxinos, Academic Press, 1995). Furthermore, layer II cells of the entorhinal cortex project to the dentate gyrus, and they terminate in the outer two-thirds of the molecular layer of the dentate gyrus. The axons from layer III cells project bilaterally to the cornu ammonis areas CA1 and CA3 of the hippocampus, terminating in the stratum lacunose molecular layer.

To deliver the vector specifically to a particular region of the central nervous system, especially to a particular region of the brain, it may be administered by sterotaxic microinjection. For example, on the day of surgery, patients will have the sterotaxic frame base fixed in place (screwed into the skull). The brain with sterotaxic frame base (MRI-compatible with fiduciary markings) will be imaged using high resolution MRI. The MRI images will then be transferred to a computer that runs stereotaxic software. A series of coronal, sagittal and axial images will be used to determine the target site of vector injection, and trajectory. The software directly translates the trajectory into 3-dimensional coordinates appropriate for the stereotaxic frame. Burr holes are drilled above the entry site and the stereotaxic apparatus localized with the needle implanted at the given depth. The vector in a pharmaceutically acceptable carrier will then be injected. The vector is then administrated by direct injection to the primary target site and retrogradely transported to distal target sites via axons. Additional routes of administration may be used, e.g., superficial cortical application under direct visualization, or other non-stereotaxic application.

Recombinant AAV of any serotype can be used in the instant invention, wherein the recombinant AAV may be either a self-complementary AAV or a non-self complementary AAV. The serotype of the viral vector used in certain embodiments of the invention is selected from the group consisting from AAV1, AAV2, AAV3, AAV4, AAV5, AAV6, AAV7, AAV8, and AAV9 (see, e.g., Gao et al. (2002) PNAS, 99:11854 11859; and Viral Vectors for Gene Therapy: Methods and Protocols, ed. Machida, Humana Press, 2003). Other serotype besides those listed herein can be used. Furthermore, pseudotyped AAV vectors may also be utilized in the methods described herein. Pseudotyped AAV vectors are those which contain the genome of one AAV serotype in the capsid of a second AAV serotype; for example, an AAV vector that contains the AAV2 capsid and the AAV1 genome or an AAV vector that contains the AAV5 capsid and the AAV 2 genome (Auricchio et al., (2001) Hum. Mol. Genet., 10 (26):3075-81).

Recombinant virions or cells transduced in vitro may be delivered directly to neural tissue such as peripheral nerves, the retina, dorsal root ganglia, neuromuscular junction, as well as the CNS, by injection into, e.g., the ventricular region, such as one or both of the lateral ventricles, as well as to the striatum (e.g., the caudate nucleus or putamen of the striatum), the cerebellum, spinal cord, and neuromuscular junction, with a needle, catheter or related device, using neurosurgical techniques known in the art, such as by stereotactic injection (see, e.g., Stein et al., *J Virol* 73:3424-3429, 1999; Davidson et al., *PNAS* 97:3428-3432, 2000; Davidson et al., *Nat. Genet.* 3:219-223, 1993; and Alisky and Davidson, *Hum. Gene Ther.* 11:2315-2329, 2000). In an illustrative embodiment, the delivery is accomplished by direct injection of a high titer vector solution into the spinal cord of a subject or patient.

In another illustrative embodiment, a method to deliver a transgene to the spinal cord and/or the brainstem region of a subject by administering a recombinant AAV vector containing the transgene to at least one region of the deep cerebellar nuclei (DCN) region of the cerebellum of the subject's brain. Deep within the cerebellum is grey matter called the deep cerebellar nuclei termed the medial (fastigial) nucleus, the interposed (interpositus) nucleus and the lateral (dentate) nucleus. As used herein, the term "deep cerebellar nuclei" collectively refers to these three regions, wherein one or more of these three regions may be targeted. The viral delivery is under conditions that favor expression of the transgene in the spinal cord and/or the brainstem region. in at least one subdivision of the spinal cord of the subject. These subdivisions include one or more of cervical, thoracic, lumbar or sacral.

Without being limited as to theory, one embodiment of the invention lies in the ability to provide a therapeutic molecule (for example, a protein or peptide) to each division of the spinal cord. This may be accomplished by injecting an AAV vector, including a scAAV vector into the DCN. Furthermore, it may be important to target individual lamina within each spinal cord division. Lamina are specific sub-regions within regions of the brain and spinal cord. It may be desirable in certain embodiments to target specific lamina within a certain spinal cord division. Since motor neuron damage may occur within the upper motor neurons as well, it may also be desirable to provide a therapeutic molecule (for example, a protein or peptide) to the divisions of the brainstem. In one embodiment, it may be desirable to provide the therapeutic molecule to both the spinal cord, including some or all subdivisions as well as to the brainstem, including some or all subdivisions. The instant invention uses the introduction of an AAV vector into the DCN to accomplish the above described delivery of a therapeutic molecule to the spinal cord region(s) and/or brainstem.

Another method for targeting spinal cord (e.g., glia) is by intrathecal delivery, rather than into the spinal cord tissue itself. Such delivery presents many advantages. The targeted protein is released into the surrounding CSF and unlike viruses, released proteins can penetrate into the spinal cord parenchyma, just as they do after acute intrathecal injections. Indeed, intrathecal delivery of viral vectors can keep expression local. An additional advantage of intrathecal gene therapy is that the intrathecal route mimics lumbar puncture administration (i.e., spinal tap) already in routine use in humans.

Another method for administering the recombinant vectors or transduced cells is by delivery to dorsal root ganglia (DRG) neurons, e.g., by injection into the epidural space with subsequent diffusion to DRG. For example, the recombinant vectors or transduced cells can be delivered via intrathecal cannulation under conditions where the protein is diffused to DRG. See, e.g., Chiang et al., *Acta Anaesthesiol. Sin.* (2000) 38:31-36; Jain, K. K., *Expert Opin. Investig. Drugs* (2000) 9:2403-2410.

Yet another mode of administration to the CNS uses a convection-enhanced delivery (CED) system, which is any non-manual delivery of the vector. In one embodiment of CED, a pressure gradient is created via the use of a non-manual delivery system. By using CED, recombinant vectors can be delivered to many cells over large areas of the CNS. Moreover, the delivered vectors efficiently express transgenes in CNS cells (e.g., glial cells). Any convection-enhanced delivery device may be appropriate for delivery of recombinant vectors. In a preferred embodiment, the device is an osmotic pump or an infusion pump. Both osmotic and infusion pumps are commercially available from a variety of suppliers, for example Alzet Corporation, Hamilton Corporation, Alza, Inc., Palo Alto, California). Typically, a recombinant vector is delivered via CED devices as follows. A catheter, cannula or other injection device is inserted into CNS tissue in the chosen subject. Stereotactic maps and positioning devices are available, for example from ASI Instruments, Warren, MI Positioning may also be conducted by using anatomical maps obtained by CT and/or MRI imaging to help guide the injection device to the chosen target. Moreover, because the methods described herein can be practiced such that relatively large areas of the subject take up the recombinant vectors, fewer infusion cannula are needed. Since surgical complications are often related to the number of penetrations, this mode of delivery serves to reduce the side-effects seen with conventional delivery techniques. For a detailed description regarding CED delivery, see U.S. Pat. No. 6,309,634, incorporated herein by reference in its entirety.

Intracerebroventricular, or intraventricular, delivery of a recombinant AAV vector may be performed in any one or more of the brain's ventricles, which are filled with cerebrospinal fluid (CSF). CSF is a clear fluid that fills the ventricles, is present in the subarachnoid space, and surrounds the brain and spinal cord. CSF is produced by the choroid plexuses and via the weeping or transmission of tissue fluid by the brain into the ventricles. The choroid plexus is a structure lining the floor of the lateral ventricle and the roof of the third and fourth ventricles. Certain studies have indicated that these structures are capable of producing 400-600 ccs of fluid per day consistent with an amount to fill the central nervous system spaces four times in a day. In adult humans, the volume of this fluid has been calculated to be from 125 to 150 ml (4-5 oz). The CSF is in continuous formation, circulation and absorption. Certain studies have indicated that approximately 430 to 450 ml (nearly 2 cups) of CSF may be produced every day. Certain calculations estimate that production equals approximately 0.35 ml per minute in adults and 0.15 per minute in infant humans. The choroid plexuses of the lateral ventricles produce the majority of CSF. It flows through the foramina of Monro into the third ventricle where it is added to by production from the third ventricle and continues down through the aqueduct of Sylvius to the fourth ventricle. The fourth ventricle adds more CSF; the fluid then travels into the subarachnoid space through the foramina of Magendie and Luschka. It then circulates throughout the base of the brain, down around the spinal cord and upward over the cerebral hemispheres. The CSF empties into the blood via the arachnoid villi and intracranial vascular sinuses.

In one aspect, the disclosed methods include administering to the CNS of an afflicted subject a rAAV virion carrying a transgene encoding a therapeutic product and allowing the transgene to be expressed within the CNS near the administration site at a level sufficient to exert a therapeutic effect as the expressed protein is transported via the CSF throughout the CNS. In some embodiments, the methods comprise administration of a high titer virion composition carrying a therapeutic transgene so that the transgene product is expressed at a therapeutic level at a first site within the CNS distal to the ultimate site of action of the expressed product.

In experimental mice, the total volume of injected AAV solution is for example, between 1 to 20 µl. For other mammals, including the human, volumes and delivery rates are appropriately scaled. Treatment may consist of a single injection per target site, or may be repeated in one or more sites. Multiple injection sites can be used. For example, in some embodiments, in addition to the first administration site, a composition containing a viral vector carrying a transgene is administered to another site which can be contralateral or ipsilateral to the first administration site. Injections can be single or multiple, unilateral or bilateral.

Dosage treatment may be a single dose schedule, continuously or intermittently, or a multiple dose schedule. Moreover, the subject may be administered as many doses as appropriate. If multiple doses are administered, the first formulation administered can be the same or different than the subsequent formulations. Thus, for example, the first administration can be in the form of an AAV vector and the second administration in the form of an adenovirus vector, plasmid DNA, a protein composition, or the like. Moreover, subsequent delivery can also be the same or different than the second mode of delivery.

In addition, the subject may receive the rAAV vector of the instant invention by a combination of the delivery methods disclosed therein. Thus, a subject may receive injections of an AAV vector in at least two injection sites selected from the group consisting of intracerebroventricular injections, direct spinal cord injections, intrathecal injections, and intraparenchymal brain injections (e.g., the striatum, the cerebellum, including the deep cerebellar nuclei). In one embodiment, the subject may receive rAAV vector via 1) at least one intracerebroventricular injection, and at least one direct spinal cord injection or 2) at least one intracerebroventricular injection and at least one intrathecal injection or 3) at least one intracerebroventricular injection and at least one intraparenchymal brain injection or 4) at least one direct spinal cord injection and at least one intrathecal injection or 5) at least one direct spinal cord injection and at least one intraparenchymal brain injection or 6) at least one intrathecal injection and at least one intraparenchymal brain injection.

It should be understood that more than one transgene can be expressed by the delivered recombinant virion. Alternatively, separate vectors, each expressing one or more different transgenes, can also be delivered to the subject as described herein. Thus, multiple transgenes can be delivered concurrently or sequentially. Furthermore, it is also intended that the vectors delivered by the methods of the present invention be combined with other suitable compositions and therapies. Additionally, combinations of protein and nucleic acid treatments can be used.

Methods of determining the most effective means of administration and therapeutically effective dosages are well known to those of skill in the art and will vary with the vector, the composition of the therapy, the target cells, and the subject being treated. Therapeutically effective doses can be readily determined using, for example, one or more animal models of the particular disease in question. A "therapeutically effective amount" will fall in a relatively broad range that can be determined through clinical trials. For example, for in vivo injection of rAAV virions, a dose will be on the order of from about $10^6$ to $10^{15}$ genome particles of the recombinant virus, more preferably $10^8$ to $10^{14}$ genome particles recombinant virus, or any dose within these ranges which is sufficient to provide the desired affect. In certain embodiments, the concentration or titer of the vector in the composition is at least: (a) 5 6, 7, 8, 9, 10, 15, 20, 25, or 50 ($\times 10^{12}$ gp/ml); (b) 5 6, 7, 8, 9, 10, 15, 20, 25, or 50 ($\times 10^9$ tu/ml); or (c) 5, 6, 7, 8, 9, 10, 15, 20, 25, or 50 ($\times 10^{10}$ iu/ml).

For in vitro transduction, an effective amount of rAAV virions to be delivered to cells will be on the order of $10^8$ to $10^{13}$ of the recombinant virus. The amount of transduced cells in the pharmaceutical compositions, in turn will be from about $10^4$ to $10^{10}$ cells, more preferably $10^5$ to $10^8$ cells. Other effective dosages can be readily established by one of ordinary skill in the art through routine trials establishing dose response curves.

Generally, from 1 µl to 1 ml of composition will be delivered, such as from 0.01 to about 0.5 ml, for example about 0.05 to about 0.3 ml, such as 0.08, 0.09, 0.1, 0.2, etc. and any number within these ranges, of composition will be delivered.

Animal Models

Therapeutic effectiveness and safety using the AAV virions including transgenes as described above can be tested in an appropriate animal model. For example, animal models which appear most similar to human disease include animal species which either spontaneously develop a high incidence of the particular disease or those that have been induced to do so.

In particular, several animal models for SMA are known and have been generated. See, e.g., Sumner C. J., *NeuroRx* (2006) 3:235-245; Schmid et al., *J. Child Neurol.* (2007) 22:1004-1012. As explained above, the molecular basis of SMA, an autosomal recessive neuromuscular disorder, is the homozygous loss of the survival motor neuron gene 1 (SMN1). A nearly identical copy of the SMN1 gene, called SMN2 is found in humans and modulates the disease severity. In contrast to humans, mice have a single gene (SMN) that is equivalent to SMN1. Homozygous loss of this gene is lethal to embryos and results in massive cell death, which indicates that the SMN gene product is necessary for cellular survival and function. The introduction of 2 copies of SMN2 into mice lacking SMN rescues the embryonic lethality, resulting in mice with the SMA phenotype (Monani et al., *Hum. Mol. Genet.* (2000) 9:333-339. A high copy number of SMN2 rescues the mice because sufficient SMN protein is produced in motor neurons. See, also, Hsieh-Li, et al., *Nat. Genet.* (2000) 24:66-70, reporting the production of transgenic mouse lines that expressed human SMN2. In particular, transgenic mice harboring SMN2 in the SMN−/− background show pathological changes in the spinal cord and skeletal muscles similar to those of SMA patients. The severity of the pathological changes in these mice correlates with the amount of SMN protein that contained the region encoded by exon 7. Phenotypes in this mouse model include motor neuron cell loss, skeletal muscle atrophy, aberrant neuromuscular junctions (NMJ), behavioral deficits, paralysis, and a shortened life span of about two weeks. Le et al., *Hum Mol. Genet*. (2005) 14:845-857.

Similarly, animal models for ALS are known. ALS is a fatal neurodegenerative disease that is characterized by a selective loss of motor neurons in the cortex, brain stem and spinal cord. Progression of the disease can lead to atrophy of limb, axial and respiratory muscles. Motor neuron cell death is accompanied by reactive gliosis, neurofilament abnormalities, and a significant loss of large myelinated fibers in the corticospinal tracts and ventral roots. Although the etiology of ALS is poorly understood, accumulating evidence indicates that sporadic (SALS) and familial (FALS) ALS share many similar pathological features; thus, providing a hope that the study of either form will lead to a common treatment. FALS accounts for approximately 10% of diagnosed cases, of which 20% are associated with dominantly inherited mutations in Cu/Zn superoxide dismutase (SODI). Transgenic mice that express the mutant human SODI protein (e.g., SODIG93A mice) recapitulate many pathological features of ALS and are an available anima model to study ALS. For SALS, a myriad of pathological mechanisms have been implicated as the underlying cause, including glutamate induced excitotoxicity, toxin exposure, proteasome dysfunction, mitochondrial damage, neurofilament disorganization and loss of neurotrophic support.

Experimental Autoimmune Encephalomyelitis (EAE), also called Experimental Allergic Encephalomyelitis, provides an animal model for MS. EAE resembles the various forms and stages of MS very closely. EAE is an acute or chronic-relapsing, acquired, inflammatory and demyelinating autoimmune disease. In order to create the disease, animals are injected with proteins that make up myelin, the insulating sheath that surrounds neurons. These proteins induce an autoimmune response in the injected animals which develop a disease process that closely resembles MS in humans. EAE has been induced in a number of different animal species including mice, rats, guinea pigs, rabbits, macaques, rhesus monkeys and marmosets.

Spinal and bulbar muscular atrophy (SBMA) is an adult-onset motor neuron disease, caused by the expansion of a trinucleotide repeat (TNR) in exon 1 of the androgen receptor (AR) gene. This disorder is characterized by degeneration of motor and sensory neurons, proximal muscular atrophy, and endocrine abnormalities, such as gynecomastia and reduced fertility. Only males develop symptoms, while female carriers usually are asymptomatic. The molecular basis of SBMA is the expansion of a trinucleotide CAG repeat, which encodes the polyglutamine (polyQ) tract, in the first exon of the androgen receptor (AR) gene. The pathologic hallmark is nuclear inclusions (NIs) containing the mutant and truncated AR with expanded polyQ in the residual motor neurons in the brainstem and spinal cord as well as in some other visceral organs. Several transgenic mouse models have been created for studying the pathogenesis of SBMA. See, e.g., Katsuno et al., *Cytogen. and Genome Res*. (2003) 100:243-251. For example, a transgenic mouse model carrying pure 239 CAGs under human AR promoter and another model carrying truncated AR with expanded CAGs show motor impairment and nuclear NIs in spinal motor neurons. Transgenic mice carrying full-length human AR with expanded polyQ demonstrate progressive motor impairment and neurogenic pathology as well as sexual difference of phenotypes. These models recapitulate the phenotypic expression observed in SBMA.

Machado-Joseph disease (MJD), also called spinocerebellar ataxia type 3, is caused by mutant ataxin-3 with a polyglutamine expansion. Mouse models of MJD, as well as other polyglutamine spinocerebellar ataxias have been generated. For a review of these models, see e.g., Gould, V. F. C. *NeuroRX* (2005) 2:480-483.

Accordingly, animal models standard in the art are available for the screening and/or assessment for activity and/or effectiveness of the methods and compositions of the invention for the treatment of motor neuron disorders.

Kits of the Invention

The invention also provides kits. In certain embodiments, the kits of the invention comprise one or more containers comprising recombinant vectors encoding the protein of interest. The kits may further comprise a suitable set of instructions, generally written instructions, relating to the use of the vectors for any of the methods described herein.

The kits may comprise the components in any convenient, appropriate packaging. For example, if the recombinant vectors are provided as a dry formulation (e.g., freeze dried or a dry powder), a vial with a resilient stopper is normally used, so that the vectors may be easily resuspended by injecting fluid through the resilient stopper. Ampules with non-resilient, removable closures (e.g., sealed glass) or resilient stoppers are most conveniently used for liquid formulations. Also contemplated are packages for use in combination with a specific device, such as a syringe or an infusion device such as a minipump.

The instructions relating to the use or the recombinant vectors generally include information as to dosage, dosing schedule, and route of administration for the intended method of use. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

2. Experimental

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Materials and Methods

AAV vectors. The open reading frame of a exemplary human SMN1 gene (the open reading frame sequence is shown in FIG. 9A; the corresponding amino acid sequence is shown in FIG. 9B; the complete nucleotide sequence is found at GenBank accession number NM_000344)) was cloned into a shuttle plasmid containing either the AAV2 inverted terminal repeats (ITR) and the 1.6 kb cytomegalovirus enhancer/chicken β-actin (CBA) promoter or the scAAV2 ITR and the 0.4 kb human β-glucuronidase (GUSB) promoter. The size constraint of the recombinant genome in the scAAV packaging reaction required the use of a small promoter (McCarty, D. M. *Molec. Ther*. (2008) 16:1648-1656). Thus, the 0.4 kb GUSB promoter was chosen because it is ubiquitously expressed throughout the CNS including motor neurons of the spinal cord (Passini et al., *J. Virol.* (2001) 75:12382-12392). The recombinant plasmids were each packaged into AAV serotype-8 capsid by triple-plasmid cotransfection of human 293 cells (see, e.g., U.S. Pat. No. 6,001,650, incorporated by reference herein in its entirety) and virions were column-purified as reported previously (O'Riordan et al., *J. Gene Med.* (2000) 2:444-454.). The resulting vectors AAV2/8-CBA-hSMN1 (AAV-hSMN1) and scAAV2/8-GUSB-hSMN1 (scAAV-hSMN1) possessed titers of 8.3 e12 and 2.8 e12 genome copies per ml, respectively.

Animals and procedures. Heterozygote ($SMN^{+/-}$, $hSMN2^{+/+}$, $SMN\Delta7^{+/+}$) breeding pairs were mated and, on the day of birth (P0), newborn pups received 3 total injections of 2 µl each into the cerebral lateral ventricles of both hemispheres and the upper lumbar spinal cord. The total doses of viral vectors were 5.0 e10 and 1.7 e10 genome copies for AAV-hSMN1 and scAAV-hSMN1, respectively. All the injections were performed with a finely drawn glass micropipette needle as described (Passini et al, *J. Virol.* (2001) 75:12382-12392). Following the injections, the pups were toe-clipped and genotyped (Le et al., *Hum. Mol. Genet.* (2005) 14:845-857) to identify SMA ($SMN^{-/-}$, $hSMN2^{+/+}$, $SMN\Delta7^{+/+}$), heterozygote, and wild type ($SMN^{+/+}$, $hSMN2^{+/+}$, $SMN\Delta7^{+/+}$) mice. All the litters were culled to 7 pups to control for litter size on survival. Some of the litters were not injected in order to generate untreated control groups.

Western blots. For biochemical analysis, treated and untreated mice were killed at 16 and 58-66 days were perfused with phosphate-buffered saline (PBS), the spinal cords were dissected and separated into the lumbar, thoracic and cervical segments, and snap-frozen in liquid nitrogen. Tissues were homogenized at a concentration of 50 mg/mL using T-Per lysis buffer and protease inhibitor cocktail (Pierce, Rockford, IL), The homogenates were cleared by centrifugation at 10,000 RCF for 6 minutes and the protein concentration was measured by BCA assay (Pierce, Rockford, IL). 10-20 µg of homogenate protein were resolved on a 4-12% SDS-PAGE, transferred to nitrocellulose membrane, and probed with a mouse monoclonal anti-SMN (1:5,000 BD Biosciences, San Jose, CA) and a rabbit polyclonal anti-β-tubulin (1:750, Santa Cruz Biotechnology, Santa Cruz, CA) antibodies. The membranes were incubated with infrared secondary antibodies (1:20,000, LI-COR Biosciences, Lincoln NE), and protein bands were visualized by quantitative fluorescence using Odyssey (LI-COR Biosciences). Molecular weight markers confirmed the sizes of the bands.

Immunohistochemistry. For histological analysis, treated and untreated mice were killed at 16 and 58-66 days were perfused with 4% paraformaldehyde (pH 7.4), the spinal cords were removed and placed in 30% sucrose for 48-72 hours, embedded in OCT and cut into 10 µm frozen sections by a cryostat. Spinal cord sections were blocked for 1 h at room temperature (RT) and then incubated with either a mouse monoclonal anti-SMN antibody (1:200 dilution) to identify AAV-derived hSMN expression, or a goat polyclonal anti-choline acetyl transferase (ChAT) antibody (Millipore; Burlington, MA; 1:100 dilution) to identify motor neurons of laminae 8 and 9 (ventral horn) of the spinal cord or a rabbit polyclonal anti-glial fibrillary acidic protein (GFAP) antibody (Sigma-Aldrich, 1:2,500 dilution) to detect astrocytes. Primary antibodies were incubated for 1 h at RT followed by an overnight incubation at 4° C. in a humidified chamber. Spinal cord sections were then incubated for 1 h at RT with either a FITC-conjugated anti-rabbit secondary antibody or a Cy3-conjugated anti-goat secondary antibody (Jackson ImmunoResearch; West Grove, PA; 1:250 dilution). To increase the SMN and ChAT immuno-positive signal, a TSA signal amplification kit (Perkin Elmer; Waltham, MA) or a citric acid antigen retrieval protocol (Vector Labs; Burlingame, CA) were performed according to the manufacturer's instruction, respectively. Sections were cover-slipped with Vectashield mounting media (Vector Labs; Burlingame, CA).

Motor neuron counting. The number of ChAT immuno-positive cells was counted in the cervical, thoracic, and lumbar segments. Bilateral counts were performed at 100× magnification in the ventral horns along the rostrocaudal axis of the three spinal cord segments. Adjacent sections were at least 100 microns apart to prevent double counting of the same cell. Special care was taken to compare anatomically matched sections between different animals, and all cell counts were assessed blind by a single observer. Cells located in laminae 8 and 9 of the spinal cord exhibiting a fluorescent ChAT signal markedly above background were considered motor neurons.

Myofiber size. For histological analysis of the periphery, the fixed quadriceps, gastrocnemius and intercostal muscles from the right side of each mouse were processed by paraffin and stained for hematoxylin-eosin to determine myofiber size as reported (Avila et al., *J. Clin. Invest.* (2007) 117: 659-671). Approximately 500 non-overlapping myofibers from each muscle per animal were randomly selected and photographed at 60× magnification. The cross-section areas of each myofiber were measured using a Metamorph software (Molecular Devices, Sunnyvale, CA).

Neuromuscular Junction Staining (NMJ). The fixed muscle groups from the left side of each mouse were stored in PBS for NMJ analysis. In toto staining on teased muscle fibers from the quadriceps, gastrocnemius and intercostals muscles was performed as reported (Lesbordes et al., *Hum. Mol. Genet.* (2003) 12:1233-1239). Pre-synaptic nerve terminals were labeled by overnight incubation at 4° C. with a rabbit polyclonal antibody against the 150 kD neurofilament isoform (NF-M, Millipore, Billerica, MA, 1:200 dilution), followed by a biotinylated anti-rabbit secondary antibody (Jackson ImmunoResearch, 1:200 dilution). Acetylcholine receptors on the muscle endplates were labeled with Alexa 555-conjugated α-bungarotoxin (Molecular Probes, Eugene, OR) at 1:5000 for 3 h at RT. Stained muscle fibers were mounted onto slides, cover-slipped with Vectashield, and viewed under epifluorescence. For NMJ quantification, a minimum of 100 NMJs from each muscle per animal were randomly selected and assessed under the microscope. Confocal images were captured using a Zeiss LSM 510-META microscope.

Behavior tests. In the righting reflex, each mouse was placed on a supine position and the time taken for the mouse to reposition itself onto all four paws was measured. The procedure was repeated three times for each animal, and the average of the three scores was designated the righting score. If the mouse did not respond within 60 seconds, the test was terminated. In the negative geotaxis, each mouse was placed on a 45°-platform facing downward. The test was deemed a success if the mouse turned 180° to the "head up" position. Each mouse was given three attempts to complete the task in 180 seconds or less. In the grip strength, the forelimbs and hindlimbs were placed together on a wire grid and gently dragging horizontally along the mesh. Resistance was recorded in grams by a force transducer. In the hindlimb splay test, each mouse was suspended by its tail for 5 seconds and the resulting splay was scored based on an arbitrary system. A healthy splay of both hindlimbs similar to that observed in wild-type mice was given a score of 4. An acute splay angle or "weak splay" of both hindlimbs was a score of 3. A single leg splay was assigned a score of 2. A mouse that exhibited no splay was given a score of 1. Finally, a score of 0 occurred when the pup pulled both hindlimbs together, effectively crossing them over the other.

Statistics. The behavioral tests, the number of motor neurons, the cross-section myofiber areas, and the NMJ were analyzed with one-way ANOVA and Bonferroni multiple post hoc comparisons and with unpaired two-tailed student t-tests. The Kaplan-Meier survival curve was analyzed with the log-rank test equivalent to the Mantel-Haenszel test. All statistical analyses were performed with GraphPad Prism v4.0 (GraphPad Software, San Diego, CA). Values with $p<0.05$ were considered significant.

Example 1

Significant Increase in Survival with Treatment Using AAV-Mediated SMN1 Delivery SMA mice on postnatal day 0 (P0) were injected intracerebroventricularly with AAV-hSMN1 into both cerebral lateral ventricles and by direct spinal cord injection into the upper lumbar spinal cord for a total dose of 5.0 e10 genome copies per mouse. Treated and untreated SMA mice were randomly separated into either a survival cohort in which all the mice were left undisturbed and sacrificed at a humane end point, or into an age-matched cohort in which all the mice were sacrificed at 16 days for age-matched comparisons with end-stage untreated SMA mice.

In the survival cohort, SMA mice treated with AAV-hSMN1 showed a significant increase in median lifespan to 50 days ($p<0.0001$), compared to 15 days in untreated SMA controls (FIG. 1). All of the treated SMA mice were alive at 15 days, and 87.5% of the treated SMA mice were alive at 19 days compared to 0% in untreated SMA. The Kaplan-Meier curve showed a bimodal survival distribution with treatment, in which the first group died at 17-27 days and the second group at 58-66 days (FIG. 1). In the first group, the majority of the treated SMA mice showed ambulation, but the mice were stunted in growth and were ultimately found dead in the cage. The second group of treated SMA mice at 58-66 days showed ambulation and weight gain, but eventually developed severe hindlimb necrosis that resulted in euthanasia of the animal. As such, the 58-66 days mice were analyzed in parallel with the 16-days age-matched cohort.

Example 2

AAV-Mediated Expression of SMN in the Spinal Cord and Motor Neuron Counts

Figure 2A:
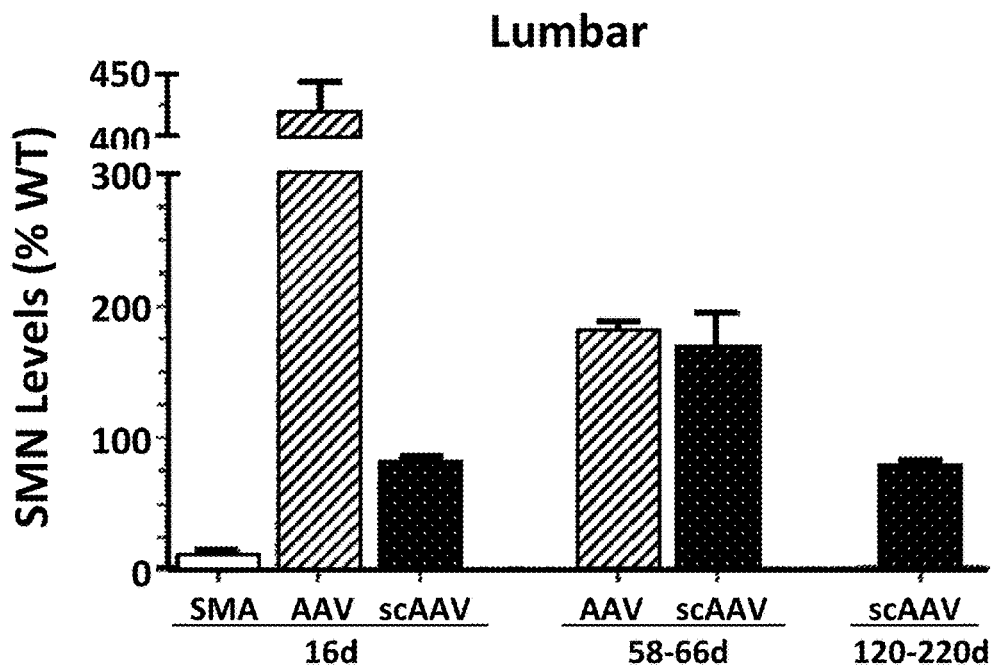
FIGS. 2A-2C show the effect of gene therapy treatment on SMN levels in the spinal cord. Shown are hSMN protein levels in injected lumbar (FIG. 2A), thoracic (FIG. 2B) and cervical (FIG. 2C) segments compared to untreated SMA and wild-type mice. Western blots were performed on the lumbar, thoracic and cervical segments of the spinal cord at 16, 58-66 and 120-220 days after injection. The western blots from the three segments were quantified and, to control for protein levels, SMN was normalized to β-tubulin and plotted as a percentage of age-matched wild type. Key (and n-values): SMA, untreated knockout (n=5 at 16 days); AAV, AAV8-hSMN-treated SMA mice (n=7 at 16 days, n=5 at 58-66 days); scAAV, scAAV8-hSMN-treated SMA mice (n=5 at each time point). Values represent the mean±SEM.
Figure 2B:
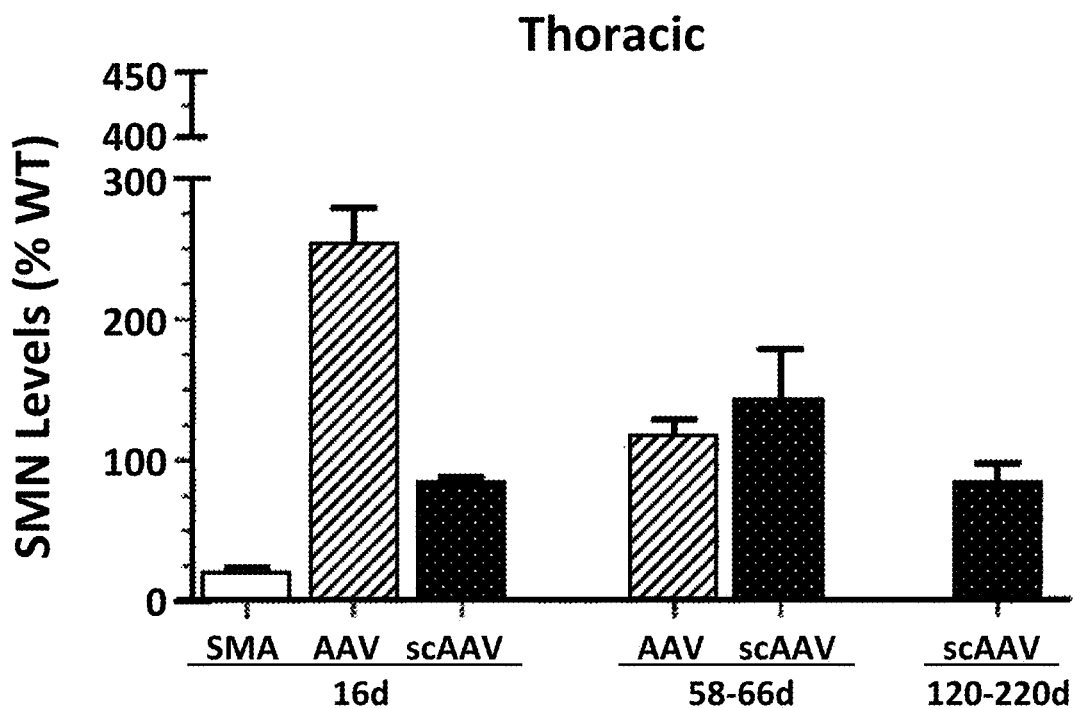
Figure 2C:
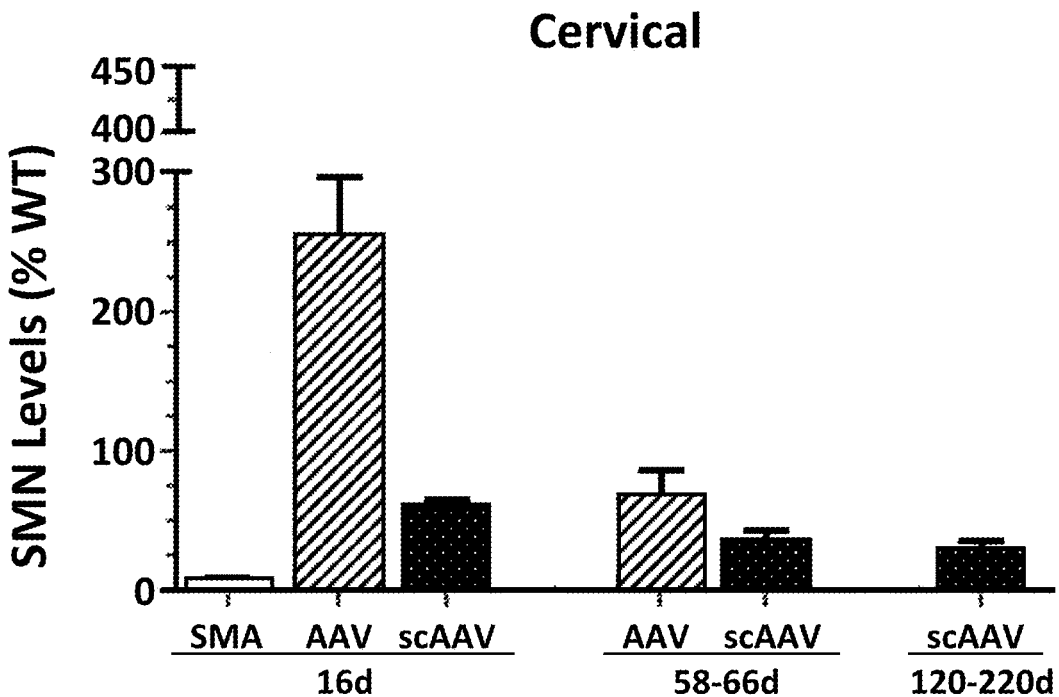

Levels of hSMN protein increased throughout the spinal cord following CNS administration of AAV-hSMN1. In AAV-treated SMA mice at 16 days, there was an approximate 34.0- and 3.6-fold increase in hSMN protein levels in the injected lumbar segment compared to untreated SMA and wild-type mice, respectively (FIG. 2A). The increase in hSMN protein expression extended into the other segments, which included a >2.0-fold increase above wild type levels in the thoracic and cervical spinal cord at 16 days (FIGS. 2B and 2C). In the second group, hSMN protein expression was sustained in AAV-treated SMA mice at 58-66 days. The injected lumbar and neighboring thoracic and cervical regions was approximately 2.5-, 2.2- and 1.2-fold higher than age-matched WT controls, respectively.

Figure 3D:

Immunostaining of tissue sections showed hSMN protein in the dorsal and ventral horns of the spinal cord in treated SMA mice at 16 and 58-66 days (FIG. 3). Upon closer examination of the transduced cells, vector-derived hSMN expression was detected in a punctate pattern throughout the cytosol, and in gem-like structures in the nucleus (FIG. 3A). Furthermore, hSMN protein was localized to neurites in distinct granule-like structures that could be seen spanning the length of dendrites and axons (FIGS. 3B-3D). The very low level of endogenous hSMN protein in SMA mice was below the threshold of immunodetection in cells (FIG. 3E).

Figure 3J:
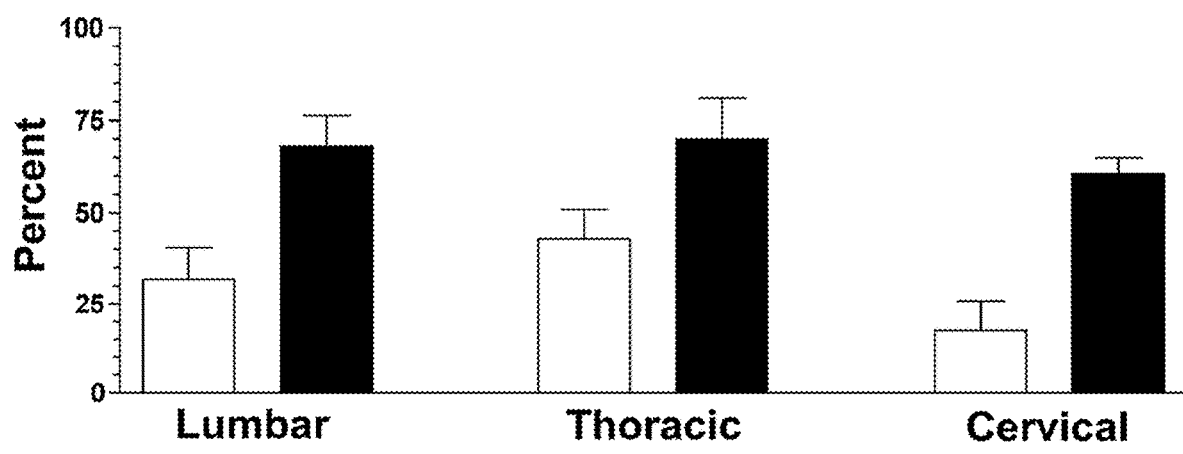
Figure 4:
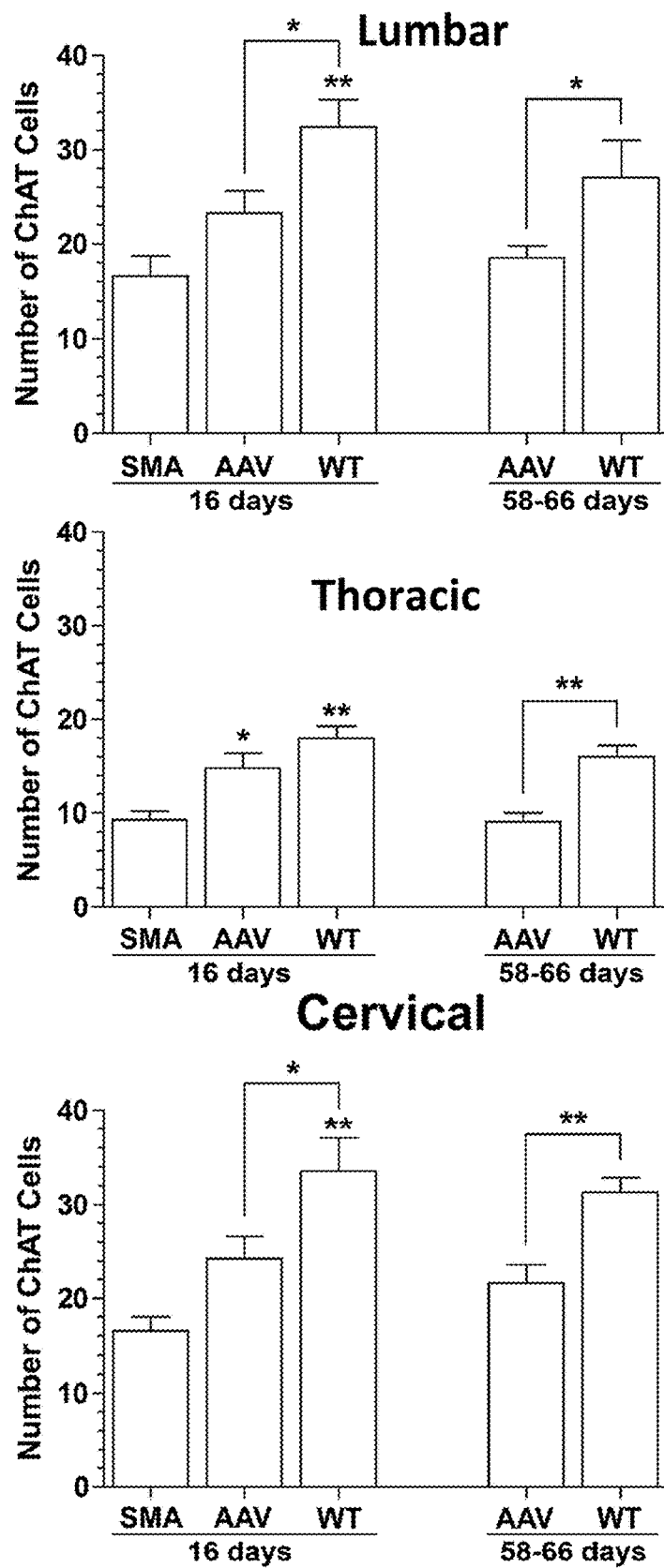
FIG. 4 shows motor neuron cell counts in the spinal cord in treated and untreated SMA mice. Shown are the average numbers of ChAT immuno-positive neurons counted on 10 μm tissue sections for each group. Numbers represent counts of every tenth section from different levels of the cervical, thoracic, lumbar and sacral segments. Values represent the mean±SEM. Key: *, p<0.05; , p<0.01; *, p<0.001.

Co-localization with ChAT and hSMN confirmed that a subset of the transduced cells were indeed motor neurons (FIGS. 3F-3I). At 16 days, approximately 18-42% of ChAT-positive cells in the lumbar, thoracic and cervical segments of the spinal cord were transduced by AAV-hSMN1 (FIG. 3J). This percentage was higher at 58-66 days, in which 60-70% of motor neurons expressed exogenous hSMN in the three spinal cord segments (FIG. 3J). There was an overall increase in the number of motor neurons in treated SMA mice compared to untreated mutants (FIG. 4). However, there were significantly less motor neurons in treated SMA mice compared to wild type mice at 16 and 58-66 days (FIG. 4).

hSMN immunostaining of cervical tissue sections from untreated, Intracerebroventricular (ICV)-only injected, and lumbar-only injected heterozygote mice was performed. ICV injections alone did not contribute to appreciable AAV transduction patterns in the brain but nevertheless generated substantial targeting of the cervical spinal cord that was not achievable with lumbar-only injections. In particular, the ICV-only injections resulted in the cervical spinal cord expression of hSMN. This was in contrast to intraparenchymal injection of the lumbar segment that showed very little transduction of the cervical spinal cord, presumably due to the distal proximity from the injection site. On occasion, SMN immunopositive signal that possessed a gem-like appearance was observed in the nucleus of untreated heterozygote and wild-type mice. However, this immunostaining pattern was not observed in the nucleus of untreated SMA mice.

Thus, the combination of ICV and lumbar injections in P0 mice provided broad, widespread transduction of the spinal cord. ICV injections of AAV8-hSMN targeted the cervical spinal cord for transduction.

Example 3

Effects of AAV Treatment on Myofiber Size, the NMJ, and Behavior

Figure 5A:
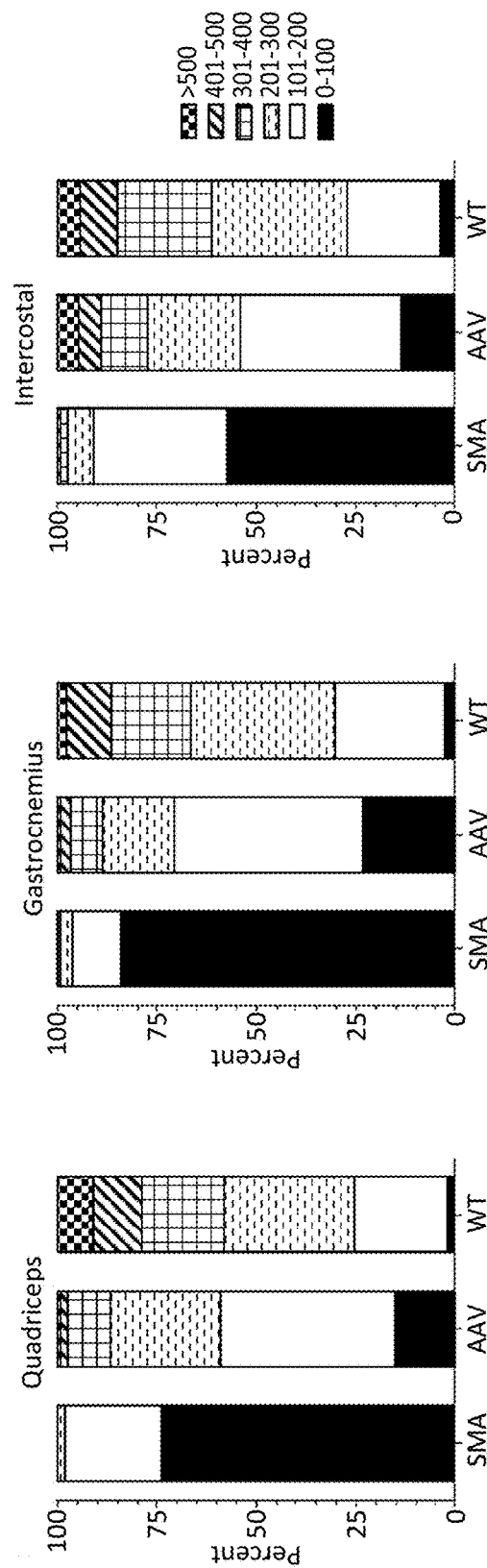
FIGS. 5A-5C show the myofiber cross-section area from muscle groups in treated and untreated SMA mice. The myofiber cross-section area from multiple muscle groups was increased with AAVhSMN1 treatment. Stacked graphs of the quadriceps, gastrocnemius and intercostal muscles from 16 (FIG. 5A) and 58-66 (FIG. 5B) days showed that the distribution of myofiber sizes were similar between the treated SMA and the wild type mice. The overall average at 16 days showed that the myofiber cross-section area was significantly higher with treatment (FIG. 5C). Furthermore at 58-66 days, the average area was statistically similar between treated SMA mice and age-matched wild-type in the gastrocnemius and intercostal muscles (FIG. 5C). Values represent the mean±SEM. Key: WT, untreated wild type; HET, untreated heterozygote; SMA, untreated knockout; AAV, AAVhSMN1-treated SMA mice; *, $p<0.05$; , $p<0.01$; *, $p<0.001$.
Figure 5B:
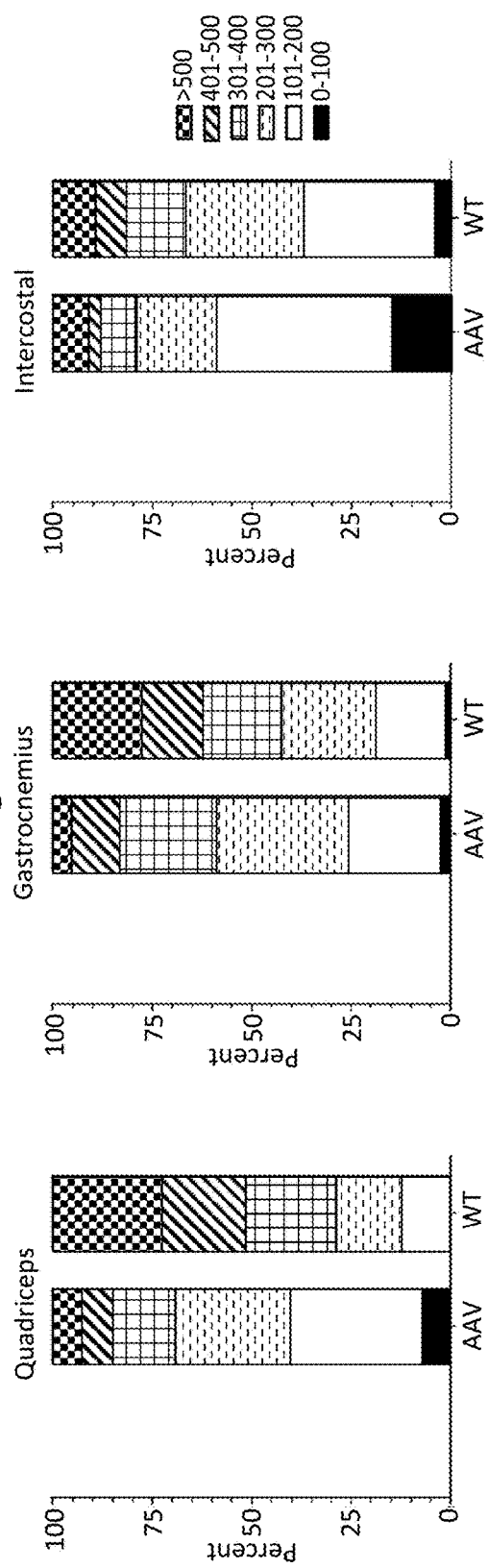
Figure 5C:
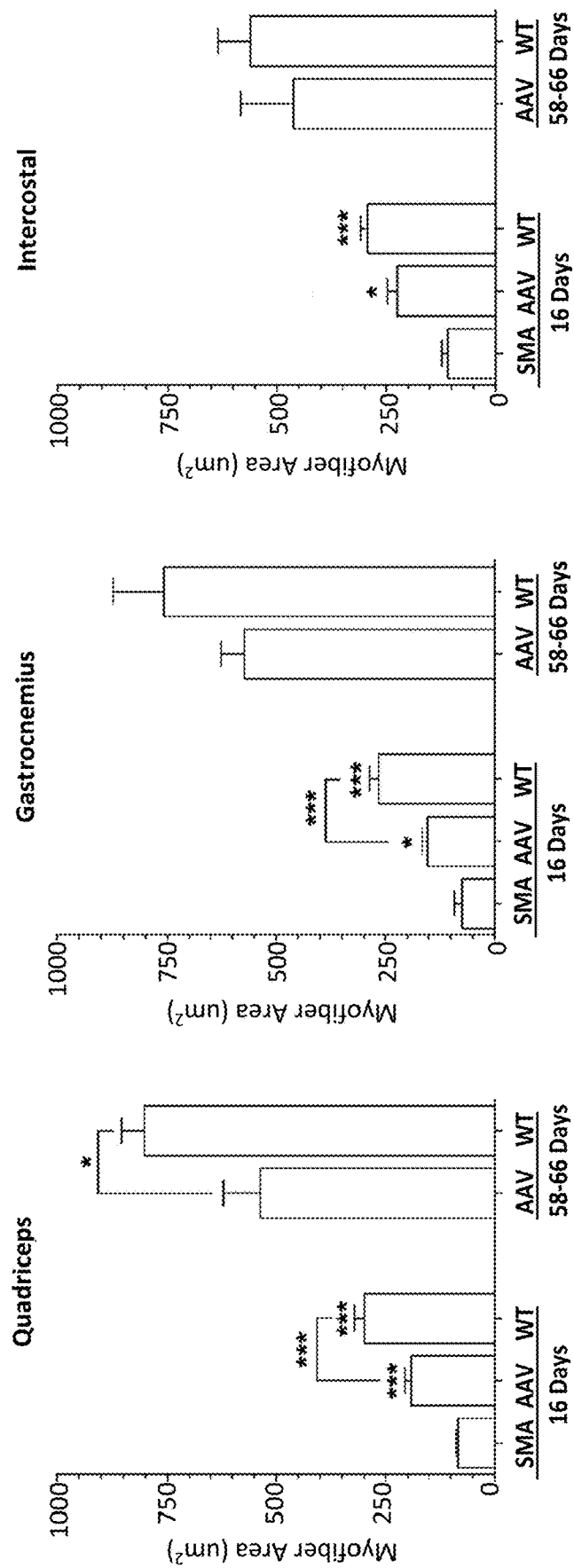

The quadriceps (proximal), gastrocnemius (distal) and intercostal (respiratory) muscles were chosen for analysis because they show marked degeneration. In untreated SMA mice at 16 days, myofibers were small and the majority of individual cells contained a cross-section area of <100 um$^2$ (FIG. 5A). Less than 10% of the myofibers from the untreated SMA mice contained a cross-section area of more than 200 um$^2$. In contrast, the distribution of myofiber sizes in AAV-hSMN1 treated SMA mice was similar to wild type, and many cells possessed a cross-section area of more than 200 and more than 400 μm$^2$ at 16 and 58-66 days, respectively (FIGS. 5A and 5B). The overall average at 16 days showed that the myofibers from treated SMA mice were more than 2-fold larger than those from untreated SMA mice (FIG. 5C). Furthermore, the average myofiber cross-section area in treated SMA mice at 58-66 days was 67%, 76%, and 82% that of wild type mice in the quadriceps, gastrocnemius, and intercostal, respectively (FIG. 5C).

Analysis of the neuromuscular junction (NMJ) from untreated SMA mice at 16 days showed abnormal accumulation of neurofilament protein at the pre-synaptic termini (FIG. 6A). Approximately 75-90% of the pre-synaptic termini from the quadriceps, gastrocnemius, and intercostal showed this hallmark pathology in untreated SMA mice (FIG. 6F). In contrast, the majority of the pre-synaptic termini from AAV-hSMN1 treated SMA mice did not contain this collapsed structure (FIG. 6B, 6D). Only 10-25% and 5% of the pre-synaptic termini from treated SMA mice showed this hallmark pathology at 16 and 58-66 days, respectively (FIG. 6F). However, treatment resulted in more branching at the pre-synaptic termini compared to wild type (FIG. 6B-6E). On the post-synaptic NMJ from treated SMA and wild type mice, α-bungarotoxin staining produced a 'pretzel-like' structure that was indicative of a functional network of acetylcholine receptors (FIG. 6B-6E).

Figure 7A:
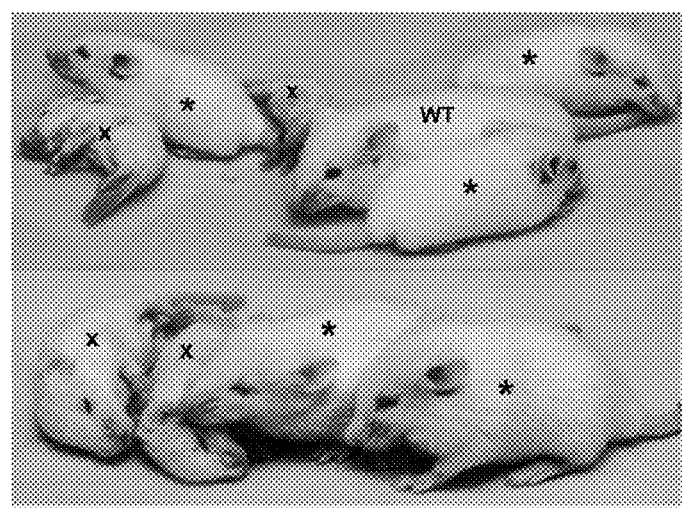
FIGS. 7A-7F show the results of behavioral tests in treated and untreated SMA mice. Treated SMA mice showed significant improvements on behavioral tests. Treated SMA (asterisk) and untreated wild-type (WT) mice were substantially fitter than untreated SMA mice (labeled 'x') at 16 days (FIG. 7A). Treated SMA mice were also significantly heavier than untreated SMA controls from day 11 and onwards (FIG. 7B). Treated SMA mice performed significantly better than untreated SMA mice on the righting reflex (FIG. 7C), negative geotaxis (FIG. 7D), grip strength (FIG. 7E) and hindlimb splay (FIG. 7F) tests. Treated SMA mice were statistically identical to wild-type and heterozygote mice on the righting reflex and negative geotaxis tests at 12-16 days (FIGS. 7C and 7D). Values represent the mean±SEM. Key: untreated WT (open circle), untreated heterozygote (open triangle); untreated SMA (open square); AAVhSMN1-treated SMA mice (closed square); *, $p<0.05$; , $p<0.01$; *, $p<0.001$.
Figure 7B:
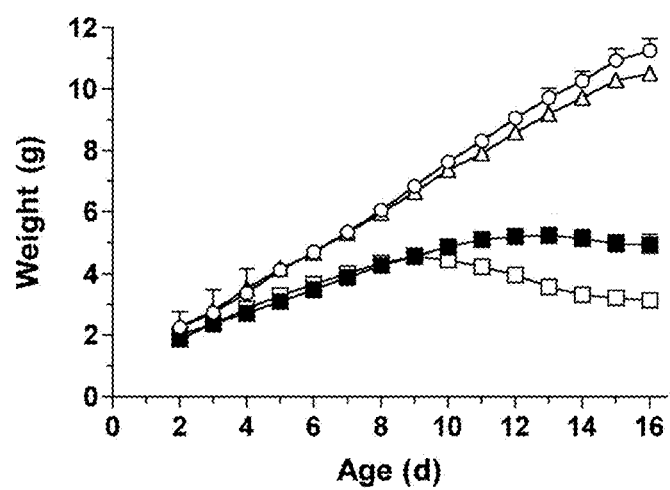
Figure 7C:
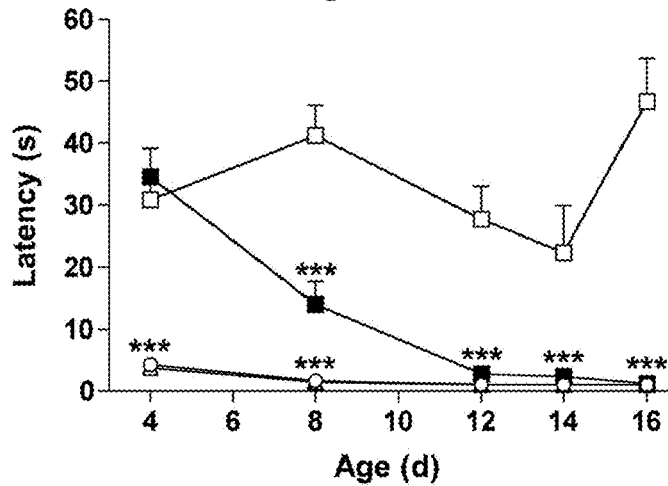
Figure 7D:
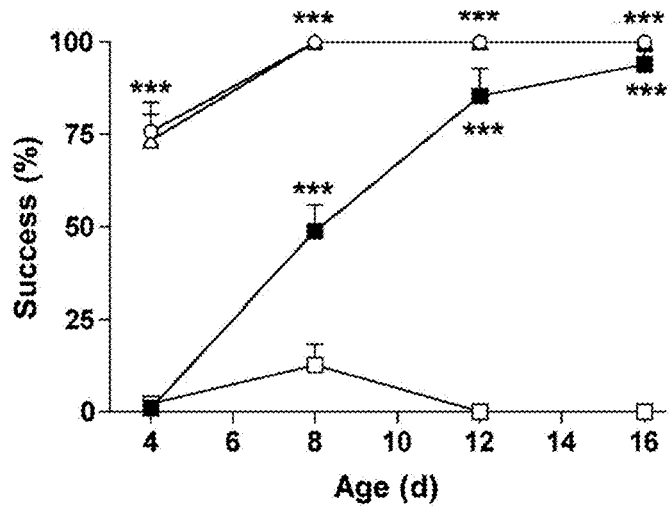
Figure 7E:
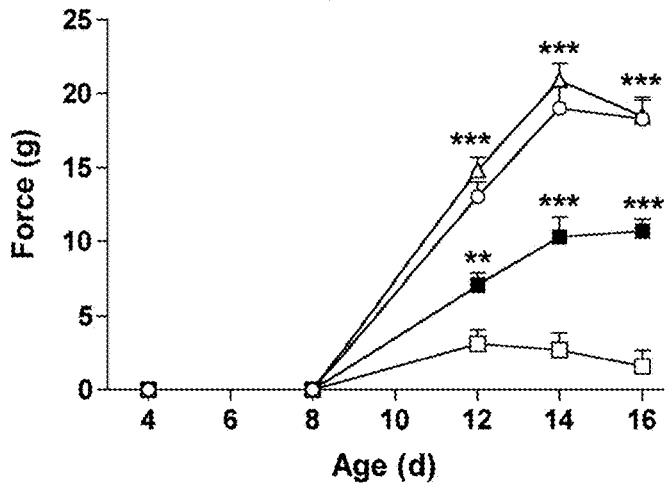
Figure 7F:
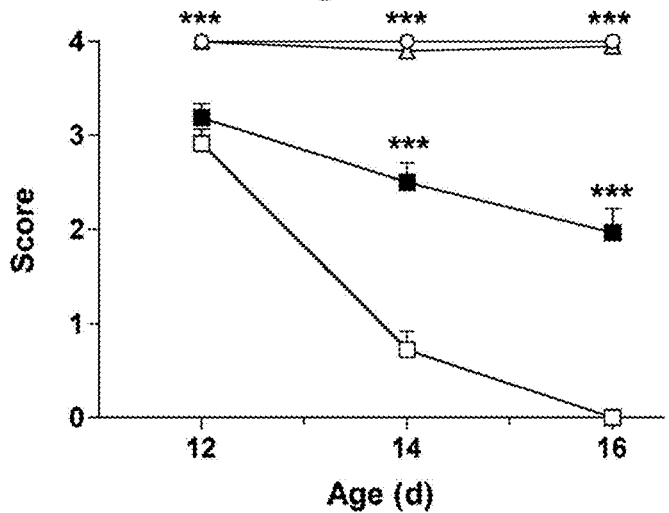

Treated and untreated mice were subjected to periodic behavioral tests that have been validated for this animal model (Butchbach et al., Neurobiol. Dis. (2007) 27:207-219; El-Khodar et al., Exp. Neurol. (2008) 212:29-43). Treated SMA mice had good body scores and ambulatory skills, whereas untreated SMA mice were emancipated and paralyzed (FIG. 7A). Treated SMA mice were significantly heavier than untreated SMA controls, although they never reached wild-type size (FIG. 7B). Treated SMA mice showed a significant improvement in righting latency (FIG. 7C). There also was a significant improvement in the treated SMA mice to complete the negative geotaxis test, which measures spatial locomotive behavior (FIG. 7D). Furthermore, treated SMA mice showed significant improvements in grip strength and in the ability to splay their hindlimbs (FIG. 7E, 7F).

Example 4

Effects on Longevity Using Self-Complementary AAV

Without being limited as to theory, self-complementary AAV (scAAV) vectors are predicted to have faster expression kinetics due to the double-stranded recombinant genome (reviewed in McCarty, D. M. Molec. Ther. (2008) 16:1648-1656). This rapid increase in expression may be beneficial in highly aggressive diseases or conditions where the temporal window of intervention is small. Thus, to determine whether earlier expression could improve efficacy, a scAAV vector s AAV-hSMN1) was engineered and tested. Using the same site of injections as performed in Example 1, a dose of 1.7 e10 genome copies of scAAV-hSMN1 was administered into P0 SMA mice.

Figure 8:
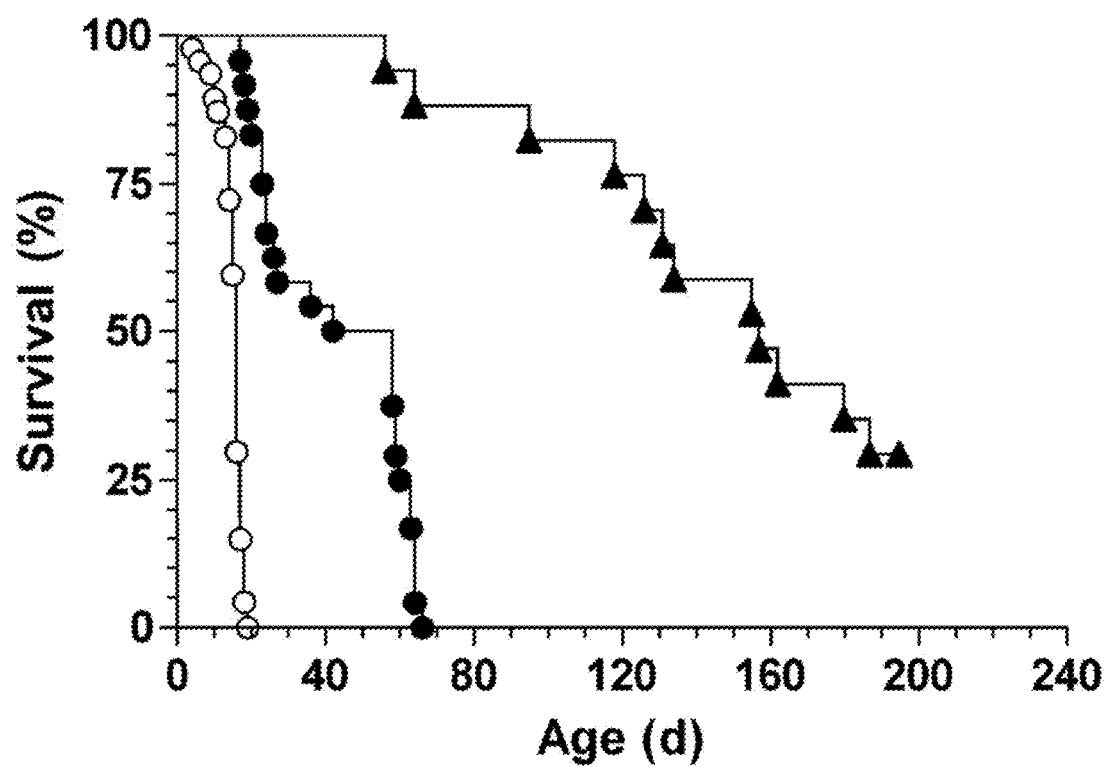
FIG. 8 shows survival of scAAVhSMN1-treated and untreated mice. Treatment with scAAVhSMN1 increased survival in SMA mice. SMA mice treated at P0 with scAAVhSMN1 (n=17, closed triangles) had a median lifespan of 157 days ($p<0.0001$), compared to 16 days in untreated SMA mice (n=47, open circles).

Treatment with scAAV-hSMN1 resulted in a striking and remarkable improvement in median survival of 157 days ($p<0.0001$), which was a +214% and +881% increase compared to AAV-hSMN1-treated and untreated SMA mice, respectively (FIG. 8). Approximately 42% of the scAAV-treated mice possessed a more than 1000% increase (log-fold increase) in median survival. Furthermore, scAAV2/8-GUSB-hSMN1 treatment resulted in 88% of the SMA mice living beyond 66 days, in contrast to 0% with AAV2/8-CBA-hSMN1. The scAAV-treated SMA mice possessed healthy body scores, were well groomed, gained weight, and maintained ambulation throughout their life. Interestingly, scAAV-treated SMA mice developed only mild hindlimb necrosis that never progressed into a severe phenotype. The majority of scAAV-treated SMA mice were sacrificed due to an unforeseen and sudden appearance of respiratory distress, which included audible clicking gasps when breathing and a decreased rate of respiration.

To better understand the basis for the observed increase in survival with scAAV8-hSMN, additional SMA mice were treated at P0 and sacrificed at 16 or 64 (58-66 d) days post-injection, and analyzed with the long-lived scAAV8-treated mice from the survival curve (FIG. 8). At 16 days, SMN expression levels from the scAAV8-hSMN group were approximately 60-90% to those observed in WT animals. These levels were substantially less than that achieved with AAV8-hSMN treatment at this time point. In the scAAV8-hSMN-treated SMA mice, SMN levels in both the lumbar and thoracic segments were above or at WT levels at 58-66 and 120-220 days, respectively (FIGS. 2A and 2B). In contrast, SMN levels in the cervical spinal cord remained relatively low at all time points.

Comparison of AAV vector tropism in the lumbar spinal cord was examined using hSMN immunostaining on frozen tissue sections from untreated SMA, AAV8-hSMN-treated SMA, and scAAV8-hSMN-treated SMA mice at 16 days and 157 days post-injection. A diffuse hSMN immunostaining pattern consistent with glial cell morphology was observed at 16 days with AAV8-hSMN. Doubling immunolabeling of hSMN and mGFAP confirmed that a subset of the AAV8-hSMN-transduced cells were astrocytes. In contrast, scAAV8 treatment resulted in hSMN expression only in distinct cell bodies with neuronal morphology, which did not co-localize with GFAP. Double immunolabeling of hSMN and the motor neuron marker mChAT confirmed that a subset of cells transduced by scAAV8-hSMN and AAV8-hSMN were motor neurons. hSMN expression was also observed in the interneuronal cell layers of the spinal cord with both viral vectors, as exemplified by scAAV8-hSMN at 157 days. Thus, in contrast to AAV8-hSMN, histological analysis of scAAV8-hSMN-treated SMA mice showed hSMN expression was largely restricted to neurons.

Figure 10A:
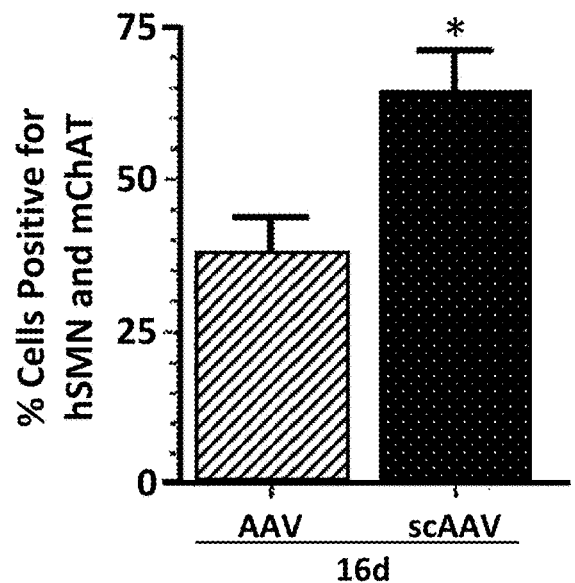
FIGS. 10A-10F shows that scAAV8-hSMN expression increases motor neuron counts and improves NMJ in SMA mice.
Figure 10B:
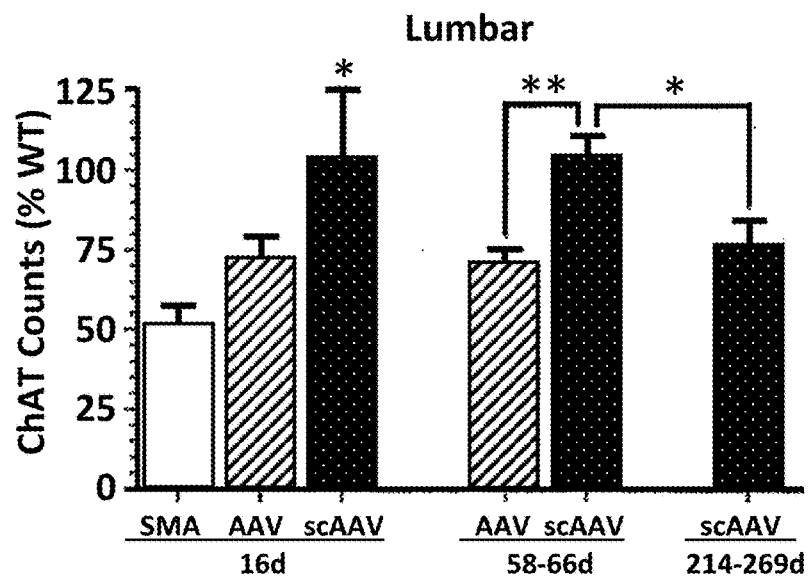
Figure 10C:
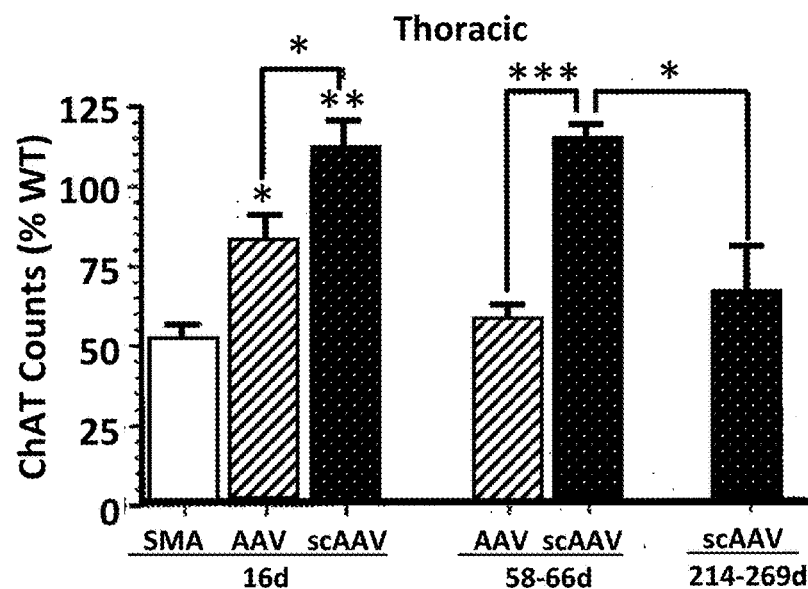
Figure 10D:
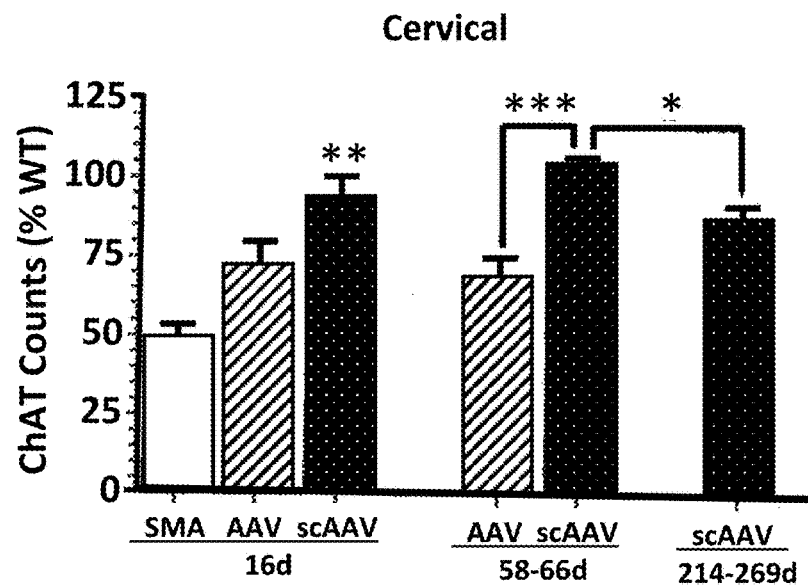
Figure 10E:
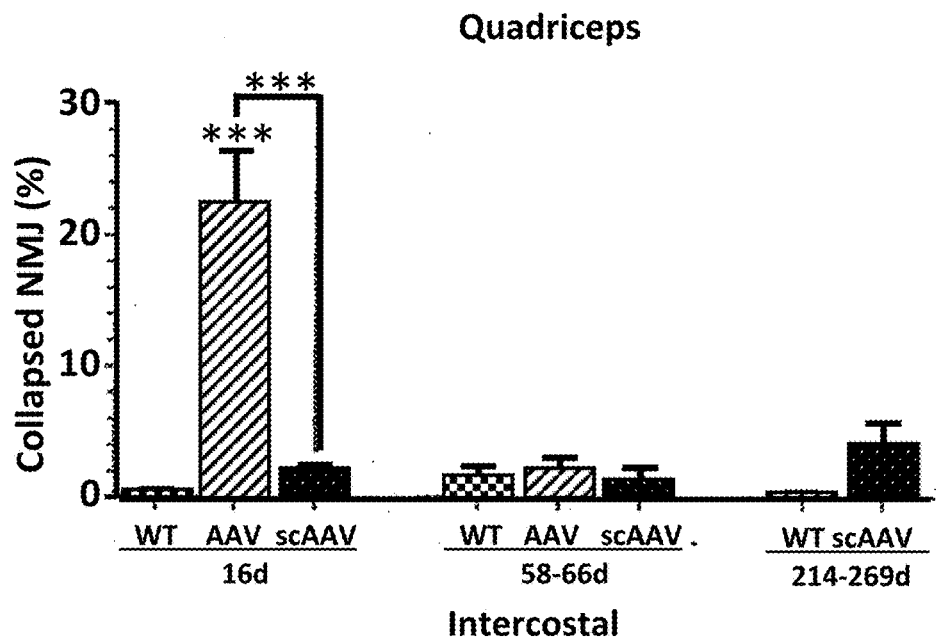
Figure 10F:
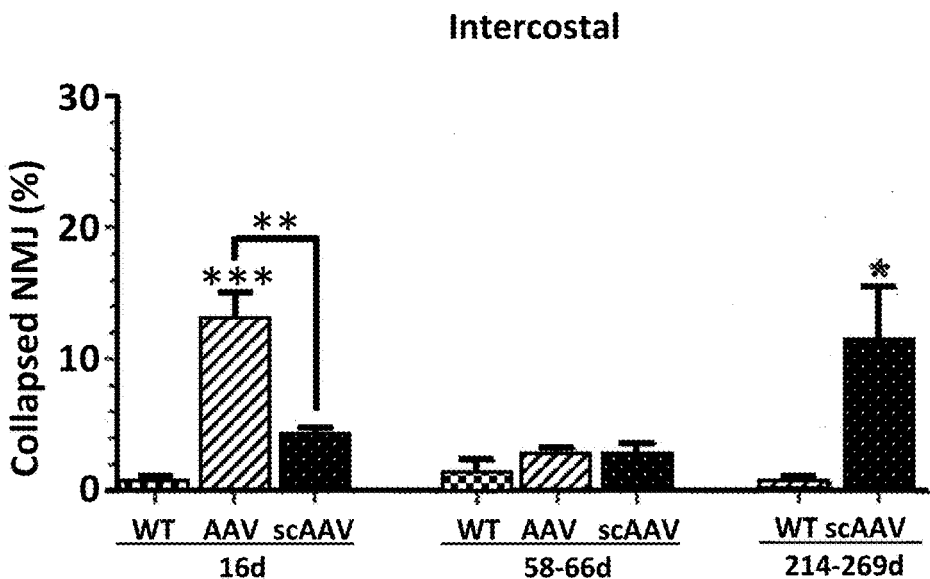

Furthermore, double immunostaining with hSMN and mChAT showed a significant increase in the percentage of motor neurons transduced with scAAV8-hSMN compared to AAV8-hSMN (FIG. 10A). The more efficient targeting of motor neurons with scAAV correlated with a significant increase in the number of ChAT-positive cells (FIGS. 10B-10D). Analysis of the NMJ in the quadriceps and intercostal muscles at 16 days also showed a significant decrease in the number of collapsed structures with scAAV-hSMN compared to AAV8-hSMN (FIGS. 10E and 10F). However, there was an increase in the number of aberrant NMJs at 216-269 days that was concomitant with the decline of motor neuron cell counts in the scAAV-hSMN group (FIGS. 10B-10F).

To summarize, injection of AAV8-hSMN at birth into the CNS of a mouse model of SMA resulted in widespread expression of SMN throughout the spinal cord that translated to a robust improvement in skeletal muscle physiology. Treated SMA animals also displayed significant improvements on behavioral tests indicating that the neuromuscular junction was functional. Importantly, treatment with AAV8-hSMN increased the median lifespan of SMA mice to 50 days compared to 15 days for untreated controls. Moreover, SMA mice injected with a self-complementary AAV vector resulted in improved efficacy including a significant extension in median survival for 157 days. These data evidence that CNS-directed, AAV-mediated SMN augmentation is highly efficacious in addressing both the neuronal and muscular pathologies of a severe mouse model of SMA.

Thus, compositions and methods for treating spinal cord disorders are disclosed. Although preferred embodiments of the subject invention have been described in some detail, it is understood that obvious variations can be made without departing from the spirit and the scope of the invention as defined herein.

The invention claimed is:

1. A method of treating spinal muscular atrophy (SMA) comprising administering to a subject in need thereof a therapeutically effective amount of recombinant adeno-associated virus (rAAV) virions comprising a self-complementary adeno-associated virus (scAAV) vector comprising a heterologous nucleic acid construct, wherein the heterologous nucleic acid construct comprises:
   a. a first AAV2 inverted terminal repeat (ITR);
   b. a cytomegalovirus enhancer/chicken-β actin (CBA) promoter;
   c. a polynucleotide encoding a survival motor neuron (SMN) protein comprising the amino acid sequence of SEQ ID NO: 2; and
   d. a second AAV2 ITR, and
   wherein the rAAV virions comprise an AAV8 or AAV9 capsid, and
   wherein the scAAV virions are administered via intrathecal injection.

2. The method of claim 1, wherein the first or the second ITR is mutated.

3. The method of claim 2, wherein the first or the second ITR comprises a mutation in a terminal resolution sequence.

4. The method of claim 1, wherein a single-dose of the rAAV virions is administered.

5. A method of expressing survival motor neuron (SMN) protein in motor neurons of the spinal cord comprising administering to a subject in need thereof a therapeutically effective amount of recombinant adeno-associated virus (rAAV) virions, wherein the rAAV virions comprise a self-complementary adeno-associated virus (scAAV) vector comprising a heterologous nucleic acid construct,
   wherein the subject has spinal muscular atrophy (SMA), wherein the heterologous nucleic acid construct comprises:
   a. a first AAV2 inverted terminal repeat (ITR);
   b. a cytomegalovirus enhancer/chicken-β actin (CBA) promoter;
   c. a polynucleotide encoding a survival motor neuron (SMN) protein comprising the amino acid sequence of SEQ ID NO: 2; and
   d. a second AAV2 ITR, and
   wherein the rAAV virions comprise an AAV8 or AAV9 capsid, and
   wherein the rAAV virions are administered via intrathecal injection.

6. The method of claim 5, wherein the first or the second ITR is mutated.

7. The method of claim 6, wherein the first or the second ITR comprises a mutation in a terminal resolution sequence.

8. The method of claim 5, wherein a single-dose of the rAAV virions is administered.

9. The method of claim 5, wherein the motor neurons of the spinal cord are in the dorsal and ventral horns of the spinal cord.

10. The method of claim 5, wherein the motor neurons of the spinal cord are in the lumbar, thoracic and/or cervical segments of the spinal cord.

11. A method of increasing survival, comprising administering to a subject in need thereof a therapeutically effective amount of recombinant adeno-associated virus (rAAV) virions,
wherein the subject has spinal muscular atrophy (SMA),
wherein the rAAV virions comprise a self-complementary adeno-associated virus (scAAV) vector comprising a heterologous nucleic acid construct, wherein the heterologous nucleic acid construct comprises:
  a. a first AAV2 inverted terminal repeat (ITR);
  b. a cytomegalovirus enhancer/chicken-β actin (CBA) promoter;
  c. a polynucleotide encoding a survival motor neuron (SMN) protein comprising the amino acid sequence of SEQ ID NO: 2; and
  d. a second AAV2 ITR,
wherein the rAAV virions comprise an AAV8 or AAV9 capsid, and
wherein the rAAV virions are administered via intrathecal injection.

12. The method of claim 11, wherein a single-dose of the rAAV virions is administered.

13. The method of claim 1, wherein about $10^6$ to about $10^{15}$ rAAV virions are administered.

14. The method of claim 5, wherein about $10^6$ to about $10^{15}$ rAAV virions are administered.

15. The method of claim 11, wherein about $10^6$ to about $10^{15}$ rAAV virions are administered.

16. The method of claim 11, wherein the first or the second ITR is mutated.

17. The method of claim 16, wherein the first or the second ITR comprises a mutation in a terminal resolution sequence.

18. The method of claim 2, wherein the mutation comprises a deletion at the terminal resolution site of the first or the second ITR.

19. The method of claim 6, wherein the mutation comprises a deletion at the terminal resolution site of the first or the second ITR.

20. The method of claim 16, wherein the mutation comprises a deletion at the terminal resolution site of the first or the second ITR.

* * * * *

SEQUENCE LISTING

```
Sequence total quantity: 2
SEQ ID NO: 1              moltype = DNA   length = 885
FEATURE                   Location/Qualifiers
misc_feature              1..885
                          note = human survival motor neuron (SMN1) gene
source                    1..885
                          mol_type = genomic DNA
                          organism = Homo sapiens
SEQUENCE: 1
atggcgatga gcagcggcgg cagtggtggc ggcgtcccgg agcaggagga ttccgtgctg   60
ttccggcgcg gcacaggcca gagcgatgat tctgacattt gggatgatac agcactgata  120
aaagcatatg ataaagctgt ggcttcattt aagcatgctc taaagaatgg tgacatttgt  180
gaaacttcgg gtaaaccaaa aaccacacct aaaagaaaac ctgctaagaa gaataaaagc  240
caaaagaaga atactgcagc ttccttacaa cagtggaaag ttggggacaa atgttctgcc  300
atttggtcag aagacggttg catttaccca gctaccattg cttcaattga ttttaagaga  360
gaaacctgtg ttgtggttta cactggatat ggaaatagag aggagcaaaa tctgtccgat  420
ctactttccc caatctgtga agtagctaat aatatagaac aaaatgctca agagaatgaa  480
aatgaaagcc aagtttcaac agatgaaagt gagaactcca ggtctcctgg aaataaatca  540
gataacatca agcccaaatc tgctccatgg aactcttttc tccctccacc acccccatg   600
ccagggccaa gactgggacc aggaaagcca ggtctaaaat tcaatggccc accaccgcca  660
ccgccaccac caccacccca cttactatca tgctggctgc ctccatttcc ttctggacca  720
ccaataattc ccccaccacc tcccatatgt ccagattctc ttgatgatgc tgatgctttg  780
ggaagtatgt taatttcatg gtacatgagt ggctatcata ctggctatta tatgggtttc  840
agacaaaatc aaaaagaagg aaggtgctca cattccttaa attaa                  885

SEQ ID NO: 2              moltype = AA    length = 294
FEATURE                   Location/Qualifiers
REGION                    1..294
                          note = human survival motor neuron (SMN1) gene
source                    1..294
                          mol_type = protein
                          organism = Homo sapiens
SEQUENCE: 2
MAMSSGGSGG GVPEQEDSVL FRRGTGQSDD SDIWDDTALI KAYDKAVASF KHALKNGDIC    60
ETSGKPKTTP KRKPAKKNKS QKKNTAASLQ QWKVGDKCSA IWSEDGCIYP ATIASIDFKR   120
ETCVVVYTGY GNREEQNLSD LLSPICEVAN NIEQNAQENE NESQVSTDES ENSRSPGNKS   180
DNIKPKSAPW NSFLPPPPPM PGPRLGPGKP GLKFNGPPPP PPPPPPHLLS CWLPPFPSGP   240
PIIPPPPPIC PDSLDDADAL GSMLISWYMS GYHTGYYMGF RQNQKEGRCS HSLN         294
```